US012447343B2

(12) United States Patent
Lai et al.

(10) Patent No.: US 12,447,343 B2
(45) Date of Patent: Oct. 21, 2025

(54) NEUROSTIMULATION DEVICE FOR BLOCKING BLOOD FLOW BETWEEN ELECTRODES

(71) Applicant: Galvani Bioelectronics Limited, Stevenage (GB)

(72) Inventors: Christopher Shen-Yuan Lai, Wilmington, DE (US); Kenneth Douglas Rys, Wilmington, DE (US); Matteo Donega, Brentford (GB); Isha Gupta, Brentford (GB)

(73) Assignee: GALVANI BIOELECTRONICS LIMITED, Stevenage (GB)

( * ) Notice: Subject to any disclaimer, the term of this patent is extended or adjusted under 35 U.S.C. 154(b) by 249 days.

(21) Appl. No.: 17/415,592

(22) PCT Filed: Dec. 16, 2019

(86) PCT No.: PCT/IB2019/060855
§ 371 (c)(1),
(2) Date: Jun. 17, 2021

(87) PCT Pub. No.: WO2020/128790
PCT Pub. Date: Jun. 25, 2020

(65) Prior Publication Data

US 2022/0347470 A1 Nov. 3, 2022

Related U.S. Application Data

(60) Provisional application No. 62/867,033, filed on Jun. 26, 2019, provisional application No. 62/782,779, filed on Dec. 20, 2018.

(51) Int. Cl.
*A61N 1/36* (2006.01)

(52) U.S. Cl.
CPC ......... *A61N 1/3606* (2013.01); *A61N 1/3616* (2013.01); *A61N 1/36178* (2013.01)

(58) Field of Classification Search
CPC .... A61N 1/05; A61N 1/3606; A61N 1/36117; A61N 1/3616; A61N 1/36178
See application file for complete search history.

(56) References Cited

U.S. PATENT DOCUMENTS

| | | | | |
|---|---|---|---|---|
| 7,343,202 B2 * | 3/2008 | Mrva | A61N 1/0524 607/116 |
| 7,756,583 B2 * | 7/2010 | Demarais | A61N 1/36182 607/116 |

(Continued)

FOREIGN PATENT DOCUMENTS

WO WO2015057696 4/2015

*Primary Examiner* — Amanda K Hulbert
(74) *Attorney, Agent, or Firm* — McAndrews, Held & Malloy, Ltd.

(57) ABSTRACT

A neurostimulation device 1 for non-destructively stimulating neural activity in a nerve 3 in proximity to a blood vessel 5. The neurostimulation device 1 comprises a catheter 7 for insertion into the blood vessel 5; a proximal electrode 11 offset from a distal electrode 9 along a length of the catheter 7; and an insulator 13 positioned between the proximal electrode 11 and the distal electrode 9 on the catheter 7. The insulator 13 has a contracted configuration in which the size of the insulator 13 allows the catheter 7 to travel inside the blood vessel 5. The insulator 13 has an expanded configuration in which the insulator 13 blocks blood flowing through the blood vessel between the proximal electrode 11 and the distal electrode 9. The neurostimulation device 1 comprises a stimulator 15 arranged to apply an electrical signal between the proximal electrode 11 and the distal electrode 9 when the insulator 13 is in the expanded configuration, thus inducing electrical activity in a wall portion of the blood vessel between the proximal and distal elec- (Continued)

trodes 9, 11. There is also an insulation portion between the distal electrode 9 and a distal end of the catheter 7 for offsetting the distal electrode 9 from a wall of the blood vessel 5.

14 Claims, 40 Drawing Sheets

(56) References Cited

U.S. PATENT DOCUMENTS

| | | | | |
|---|---|---|---|---|
| 8,548,600 | B2 | 10/2013 | Deem et al. | |
| 9,861,820 | B2 * | 1/2018 | Greenberg | A61N 1/0531 |
| 10,143,419 | B2 * | 12/2018 | Toth | A61B 5/6852 |
| 2002/0156513 | A1 * | 10/2002 | Borkan | A61N 1/0551 607/117 |
| 2005/0075702 | A1 | 4/2005 | Shafer | |
| 2015/0111918 | A1 * | 4/2015 | Sobotka | A61B 18/20 514/183 |
| 2018/0117319 | A1 * | 5/2018 | Chew | A61N 1/3605 |
| 2019/0290913 | A1 * | 9/2019 | Blancou | A61N 1/36171 |
| 2019/0321640 | A1 * | 10/2019 | Carmena | A61B 5/6884 |

* cited by examiner

Sham SpNS 1x Stim SpNS 2x Stim

Optimal response comes from position A (the proximal SpA)

The catheter developed in ANSYS Maxwell 3D. All dimensions are in mm.

The catheter within the artery. All dimensions are in mm.

The final cross-sectional image of the FEM following re-sizing to allow the catheter to fit in the artery.

The voltage along a line at the center of a fascicle resulting from a +1.0mA anodic current and a -1.0mA cathodic current.

Most of the fascicles in the model were small, containing relatively few axons. 38% of the fascicles comprised 83% of the total fascicle area.

The average threshold for the 100 axons within each fascicle. The 29 lines are from the 29 fascicles in the model. The darker the line, the larger the cross-sectional area of that fascicle and the more axons within the entire axon population that are represented by the line.

The average threshold for all axons within the model.

NEUROSTIMULATION DEVICE FOR BLOCKING BLOOD FLOW BETWEEN ELECTRODES

This application is a U.S. National Phase Application under 35 U.S.C. § 371 of International Application PCT/IB2019/060855, filed Dec. 16, 2019 which claims the benefit of U.S. Provisional Application No. 62/782,779, filed on Dec. 20, 2018 and 62/867,033, filed Jun. 26, 2019. Each of these applications is hereby incorporated by reference in its entirety for all purposes.

TECHNICAL FIELD

This disclosure relates to a neurostimulation device and a method for non-destructively stimulating a nerve, in particular for stimulating neural activity in the nerve.

BACKGROUND ART

Neurostimulation devices exist that use a balloon to position a catheter comprising electrodes within a blood vessel for electrically stimulating neural activity in a nerve located around the blood vessel. These devices maintain blood flow around the balloon so that blood is able to flow from one electrode to another. Also, the balloon is positioned either proximally or distally away from the electrodes rather than in between the electrodes. In this arrangement, the blood travelling in the blood vessel provides a direct conductive channel between the electrodes for the electrical signal being applied. In addition, electrodes of these devices are allowed to touch the wall of the blood vessel for stimulating neural activity in the surrounding nerve fibres.

These conventional neurostimulation devices suffer from drawbacks, such as the majority of the current being shunted through the blood in the vessel (which reduces safety/efficacy as more charge may be required), undesirable variations in current between electrodes and uneven stimulation of the nerve fibers around the blood vessel.

SUMMARY OF THE INVENTION

In one aspect of the invention, there is a neurostimulation device for non-destructively stimulating a nerve in proximity to a blood vessel, optionally stimulating neural activity in the nerve, the neurostimulation device comprising: an indwelling device such as a catheter or stent for insertion into the blood vessel; a proximal electrode offset from a distal electrode along a length of the indwelling device, the electrodes for applying an electrical signal and connectable to a stimulator.

The neurostimulation device may be arranged to stimulate nerve fibers without damaging, destroying or cutting into tissue around the neurostimulation device, such as the blood vessel or the nerve fibers. Thus, the electrical signal applied by the neurostimulation device is kept below a level that would cause any ablation of tissue. Thus, the neurostimulation is for non-destructively stimulating neural activity in a nerve.

Wherein the indwelling device is a catheter, the neurostimulation device may further comprise: an insulator positioned between the proximal electrode and the distal electrode on the indwelling device; the insulator having a contracted configuration in which the size of the insulator allows the indwelling device to travel inside the blood vessel; the insulator having an expanded configuration in which the insulator blocks blood flowing through the blood vessel between the proximal electrode and the distal electrode when said electrodes are both disposed within the blood vessel; a stimulator arranged to provide stimulation, optionally arranged to apply an electrical signal, between the proximal electrode and the distal electrode when the insulator is in the expanded configuration, thus inducing electrical activity in a wall portion of the blood vessel between the proximal and distal electrodes; and an insulation portion between the distal electrode and a distal end of the indwelling device for offsetting the distal electrode from a wall of the blood vessel.

In the expanded configuration, the insulator of the neurostimulation device blocks, or in other words prevents, blood flowing between the electrodes. This prevents the flow of blood from interfering with electrical signals travelling from one electrode to another which allows the nerve to be stimulated in a reliable manner. In addition, the insulator prevents the blood in the blood vessel from providing a conductive channel between the electrodes; instead, the insulator promotes the transmission of electrical signals along an electrical channel between the electrodes via a wall in the blood vessel. This increases the amount of electricity that is directed towards the nerve fibers in proximity to, e.g., around, the blood vessel, rather than the bulk of the electrical signal travelling through the blood as can be the case with conventional arrangements.

The insulator and the insulation portion at the distal end of the indwelling device help to maintain the electrodes in a central location with respect to the bore of the blood vessel. These features help to maintain the electrodes close to the longitudinal axis of the blood vessel. This assists in keeping the electrodes at an equal distance from the nerve fibers around the circumference of the blood vessel. This, in turn, helps to evenly stimulate the nerve fibers instead of providing more stimulation to nerve fibers that are closer to the electrodes than to nerve fibres that are further away. These factors provide a device that can stimulate nerve fibers more effectively than conventional devices.

For the following summary and description of the invention it is envisaged that the indwelling device has a proximal end and a distal end. The distal end is the end of the indwelling device that would be inserted into a patient first and into the blood vessel. The proximal end may also be inserted into the patient, but only after the distal end has been inserted. Alternatively, where the indwelling device is a catheter, the proximal end may remain outside of the patient and the blood vessel. The distal electrode is the electrode that is closer to the distal end than the proximal electrode.

When the indwelling device is a catheter, the proximal electrode may be offset from the distal electrode by a minimum spacing of 1.5 cm along the length of the indwelling device. The proximal electrode may be offset from the distal electrode by a maximum spacing of 4 cm along the length of the indwelling device, preferably 2.5 cm along the length of the indwelling device. The proximal electrode may be offset from the distal electrode by a spacing of 1.5 cm to 2.5 cm (e.g. 2 cm) along the length of the indwelling device. These dimensions for offsetting the electrodes with respect to one another have been found to produce an electrical field that stimulates nerve fibers more effectively, without producing undesirable side effects like muscle contractions or off target organ stimulation. The closer the electrodes are, the smaller the stimulating field and the less effective the stimulation may be for some cases. On the other hand, the larger the distance between the electrodes, the larger the stimulating field, and off target stimulation can occur, such as in muscles, which causes muscle fasciculations. The spacing of 1.5 cm to 2.5 cm (e.g. 2 cm) may offer a balance for stimulating certain nerves (for example, splenic nerves) when using a catheter with an insulator provided between the proximal and distal electrodes as the indwelling device.

In cases where the indwelling device is a stent, the minimum spacing between a proximal and distal electrode may be smaller, for example 0.1-10 mm, optionally 1-10 mm.

The insulator may be positioned closer to the proximal electrode than the distal electrode. For example, there may be a gap of 2 mm between a distal edge of the proximal electrode and a proximal edge of the insulator. This helps to keep the proximal electrode in a central location with respect to the blood vessel. In this way, the distance between the proximal electrode and the wall of the blood vessel can be kept approximately equal around the inside circumference of the blood vessel.

During the stimulation phase of the electrical signal (e.g. the stimulation phase of a bipolar pulse), the proximal electrode may be an anode electrode (e.g. a return electrode), and the distal electrode may be a cathode electrode (e.g. a stimulating electrode). This assists in propagating an action potential distally in a direction extending away from the distal end of the indwelling device, which may be towards an organ e.g., in the case where the blood vessel is an artery. For instance, the indwelling device may be positioned inside the splenic artery in which case it is intended for the action potentials induced by applying an electrical signal to the electrodes to travel towards the spleen e.g., via the splenic nerve When the indwelling device is a catheter, the anode may be 1 cm in length. The proximal electrode may have a larger surface area than the distal electrode to minimise charge density at the electrode surface, and to minimize overall circuit impedance.

For the indwelling device, where the indwelling device is either a catheter or a stent, preferably, the distal electrode has a surface area of between 0.1 $cm^2$ and 0.01 $cm^2$, preferably between 0.04 $cm^2$ and 0.08 $cm^2$, more preferably between 0.05 $cm^2$ and 0.075 $cm^2$, still more preferably between 0.06 $cm^2$ and 0.07 $cm^2$, most preferably 0.067 $cm^2$.The proximal electrode and/or the distal electrode may be formed from platinum. The proximal electrode and/or the distal electrode may be formed from a platinum-iridium alloy. The ratio of platinum to iridium may be approximately 90:10. The proximal electrode and/or the distal electrode may be coated or treated in or with any one or more of: Titanium Nitride, PEDOT, IrOx, PtBlack, Laser roughening. These parameters assist in effectively stimulating the nerve fibers around the blood vessel.

The neurostimulation device may be positioned inside a blood vessel, for example the splenic artery for stimulating the splenic nerve or branches of the splenic nerve.

Where the indwelling device is a catheter, it may be adapted for implantation in the blood vessel using a guidewire. The neurostimulation device may comprise a guidewire and be used with the use of a guiding sheath and introducer and fluoroscopy. The guidewire may be 300 cm long.

The indwelling device (when a catheter) may be around 5 French (1.667 mm) in diameter. The indwelling device (when a catheter) may be around 130 cm long. The insulator may have a diameter of around 12 mm in the expanded configuration. The distal end of the indwelling device (when a catheter) may comprise an atraumatic tip. For instance, the distal end of the indwelling device may be curved which helps to avoid damage to the blood vessel.

The neurostimulation device may further comprise a second insulator positioned between the distal electrode and the distal end of the catheter. The second insulator comprises a contracted configuration in which the size of the insulator allows the catheter to travel inside the blood vessel; and an expanded configuration in which the second insulator blocks blood flowing through the blood vessel between the distal electrode and the distal end of the catheter. This helps to block blood flow more effectively, and also assists in retaining the distal electrode in a central location with respect to the bore of the blood vessel. These effects provide the advantages discussed above.

The amount of electrical current that is required for stimulation of neural activity is typically characterized by the pulse height that is supplied to the nerve by the electrical signal, which may vary depending on the waveform of the electrical signal. Through experimental studies, the inventors have found improved waveforms of the electrical signal which decrease the pulse height required in order to stimulate neural activity in a human nerve supplying the spleen, thereby optimizing the biological efficacy and reproducibility of stimulation parameters of the electrical signal for use in humans whilst reducing the burden on the stimulator. Thus, the electrical signal may comprise a pulse train having a pulse width >0.1 ms, more preferably ≥0.4 ms, still more preferably ≥1 ms, still more preferably >1 ms. Additionally or alternatively, the pulse width may be ≤5 ms, more preferably ≤3 ms, still more preferably ≤2 ms. Optionally, the pulse width may be between 0.1 and 5 ms, preferably between 0.4 and 4 ms, more preferably between 1 and 3 ms, still more preferably between 1.5 and 2.5 ms, preferably between 1.75 ms and 2.25 ms, more preferably between 1.9 ms and 2.1 ms, even more preferably 2 ms. Moreover, the pulse train may have an interphase delay of ≤0.3 ms, more preferably ≤0.25 ms. Additionally or alternatively, the interphase delay may be ≥0.1 ms, preferably ≥0.2 ms, more preferably 0.2 ms.

In another aspect of the invention, where the indwelling device is a catheter, there is a method for non-destructively stimulating a nerve in proximity to a blood vessel, optionally stimulating neural activity in the nerve, the method comprising: inserting an indwelling device into the blood vessel, the indwelling device comprising: a proximal electrode offset from a distal electrode along a length of the indwelling device; and an insulator positioned between the proximal electrode and the distal electrode on the indwelling device; changing the insulator from a contracted configuration in which the size of the insulator allows the indwelling device to travel inside the blood vessel to an expanded configuration in which the insulator blocks blood flowing through the blood vessel, e.g. between the proximal electrode and the distal electrode; providing electrical stimulation, optionally applying an electrical signal, between the proximal electrode and the distal electrode, thus stimulating a wall portion of the blood vessel between the proximal electrode and the distal electrode.

The inventors have shown that neuromodulation of the nerves supplying the spleen, in particular the nerves surrounding the splenic artery (referred to herein as splenic arterial nerves), increases survival of animals in an endotoxemic (LPS) shock model. In particular, the inventors found that applying an electrical signal to the splenic nerves stabilizes blood pressure, which drops dramatically in LPS-treated animals. Such stabilization reduces the maximum reduction in blood pressure. Hence, stimulation of the neural activity of splenic nerves provides a method for treating acute medical conditions, in particular life-threatening conditions, such as those having physiological changes associated with shock and cardiovascular dysfunction (e.g. trauma, haemorrhaging and septic shock). This would be particularly useful as a single treatment, e.g. in acute clinical settings.

Thus, in another aspect, the invention provides a method of stimulating neural activity in a nerve supplying the spleen to at least indirectly modulate systemic arterial blood pressure and/or central venous blood pressure in a subject. The method may comprise providing a neurostimulation device comprising an indwelling device such as an indwelling device for insertion into a splenic artery and at least one electrode associated with the indwelling device; inserting a distal end of the indwelling device into a splenic artery of the subject; positioning the at least one electrode of the neurostimulation device within the artery such that it is located in proximity to a splenic arterial nerve associated with the splenic artery so as to be in signalling (but not necessarily physical) contact with that nerve; and controlling the operation of the at least one electrode with at least one controller to apply an electrical signal to the nerve to stimulate neural activity therein. In some embodiments, the method is for the treatment of an acute medical condition. In some embodiments, the method is for the treatment of inflammation. In some embodiments, the method is for the treatment of an inflammatory disorder, e.g. an autoimmune disorder. In some embodiments, the method is for the treatment of a disease, disorder or condition associated with inflammation or cardiovascular dysfunction.

By using an endotoxemic (LPS) shock model, the inventors have also found that stimulation of the neural activity of the splenic arterial nerve is capable of modulating the level of inflammatory cytokines (e.g. TNFα) in an animal. The invention therefore provides a novel method of reducing inflammation, which may be useful for the treatment of a disease, disorder or condition associated with inflammation, e.g., for the treatment of an immune-mediated inflammatory disorder.

Thus, in another aspect, the invention provides a method of stimulating neural activity in a nerve supplying the spleen to modulate an inflammatory response in a subject, the method comprising providing a neurostimulation device comprising an indwelling device for insertion into a splenic artery and at least one electrode associated with the indwelling device; inserting a distal end of the indwelling device into a splenic artery of the subject; positioning the at least one electrode of the neurostimulation device within the artery such that it is located in proximity to a splenic arterial nerve associated with the splenic artery so as to be in signalling (but not necessarily physical) contact with that nerve; and controlling the operation of the at least one electrode with at least one controller to apply an electrical signal to the nerve to stimulate neural activity therein. In some embodiments, the subject is suffering from or at risk of inflammation. In some embodiments, the method is for the treatment of an inflammatory disorder, e.g., and autoimmune disorder. In some embodiments, the method is for the treatment of a disease, disorder or condition associated with inflammation. In some embodiments, the method is for the treatment of an acute medical condition.

In some embodiments, the modulation of an inflammatory response is a prevention of an inflammatory response, a suppression of an inflammatory response, or a reduction in an inflammatory response.

The inventors have further shown that neuromodulation of the nerves supplying the spleen can be achieved in an advantageous manner by using the neurostimulation device as described herein. Hence, stimulation of the neural activity of the splenic arterial nerve using the neurostimulation device of the invention may be an effective way for treating acute medical conditions, in particular life-threatening conditions, and/or diseases, disorders or conditions associated with inflammation. In another aspect, the invention provides an electrical signal for use in a method of the invention, for example in a method of treating an acute medical condition, a method of treating inflammation, a method of treating an inflammatory disorder, a method of treating a disease, disorder or condition associated with inflammation, or a method of modulating an inflammatory response. In this aspect, the electrical signal is provided by or obtained from a neurostimulation device, said device comprising an indwelling device for insertion into a splenic artery and at least one electrode associated with the indwelling device.

In another aspect, the invention also provides an electrical waveform for use in a method of the invention, for example in a method of treating an acute medical condition, a method of treating inflammation, a method of treating an inflammatory disorder, a method of treating a disease, disorder or condition associated with inflammation, or a method of modulating an inflammatory response. The electrical waveform is provided by or obtained from a neurostimulation device, said device comprising an indwelling device for insertion into a splenic artery and at least one electrode associated with the indwelling device.

In this aspect, the electrical waveform may cause reversible depolarization of the nerve membrane of a nerve supplying the spleen, wherein the nerve is associated with a neurovascular bundle (e.g. a splenic arterial nerve), such that an action potential is generated de novo in the nerve.

In another aspect, the invention provides a nerve which can be stimulated by the neurostimulation device of the invention, wherein the nerve supplies the spleen, and at least one electrode of the neurostimulation device is located in a blood vessel in proximity to the nerve. The nerve can be associated with a neurovascular bundle (e.g. a splenic arterial nerve). The nerve can be a modified nerve in that it can be distinguished from the nerve in its natural state, and wherein the nerve is located in a subject having an acute medical condition, or in a subject who is at risk of or suffering from inflammation, an inflammatory disorder, or a disease, disorder or condition associated within inflammation.

In some embodiments, the subject in any method as described herein is a mammal. In some embodiments, the subject is a human.

In another aspect, the invention provides a modified nerve obtainable by stimulating neural activity of a nerve supplying the spleen, according to a method of the invention. The stimulation of neural activity may be provided by a neurostimulation device comprising an indwelling device for insertion into a splenic artery and at least one electrode associated with the indwelling device. The nerve may be associated with a neurovascular bundle, and is preferably a splenic arterial nerve.

As noted above, the indwelling device may be a stent or a catheter.

A catheter may be a thin tube made from medical grade materials inserted in the body, for example blood vessels, for medical treatment that is connected to an external power source.

A stent, or a stent electrode stimulator, may allow blood flow through the stent and be placed in the body, for example blood vessel and stimulate nerves near or around the vessel.

The stent may be functionalised to receive and condition energy from a power source, where the stent is not physically connected to the power source when the power source is external to the body.

A catheter may be more suitable for acute use and a stent may be more suitable for chronic use.

BRIEF DESCRIPTION OF THE DRAWINGS

Embodiments of the invention will be described, by way of example, with reference to the following drawings, in which:

FIG. 6A is a Kaplan-Meier plot illustrating differences in survival time up to the pre-determined end-point at 2 hours post in vivo LPS injection. FIG. 6B is a box plot illustrating the lowest recorded mean arterial blood pressure (MABP; calculated as % of baseline) 30 minutes post LPS injection. A significant difference between SpN-T and sham group is shown; P=0.0296. FIG. 6C and 6D are box plots illustrating the TNFα (FIG. 6C) and IL-6 (FIG. 6D) concentrations at 0.5 hour post in vivo LPS injection.

DETAILED DESCRIPTION

The Neurostimulation Device

Figure 1:
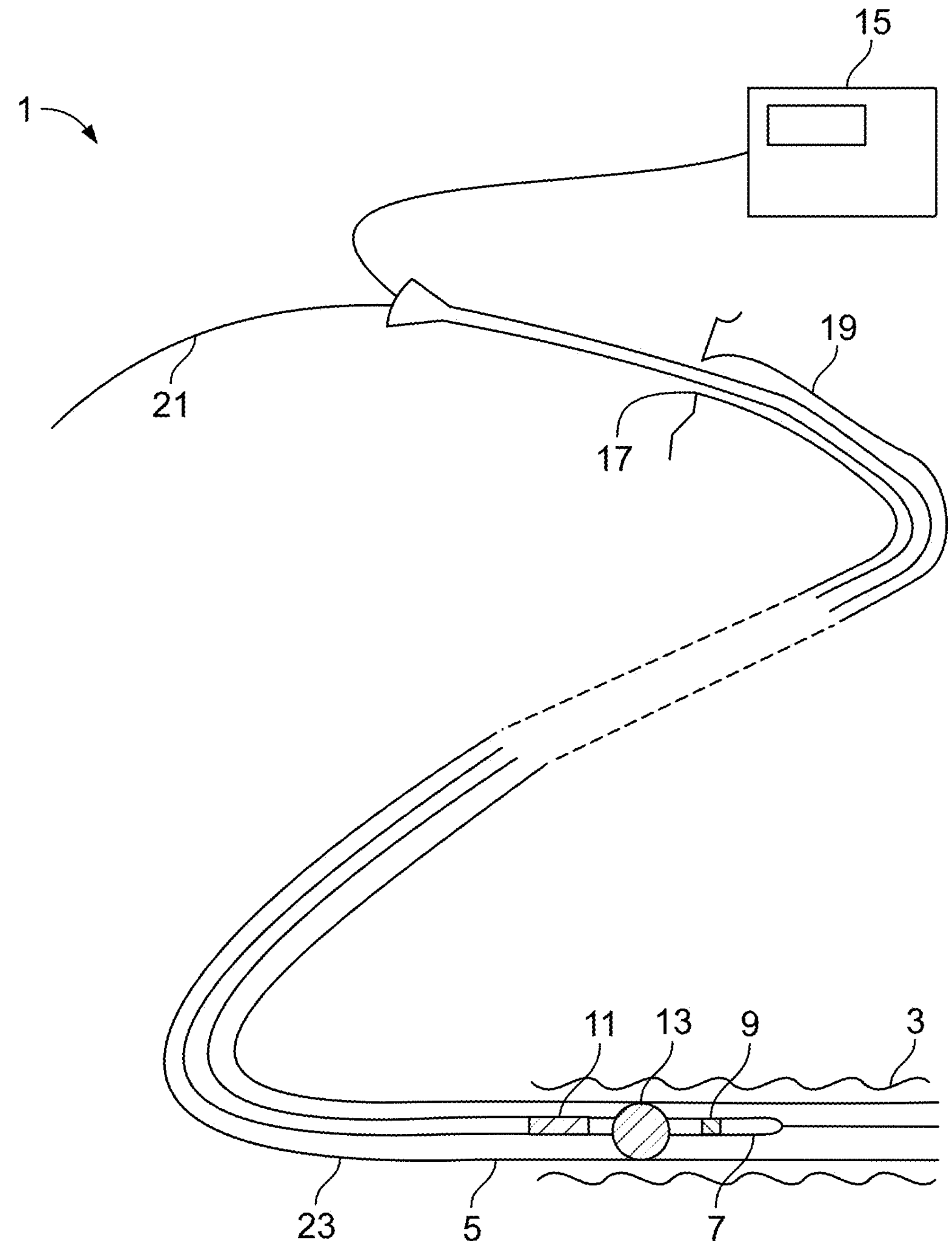
FIG. 1 illustrates an overview of a neurostimulation device in use.

Referring to FIG. 1, there is a neurostimulation device 1 for non-destructively stimulating neural activity in a nerve 3 (or nerve fibres) that are in proximity to a blood vessel 5. The nerve 3 may be wrapped around, or at least partially wrapped around, the blood vessel 5. Thus, when the neurostimulation device 1 is located within the blood vessel 5 the neurostimulation device 1 can electrically stimulate the nerve 3 through the wall of the blood vessel 5. The portion of the neurostimulation device 1 located within the blood vessel 5 may be referred to herein as the indwelling device.

In the following example, the nerve 3 is the splenic nerve (SpN) and the blood vessel 5 is the splenic artery (SpA). However, it will be appreciated that the neurostimulation devices that are the subject of this application could be used in conjunction with any suitable blood vessel 5 in order to apply an electrical signal to any corresponding nerve 3. Other examples include: the carotid artery and the vagus nerve and the cervical sympathetic ganglion; the aorta and the phrenic nerve, the vagus nerve, the superior mesenteric ganglion, and the inferior mesenteric ganglion; the renal artery and the renal nerves; and the subclavian artery and the brachial plexus; and common hepatic artery and its associated nerves; and gastroduodenal artery and its associated nerves; iliac artery and splanchnic nerves.

The neurostimulation device 1 comprises a catheter 7 with at least two electrodes 9, 11 arranged on the outside surface of the catheter 7. The electrode that is positioned closer to the distal end 25 of the catheter 7 is referred to as the distal electrode 9, and the electrode that is positioned closer to the proximal end the catheter 7 is referred to as the proximal electrode 11.

The distal end 25 of the catheter 7 is the first of the two ends that is introduced into the patient. The proximal end of the catheter 7 is the end that follows the distal end 25 along the length of the catheter 7. In this example, the catheter 7 is around 5 French (1.667 mm) in diameter which has been found to be an optimum diameter for positioning the catheter 7 in the splenic artery via the radial artery 19.

There is also an insulator 13 positioned in between the electrodes 9, 11, and attached to the catheter 7, which can assume a contracted configuration and an expanded configuration. The width (or diameter) of the insulator 13 in a direction perpendicular to the longitudinal axis of the blood vessel 5 is smaller in the contracted configuration in comparison to the expanded configuration.

In the contracted configuration, the size of the insulator 13 allows the catheter 7 to travel inside the blood vessel 5. In the contracted configuration the diameter (or width) of the insulator 13 is less than the diameter of the blood vessel 5 that the catheter 7 is travelling within.

In the expanded configuration, the size of the insulator 13 blocks blood flowing from the proximal electrode 11 to the distal electrode 9. The diameter (or width) of the insulator 13 in the expanded configuration is at least as large as, or larger than, the diameter of the blood vessel 5. Preferably, the diameter of the insulator 13 in the expanded configuration forces the surface of the insulator 13 to put pressure on the blood vessel wall in order to form a seal between the electrodes 9, 11 that blocks blood flowing between them.

In this example, the insulator 13 comprises a balloon that is made from an insulating material. Specifically, the surface of the insulator 13 does not conduct electricity. The balloon is filled with fluid in order to expand the diameter of the balloon to a size that will block the blood flow. The fluid maintains pressure inside the insulator 13, which in turn causes the outside surface of the insulator 13 to exert pressure on the inside wall of the blood vessel 5. The fluid can be evacuated from the balloon in order to contract the balloon. This reduces the pressure inside the balloon. Although a balloon has been used as a specific example of an insulator, any other suitable insulator could be used in order to block blood flow and to provide an insulating barrier between the electrodes 9, 11. For instance, an insulating disc could be used with mechanical levers within it that move to change the configuration of the insulator from a contracted configuration to an expanded configuration, and vice versa.

The neurostimulation device 1 also comprises a controller 15 that is configured to provide an electrical signal to the electrodes 9, 11, and thus may be referred to as a stimulator. The controller 15 is also configured to control the size of the insulator 13 by controlling the volume of fluid in the insulator 13 in order to move the insulator between its contracted and expanded configurations. Although the controller 15 in this example is configured to control stimulation and the size of the insulator 13, these functions could be carried out separately by independent controllers.

In order to place the portion of the catheter 7 comprising the electrodes 9, 11 and the insulator 13 inside the target blood vessel 5, firstly a surgeon makes an incision 17 in the wrist of the patient in order to access the radial artery 19. Once this opening has been created, an introducer is placed. Then, a guiding catheter is placed within the introducer to the aorta where the celiac artery takes off. A guidewire 21 is inserted into the radial artery 19 and fed through to the splenic artery 5. In this specific example, the guidewire 21 is around 300 cm in length, which has been found to be an optimum length for accessing the splenic artery 5 of a human patient in order to stimulate the splenic nerve 3.

Alternatively, the catheter 7, as described above, can be placed inside the target blood vessel via passage through the femoral artery. This inguinal approach requires the surgeon to make an incision in the groin of the patient to access the femoral artery. Once this opening has been created, an introducer is placed, and the catheter can be advanced through the introducer to celiac artery and finally to the splenic artery.

Once the guidewire 21 is positioned in the correct position in the splenic artery 5, the guiding catheter is removed or catheter 7 is fed over and along the guidewire 21. The catheter 7 has a central lumen into which the guidewire 21 is inserted. The catheter 7 is fed towards the distal end of the guidewire 21 until it is located in position in the splenic artery 5. In this example, the catheter 7 is around 130 cm in length, which has been found to be an optimum length for positioning the electrodes 9, 11 at the end of the catheter in the correct location.

Figure 2:
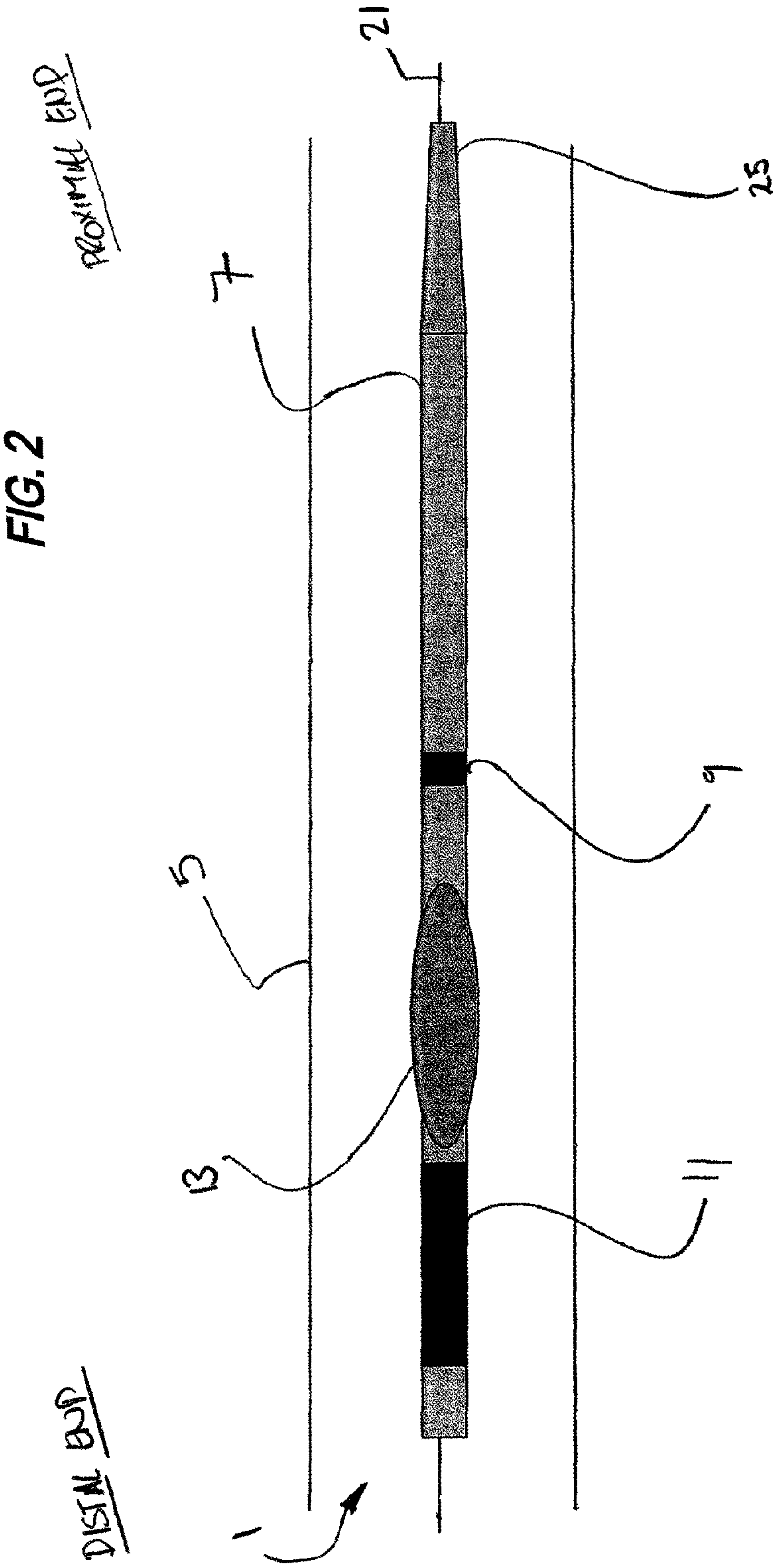
FIG. 2 illustrates an example of the neurostimulation device with an insulator in a contracted configuration.

FIG. 2 illustrates the neurostimulation device 1 with the insulator 13 in the contracted configuration. The contracted configuration allows the catheter 7 to travel within the blood vessel 5. This also allows blood to flow in the blood vessel 5 around the insulator 13 between the electrodes 9, 11. In the contracted configuration, the diameter of the insulator 13 may be around a similar size to that of the catheter 7. This prevents the insulator 13 from obstructing the movement of the catheter 7 along the inside of the blood vessel 5. The catheter 7 has a rounded distal end 25 that forms an atraumatic tip which helps to prevent the catheter 7 from damaging the blood vessel 5.

Figure 3:
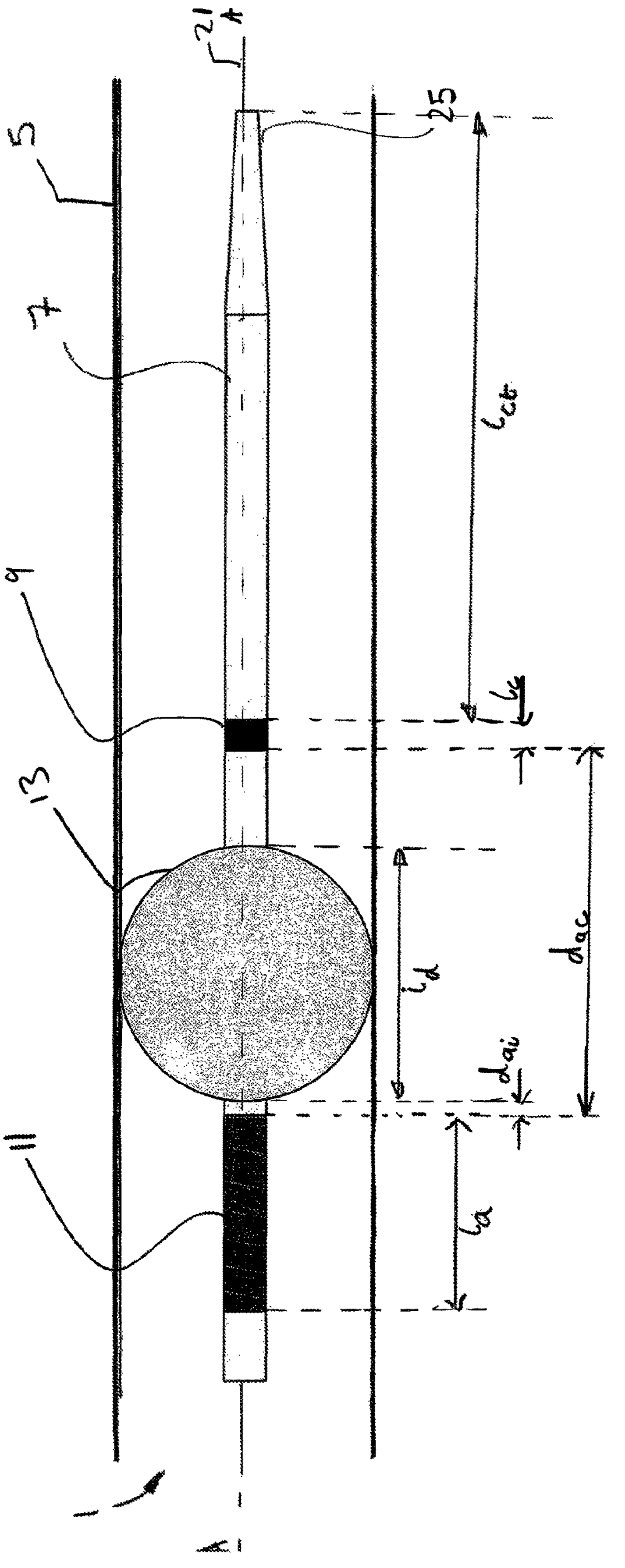
FIG. 3 illustrates an example of the neurostimulation device with an insulator in an expanded configuration.

FIG. 3 illustrates the neurostimulation device 1 with the insulator 13 in the expanded configuration. In order to change the configuration of the insulator 13 from the contracted configuration shown in FIG. 2 to the expanded configuration, the controller 15 forces fluid into the insulator 13 via a lumen in the catheter 7 that fluidly connects the insulator 13 with the controller 15. In the expanded configuration, the outside surface of the insulator 13 contacts an inner circumference of the blood vessel 5, thus forming an annular electrically insulating seal in the blood vessel 5. This annular seal prevents blood from flowing from one side of the insulator 13 to the other. This prevents blood from flowing from the proximal electrode 11 to the distal electrode 9 (or vice versa).

In the expanded configuration, the insulator 13 prevents the blood in the blood vessel 5 from providing a direct conductive channel between the electrodes 9, 11. Instead, the insulator 13 forces the electrical signal to follow a path from one of the electrodes, through the blocked blood nearest the electrode, into the blood vessel wall, through the blocked blood on the other side of the insulator 13 and to the other electrode. This path improves the ability of the neurostimulation device 1 to stimulate the nerve 3 surrounding the blood vessel 5, rather than allowing the electrical signals to dissipate within the blood flowing in the vessel 5. In addition, this arrangement helps to mitigate variations in current flow from disrupting the electrical signal, since the movement of blood flow is reduced by the insulator 13 blocking the blood flow.

The insulator 13 in its expanded configuration also helps to keep the electrodes 9, 11 in close proximity to the longitudinal axis of the blood vessel ("A"). In this way, the electrodes 9, 11 can be prevented from touching the wall of the blood vessel 5. These effects assist in maintaining the distance between each one of the electrodes 9, 11 and the blood vessel wall equal around the inner circumference of the vessel 5. In this way, the stimulation provided between the electrodes 9, 11 can follow an equal path at all points around the inner circumference of the vessel 5. This helps to stimulate the nerve 3 evenly around the blood vessel 5.

In this example, the insulator 13 is positioned closer to the proximal electrode 11 than it is to the distal electrode 9, which helps to maintain the proximal electrode 11 in a central position. This is particularly important when the proximal electrode 11 is longer than the distal electrode 9 which has been found to improve performance especially when the proximal electrode 11 is an anode and the distal electrode 9 is a cathode.

In order to maintain the distal electrode 9 in a central location away from the blood vessel wall, the distal electrode 9 is offset from the distal end 25 of the catheter 7 by a distance, $l_{ct}$. Thus, there is an insulating portion between the distal end 25 of the catheter 7 and the distal electrode 9. Therefore, even if the distal end 25 of the catheter 7 moves towards the blood vessel wall, the blood vessel wall will contact the insulating portion instead of the distal electrode 9. By contrast, if the distal electrode 9 were positioned at the distal end 25 of the catheter 7 this would increase the risk of the distal electrode 9 touching the blood vessel wall. The distal electrode 9 has a length denoted $l_c$. This length could be decreased with alternate electrode materials/coatings to permit higher stimulation voltages; or could be increased with high current amplitude neurostimulators, to a maximum of 5 cm to maintain spatial selectivity.

A number of dimensions of the neurostimulation device 1 are illustrated in FIG. 3. The length of the proximal electrode 11 (e.g. the anode), $l_a$, is the distance between the proximal end of the proximal electrode 11 and its distal end. It has been found that a proximal electrode 11 of length around 10 mm improves the stimulation of neural activity in the nerve 3.

The distance between the distal end of the proximal electrode 11 and the proximal end of the insulator 13, $d_{ai}$, is the gap between the proximal electrode 11 and the insulator 13. It has been found that a gap of around 2 mm is the closest that the insulator 13 can be brought to the proximal electrode 11 without interfering with the structure of the neurostimulation device 1. Bringing the insulator 13 as close as possible to the proximal electrode 11 helps to maintain the proximal electrode 11 centrally with respect to the blood vessel 5.

The diameter of the insulator 13, $i_d$, is the width of the insulator 13 measured in a direction perpendicular to the longitudinal axis of the blood vessel 5. It has been found that a diameter of around 12 mm helps to effectively block blood flow in the blood vessel 5 (e.g. the splenic artery).

The distance between the distal end of the proximal electrode 11 and the proximal end of the distal electrode 9, $d_{ac}$, is the gap between the proximal electrode 11 and the distal electrode 9. In order to improve the stimulation of neural activity in the nerve 3 it has been found that the minimum gap between the electrodes 9, 11 may be 15 mm, the maximum gap may be 20 mm. The gap of 20 mm avoids stimulating muscles and causing fasciculations. It has been found that a gap between the electrodes 9, 11 of around 2 cm provides optimum stimulation.

Any one of the electrodes 9, 11, or both of the electrodes 9, 11, may be formed from a platinum-iridium alloy. The ratio of platinum to iridium may be as low as 80:20. Any one of the electrodes 9, 11, or both of the electrodes 9, 11 may be any conductive material coated in Titanium Nitride, or Iridium Oxide or poly-3,4-ethylenedioxythiophene (PEDOT). Any one of the electrodes 9, 11, or both of the electrodes 9, 11, may comprise a conductive ribbon wound around the catheter 7. These materials have been found to provide optimum stimulation of the nerve 3.

Figure 4:
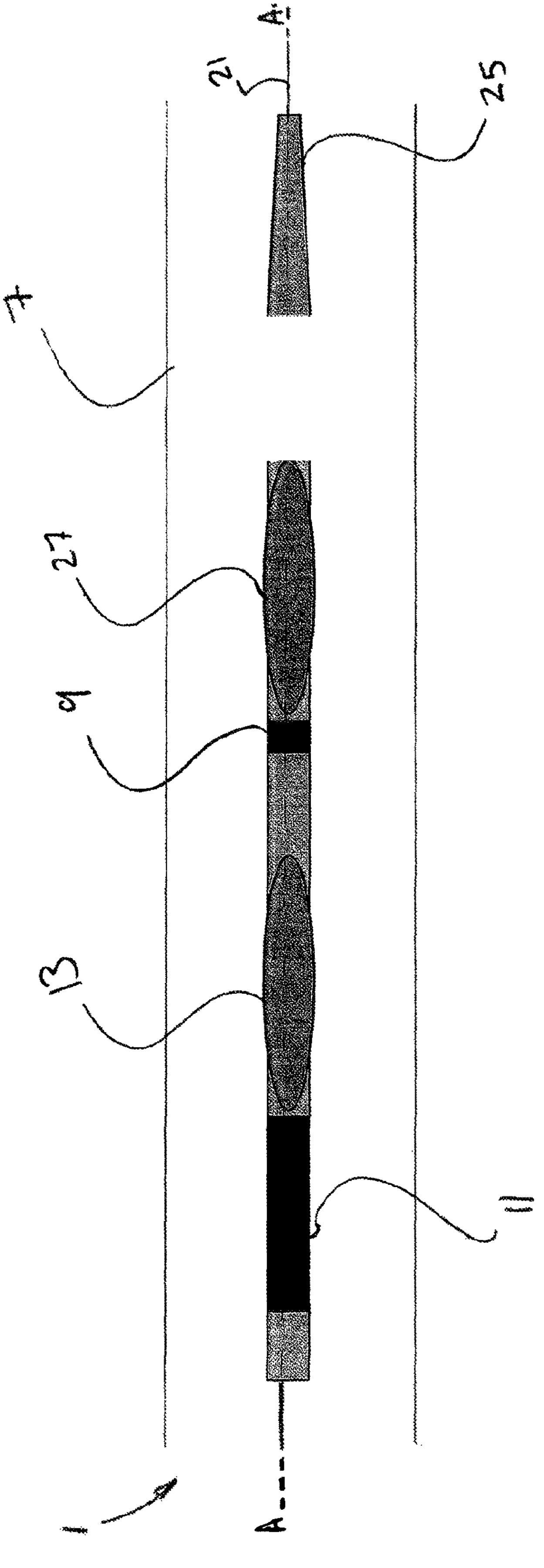
FIG. 4 illustrates another example of a neurostimulation device with two insulators in a contracted configuration.
Figure 5:
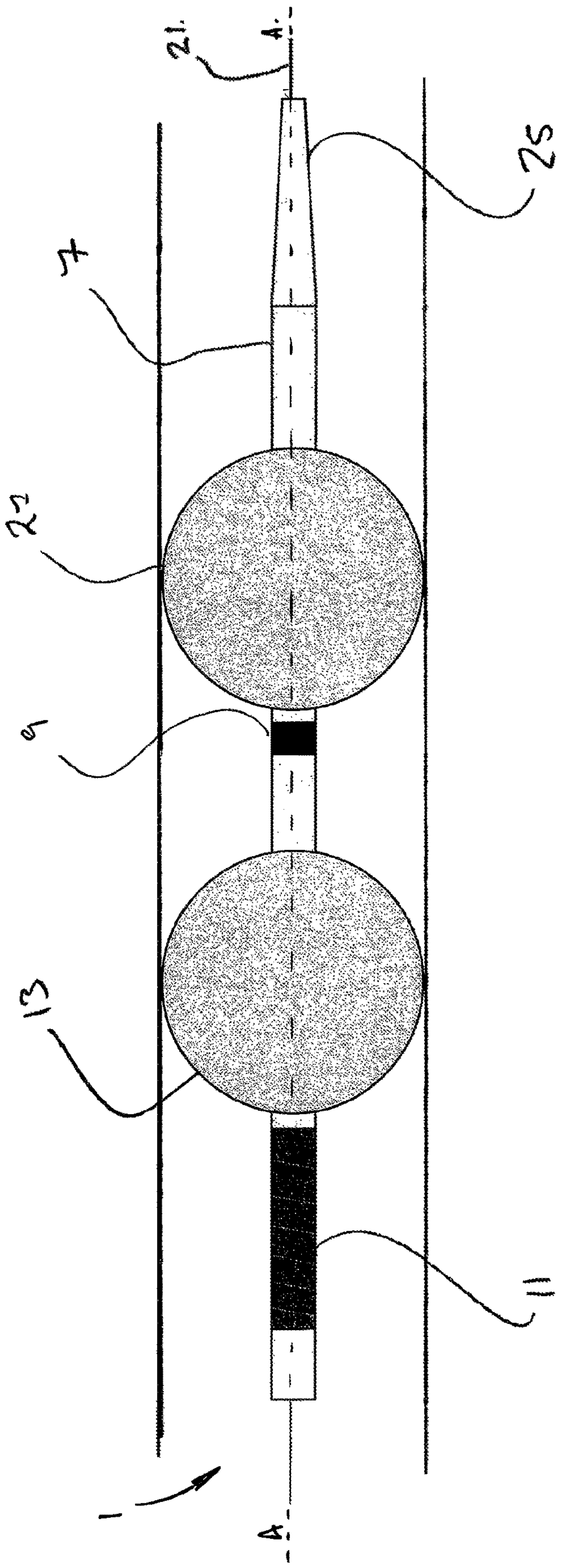
FIG. 5 illustrates an example of the neurostimulation device of FIG. 4 with the two insulators in an expanded configuration.

Referring to FIGS. 4 and 5, there is another example of a neurostimulation device 1. This device 1 is similar to that as described with reference to FIGS. 1 to 3; however, this device 1 comprises a second insulator 27 that is positioned distally of the distal electrode 9—between the distal end 25 of the catheter 7 and the distal electrode 9. The second insulator 27 is positioned over the insulating portion discussed above. The second insulator 27 operates in a similar manner to the first insulator 13 in that the second insulator 27 has a contracted configuration for allowing the catheter 7 to travel in the blood vessel 5 and an expanded configuration that blocks blood flowing in the blood vessel 5. The second insulator 27 blocks blood from flowing between the distal electrode 9 and the distal end 25 of the catheter 7 in a similar manner to that described with reference to the first insulator 13.

The role of the second insulator 27 is to block blood flow more effectively. This is achieved since an additional barrier is created distally of the distal electrode 9 in this arrangement. In addition, the second insulator 27 helps to maintain the distal electrode 9 in a central location within the bore of the blood vessel 5, as described above for the first insulator 13.

The insulators 13, 27 may be operated simultaneously by the controller 15. For instance, the insulators 13, 27 may be fluidly connected to one another by the lumen that is connected to the controller 15. Thus, the insulators 13, 27 will expand and contract in tandem with one another. In other words, when the first insulator 13 is in the contracted configuration the second insulator 27 will be in the contracted configuration also, and when the first insulator 13 is in the expanded configuration the second insulator 27 will be in the expanded configuration also.

In another example, the insulators 13, 27 may be operated independently from one another by the controller 15, or by separate controllers. For instance, the insulators 13, 27 may not be fluidly connected to one another, and each insulator 13, 27 may have a separate lumen through which fluid can be passed. Thus, the insulators 13, 27 can expand and contract independently of one another, or in tandem with one another. In other words, when the first insulator 13 is in the contracted configuration the second insulator 27 can be in the expanded configuration, and when the first insulator 13 is in the expanded configuration the second insulator 27 can be in the contracted configuration.

Use in Therapy

Acute Medical Conditions

The neurostimulation devices described herein may be useful in treating acute medical conditions. Acute medical conditions, as referred to herein, refer to a rapid deterioration in a subject's physiological status that may be life threatening if left untreated. Examples of acute medical conditions include trauma, sepsis, hemorrhage, severe hemophilia, severe episodes of lupus, severe episodes of multiple sclerosis, Fulminant type 1 diabetes, episodes of severe Crohn's, allograph/autograph rejection, anaphylaxis, and shock, e.g. endotoxic shock. These subjects therefore require urgent medical care to relieve suffering and minimize morbidity and mortality risk. Advantageously, the subject to be treated is a human.

As illustrated in the examples, the inventors have shown that neuromodulation of the nerves supplying the spleen, in particular the nerves surrounding the splenic artery (referred to herein as splenic arterial nerves), increased the survival of animals in an endotoxemic (LPS) shock model. In particular, the inventors found that applying an electrical signal to the splenic nerves stabilized blood pressure, which drops dramatically in LPS-treated animals. Such electrical signals reduced the maximum reduction in blood pressure. In particular, the inventors have shown that a highly advantageous response can be achieved by using a neurostimulation device as described herein. Thus, the neurostimulation device of the invention (i.e. an "intravascular" neurostimulation device) may be particularly useful for treating life-threatening conditions, such as those having physiological changes associated with shock and cardiovascular dysfunction (e.g. trauma, haemorrhaging and shock, e.g. septic shock).

Thus, an aspect of the invention provides a method of stimulating neural activity in a nerve supplying the spleen to modulate systemic arterial blood pressure and/or central venous pressure in a subject, the method comprising: providing a neurostimulation device comprising a catheter or stent for insertion into a splenic artery and at least one electrode associated with the catheter or stent; inserting a distal end of the catheter or stent into a splenic artery of the subject; positioning the at least one electrode of the neurostimulation device within the splenic artery in proximity to a splenic arterial nerve associated with the splenic artery; and controlling the operation of the at least one electrode with at least one controller to apply an electrical signal to the nerve to stimulate neural activity therein. In some embodiments, the method is for the treatment of an acute medical condition, such as trauma, haemorrhaging, or shock, e.g., septic shock. It is noted that for a stent, the distal end of the stent is considered to be the end positioned closer to the spleen, whilst the proximal end is the end positioned closer to the midline.

Another aspect of the invention provides an electrical signal for use in a method of treating an acute medical condition in a subject, wherein the electrical signal is provided by or obtained from a neurostimulation device, said device comprising a catheter or stent for insertion into a splenic artery and at least one electrode associated with the catheter or stent.

In some embodiments, the neurostimulation device comprises a proximal electrode offset from a distal electrode along a length of the catheter. In some embodiments in which the indwelling device is a catheter, the neurostimulation device further comprises an insulator positioned between the proximal electrode and the distal electrode on the catheter. In some such embodiments, the insulator comprises an expanded configuration in which the insulator blocks, when in use, blood flowing through the splenic artery between the proximal electrode and the distal electrode. In some such embodiments, the neurostimulation device further comprises a stimulator arranged to apply an electrical signal between the proximal electrode and the distal electrode, wherein the stimulator is arranged to apply an electrical signal when the insulator is in the expanded configuration, thus inducing electrical activity in a wall portion of the splenic artery between the proximal and distal electrodes. In some such embodiments, the neurostimulation device further comprises an insulation portion between the distal electrode and a distal end of the catheter for offsetting the distal electrode from a wall of the splenic artery.

In certain particular embodiments, the indwelling device is a catheter and the neurostimulation device comprises a proximal electrode offset from a distal electrode along a length of the catheter; an insulator positioned between the proximal electrode and the distal electrode on the catheter; the insulator having a contracted configuration in which the size of the insulator allows the catheter to travel inside the blood vessel; the insulator having an expanded configuration in which the insulator blocks blood flowing through the blood vessel between the proximal electrode and the distal electrode; a stimulator arranged to apply an electrical signal between the proximal electrode and the distal electrode when the insulator is in the expanded configuration, thus inducing electrical activity in a wall portion of the blood vessel between the proximal and distal electrodes; and an insulation portion between the distal electrode and a distal end of the catheter for offsetting the distal electrode from a wall of the blood vessel.

In further embodiments, the neurostimulation device may comprise any of the additional features described herein.

Examples of acute medical conditions in which the use of the neurostimulation device of the invention may be beneficial include trauma, sepsis, hemorrhage, severe hemophilia, severe episodes of lupus, severe episodes of multiple sclerosis, Fulminant type 1 diabetes, episodes of severe Crohn's, allograph/autograph rejection, anaphylaxis, and shock, e.g., septic shock or endotoxic shock.

Trauma includes, for example, physical injuries caused by an external source, such as blunt trauma (including motor vehicle collisions, falls, head injuries, lacerations), penetrating trauma (such as cuts, stab wounds, impalements), blast injury, burns (caused by heat, cold, electricity, chemicals, friction or radiation) and combinations thereof.

Hemorrhaging is a loss of blood from the circulatory system. Hemorrhaging includes, for example, hematemesis (vomiting fresh blood), hemoptysis (coughing up blood from the lungs), hematuria, cerebral hemorrhage, pulmonary hemorrhage, postpartum hemorrhage and gastrointestinal bleeds. Hemorrhaging may result from, for example, traumatic injury or an underlying medical condition. Hemorrhaging also includes inter-operative hemorrhage and post-operative hemorrhage.

Shock includes, for example, septic shock, anaphylactic shock, toxic shock syndrome, cardiogenic shock, hypovolemic shock and neurogenic shock. The invention is particularly useful in treating septic shock.

The invention is of particular interest in relation to trauma, septic shock, hemorrhage, severe hemophilia, severe episodes of lupus, severe episodes of multiple sclerosis, Fulminant type 1 diabetes, episodes of severe Crohn's, allograph/graph rejection, anaphylaxis, and endotoxic shock.

Treatment of a disease, disorder or condition in a subject can be assessed, measured or confirmed in various ways, but typically involves determining an improvement in one or more physiological parameters or symptoms of the subject. As used herein, an "improvement" in a physiological parameter is taken to mean a change in the value of that parameter in the subject towards the normal value or normal range for that value—i.e. towards the expected value in a healthy subject.

As used herein, "worsening" of a determined physiological parameter is taken to mean a change in the value of that parameter in the subject away from the normal value or normal range for that value —i.e. away from the expected value in a healthy subject.

For example, an acute medical condition may be accompanied by a drop in blood pressure, dizziness or light-headedness, a rash, nausea, muscle pain, shortness of breath, oliguria, muscle pain, and cold, clammy and pale or mottled skin The body's vital signs are particularly useful for assessing acute medical conditions as these are signs that indicate the status of the body's vital (life-sustaining) functions. A vital sign may be one or more of the group consisting of: systemic arterial pressure, body temperature, heart rate, breathing rate, oxygen saturation, and pain sensation.

Other useful physiological parameters may be systemic venous pressure, pulmonary artery pressure (also referred to herein as pulmonary pressure), hourly urine output, the level of consciousness, arterial partial pressure of oxygen and arterial partial pressure of carbon dioxide.

Any one or a combination of the physiological parameters may be useful in the context of the invention, e.g. for assessing treatment of a subject. A particularly useful parameter in the context of the invention is systemic arterial pressure.

In a subject having an acute medical condition, an improvement in a physiological parameter that is indicative of treatment of the acute medical condition may (depending on which abnormal values a subject is exhibiting) be one or more of the group consisting of: restoring the body temperature to between 36° C. and 38° C., restoring the heart rate to 60-100 bpm, restoring the systemic arterial pressure to between 90/60 mmHg and 150/90 mmHg, restoring the systemic venous pressure to about 5 mmHg in the right atrium and about 8 mmHg in the left atrium, restoring the central venous pressure to be in the range of about 2-8 mmHg, restoring the pulmonary pressure to about 15 mmHg, restoring the breathing rate to 8-14 breaths per minute, an increase in oxygen saturation to ≥94%, an increase the arterial partial pressure of oxygen to 12-15 kPa, restoring the arterial partial pressure of carbon dioxide to 4.4-6.1 kPa, a reduction of pain sensation, restoring urine output to ≥0.5 ml/kg/hr, an increase in the level of consciousness, a reduction in the level of lactate, a change in the level of blood glucose, a change in the level of base deficit in blood and a change in the level of arterial pH. The invention might not lead to a change in all of these physiological parameters.

In some embodiments, the invention aims to restore the blood pressure (e.g. systemic arterial pressure, systemic venous pressure, central venous pressure and pulmonary pressure) in the subject to the normal range. As would be known to the skilled person, when referring to blood pressure in the art, it generally refers to the arterial pressure in the systemic circulation (i.e. systemic arterial pressure), unless otherwise specified. Normal systemic arterial pressure in a healthy human adult is considered to be between 90/60 mmHg and 150/90 mmHg Systemic arterial pressure values below this range may indicate that the individual is suffering from shock. In some embodiments, the invention aims to restore systemic arterial pressure in the subject to the normal range. Hence, when a subject is suffering from shock, the invention aims to increase the systemic arterial pressure in the subject.

Determining the systemic venous pressure, central venous pressure and the pulmonary pressure may also be useful in the context of the invention, e.g. for assessing treatment (suitable nerve target engagement). Determining these pressures usually requires tools, such as a catheter. However pulmonary pressure may be determined using ultrasound measurements, for example, of the diameter of the inferior vena cava and the apparent cardiac filling pressure. The normal range of systemic venous pressure in a healthy human adult is usually 5 mmHg in the right atrium and 8 mmHg in the left atrium. The normal range of central venous pressure in a healthy human adult is considered to be in the range of about 2-8 mmHg. The normal range of the pulmonary pressure in a healthy adult is usually about 15 mmHg at rest.

In some embodiments, the invention aims to restore the body temperature of the subject to the normal range for a healthy human adult, i.e. between 36° C. and 38° C.

A normal resting heart rate for a healthy human adult is 60-100 bpm, but in acute medical conditions, the heart rate is typically increased. In some embodiments, the invention aims to restore the heart rate of the subject to the normal range, e.g. it aims to reduce the heart rate.

A normal breathing rate for a healthy human adult is 8-14 breaths per minute. In some embodiments, the invention aims to restore the breathing rate of the subject to the normal range.

Healthy individuals at sea level usually exhibit oxygen saturation ($SO_2$) values between 96% and 99%, and are usually above 94%. If the level is below 90%, it is considered low resulting in hypoxemia. Blood oxygen levels below 80% may compromise organ function, such as the brain and heart. Continued low oxygen levels may lead to respiratory or cardiac arrest. Oxygen saturation is commonly measured using pulse oximetry. In some embodiments, the invention aims to restore the oxygen saturation level in a subject to normal values.

The normal range of arterial partial pressure of oxygen in a healthy human adult is usually 12-15 kPa. The normal range of arterial partial pressure of carbon dioxide in a healthy human adult is 4.4-6.1 kPa. In some embodiments, the invention aims to restore the arterial partial pressure of oxygen and/or the arterial partial pressure of carbon dioxide in the subject to the normal range.

The normal urine output for a healthy human adult is 0.5-1 ml/kg/hr. This roughly equates to 30-60 ml per hour in an average sized adult. In some embodiments, the invention aims to restore the urine output of the subject to the normal range.

Further physiological parameters that are useful in the context of the invention include the level of lactate, blood glucose, base deficit in blood and arterial pH. These parameters can be determined by biochemical analyses.

Suitable methods for determining the value for any given parameter would be appreciated by the skilled person.

The skilled person will appreciate that the baseline for any physiological parameter in a subject need not be a fixed or specific value, but rather can fluctuate within a normal range or may be an average value with associated error and confidence intervals. For example, the normal ranges for a person's vital signs vary with age, weight, gender, and overall health. Suitable methods for determining baseline values are well known to the skilled person.

As used herein, a physiological parameter is determined in a subject when the value for that parameter exhibited by the subject at the time of detection is determined. A detector (e.g. a physiological sensor subsystem, a physiological data processing module, a physiological sensor, etc.) is any element able to make such a determination. Detecting any of the physiological parameters may be done before, during and/or after modulation of neural activity in the nerve that is stimulated in accordance with the invention. Detection can be performed manually by a human (e.g. a clinician or caregiver), with or without the use of a detector, such as an instrument, which together with the neurostimulation device provides a system of the invention. Alternatively, the detector that is used does not form part of the system of the invention. Where a device or detector is used, detection can be performed autonomously.

Thus, in certain embodiments, the invention further comprises a step of determining one or more physiological parameters of the subject, wherein the signal that is provided by the neurostimulation device is applied only when the determined physiological parameter meets or exceeds a predefined threshold value. In such embodiments wherein more than one physiological parameter of the subject is determined, the signal may be applied when any one of the determined physiological parameters meets or exceeds its threshold value, alternatively only when all of the determined physiological parameters meet or exceed their threshold values. In certain embodiments wherein the signal is applied by a system of the invention, the system further comprises at least one detector configured to determine the one or more physiological parameters of the subject.

When addressing the severity of shock and the response to a medical treatment for shock, one important factor is tissue perfusion, which may be increased during episodes of shock. Tissue perfusion may be associated with a decrease in blood pressure and a number of other changes in physiological parameters including the level of lactate and to a lesser extent base deficit and arterial pH, which some embodiments of the invention seek to restore to normal levels, as described above.

A predefined threshold value for a physiological parameter is the minimum (or maximum) value for that parameter that must be exhibited by a subject before the specified intervention is applied. For any given parameter, the threshold value may be defined as a value indicative of a pathological state or a disease state. The threshold value may be defined as a value indicative of the onset of a pathological state or a disease state. Appropriate threshold values for any given physiological parameter can be simply determined by the skilled person, for example, with reference to medical standards of practice.

Such a threshold value for a given physiological parameter is exceeded if the value exhibited by the subject is beyond the threshold value—that is, the exhibited value is a greater departure from the normal or healthy value for that physiological parameter than the predefined threshold value.

A subject of the invention may, in addition to receiving neuromodulation of a splenic nerve according to the invention, receive other treatments and/or medicines for the disease, disorder or condition. For example, the subject may receive fluids given into a vein, antibiotics (e.g. penicillin, cephalosporin, tetracycline, macrolide, or fluoroquinolones) given into a vein, a medicine that increases blood pressure and/or blood flow to tissues and organs, surgery to remove the source of an infection (such as an abscess) and any tissue that has been badly damaged by the infection, oxygen given through a face mask, a cannula in the nose, or a tube passed down the throat into the trachea connected to a breathing machine (ventilator) if there is severe difficulty with breathing.

The subject may receive an anti-inflammatory medicine (which will usually be any medication which was occurring before application of the neurostimulation device of the invention). Such medicines include e.g., nonsteroidal anti-inflammatory drugs (NSAIDs), steroids, 5ASAs, disease-modifying-anti-inflammatory drugs (DMARDs) such as azathioprine, methotrexate, cyclosporin, biological drugs such as infliximab and adalimumab, and oral DMARDs such as Jak inhibitors.

Thus, in certain embodiments of the invention, these treatments and/or medicines are used in combination with (e.g., concomitantly with, simultaneously with, or subsequently to) the use of a neurostimulation device of the invention. In the methods of the invention, anticoagulant therapy, e.g. with heparin, may be administered to the subject prior to, following, and/or simultaneously with the application of the neurostimulation device of the invention.

Disorders Associated with Inflammation

The neurostimulation devices that are described herein may be used in the treatment of inflammation, of an inflammatory disorder, or of a disease, disorder or condition associated with inflammation. Diseases, disorders or conditions associated with inflammation typically present with an imbalance of pro- and anti-inflammatory cytokine profiles as compared to the physiological homeostatic state, e.g. increased pro-inflammatory cytokine levels and/or decreased anti-inflammatory cytokine levels. The inventors have shown that applying an electrical signal to the splenic arterial nerve using a neurostimulation device of the invention induces a similar physiological response to that which is achieved when using an extravascular neurostimulation device. In this regard, the inventors have shown that the electrical signal applied by the extravascular neurostimulation device induces a beneficial cytokine response in the context of the treatment of inflammation, e.g. inflammatory disorders, or diseases, disorders or conditions associated with inflammation. It therefore follows that the neurostimulation device of the invention (i.e. an "intravascular" neurostimulation device) is similarly effective in such treatment. The invention may be useful in the treatment of acute inflammatory episodes associated with medical conditions.

Thus, an aspect of the invention provides a method of stimulating neural activity in a nerve supplying the spleen so as to modulate an inflammatory response in a subject, the method comprising: providing a neurostimulation device comprising a catheter or stent for insertion into a splenic artery and at least one electrode associated with the catheter or stent; inserting a distal end of the catheter or stent into a splenic artery of the subject; positioning the at least one electrode of the neurostimulation device in the artery in proximity to a splenic arterial nerve associated with the splenic artery; and controlling the operation of the at least one electrode with at least one controller to apply an electrical signal to the nerve to stimulate neural activity therein. In some embodiments, the method is for the treatment of inflammation, an inflammatory disorder, or a disease, disorder or condition associated with inflammation.

In another aspect, the invention provides an electrical signal for use in a method of treating inflammation, an inflammatory disorder, or a disease, disorder or condition associated with inflammation, wherein the electrical signal is provided by or obtained from a neurostimulation device, and wherein said device comprises a catheter or stent for insertion into a splenic artery and at least one electrode associated with the catheter or stent.

Advantageously, the subject to be treated is a human. Such a human subject may be suffering from or at risk of developing inflammation, an inflammatory disorder, or a disease, disorder or condition associated with inflammation.

In some embodiments, the indwelling device is a catheter. In some such embodiments, the neurostimulation device comprises a proximal electrode offset from a distal electrode along a length of the catheter. In some such embodiments, the neurostimulation device further comprises an insulator positioned between the proximal electrode and the distal electrode on the catheter. In some such embodiments, the insulator comprises an expanded configuration in which the insulator blocks, when in use, blood flowing through the splenic artery between the proximal electrode and the distal electrode. In some such embodiments, the neurostimulation device further comprises a stimulator arranged to apply an electrical signal between the proximal electrode and the distal electrode, wherein the stimulator is arranged to apply an electrical signal when the insulator is in the expanded configuration, thus inducing electrical activity in a wall portion of the splenic artery between the proximal and distal electrodes. In some such embodiments, the neurostimulation device further comprises an insulation portion between the distal electrode and a distal end of the catheter for offsetting the distal electrode from a wall of the splenic artery.

In certain particular embodiments, the indwelling device is a catheter and the neurostimulation device comprises a proximal electrode offset from a distal electrode along a length of the catheter; an insulator positioned between the proximal electrode and the distal electrode on the catheter; the insulator having a contracted configuration in which the size of the insulator allows the catheter to travel inside the blood vessel; the insulator having an expanded configuration in which the insulator blocks blood flowing through the blood vessel between the proximal electrode and the distal electrode; a stimulator arranged to apply an electrical signal between the proximal electrode and the distal electrode when the insulator is in the expanded configuration, thus inducing electrical activity in a wall portion of the blood vessel between the proximal and distal electrodes; and an insulation portion between the distal electrode and a distal end of the catheter for offsetting the distal electrode from a wall of the blood vessel.

The invention is useful for treating subjects who are suffering from, or who are at risk of developing, diseases, disorders or conditions associated with inflammation, e.g. inflammatory disorders, e.g., autoimmune disorders. The invention may treat or ameliorate the effects of such diseases, disorders or conditions by reducing inflammation. This may be achieved by decreasing the production and release of pro-inflammatory cytokines, and/or by increasing the production and release of anti-inflammatory cytokines and pro-resolving molecules, from the spleen, by electrically stimulating the splenic arterial nerve as described herein.

Inflammatory disorders include autoimmune disorders, such as arthritis (e.g. rheumatoid arthritis, osteoarthritis, psoriatic arthritis), Grave's disease, myasthenia gravis, thryoiditis, systemic lupus erythematosus, Goodpasture's syndrome, Behcets's syndrome, allograft rejection, graft-versus-host disease, ankylosing spondylitis, Berger's disease, diabetes including Type I diabetes, Reitier's syndrome, spondyloarthropathy psoriasis, multiple sclerosis, Inflammatory Bowel Disease, Crohn's disease, Addison's disease, autoimmune mediated hair loss (e.g., alopecia areata) and ulcerative colitis.

Certain examples of inflammatory disorders include diseases involving the gastrointestinal tract and associated tissues, such as appendicitis, peptic, gastric and duodenal ulcers, peritonitis, pancreatitis, ulcerative, pseudomembranous, acute and ischemic colitis, inflammatory bowel disease, diverticulitis, cholangitis, cholecystitis, Crohn's disease, Whipple's disease, hepatitis, abdominal obstruction, volvulus, post-operative ileus, ileus, celiac disease, obesity, periodontal disease, pernicious anemia, amebiasis and enteritis.

Examples of inflammatory disease, disorders or conditions affecting the bones, joints, muscles and connective tissues include the various arthritides and arthralgias, osteomyelitis, gout, periodontal disease, rheumatoid arthritis, spondyloarthropathy, ankylosing spondylitis and synovitis.

Further examples include systemic or local inflammatory diseases and conditions, such as asthma, allergy, anaphylactic shock, immune complex disease, sepsis, septicemia, endotoxic shock, eosinophilic granuloma, granulomatosis, organ ischemia, reperfusion injury, organ necrosis, hay fever, cachexia, hyperexia, septic abortion, HIV infection, herpes infection, organ transplant rejection, disseminated bacteremia, Dengue fever, malaria and sarcoidosis.

Other examples include diseases involving the urogential system and associated tissues, such as diseases that include epididymitis, vaginitis, orchitis, urinary tract infection, kidney stone, prostatitis, urethritis, pelvic inflammatory bowel disease, contrast induced nephropathy, reperfusion kidney injury, acute kidney injury, infected kidney stone, herpes infection, and candidiasis.

Other examples include involving the respiratory system and associated tissues, such as bronchitis, asthma, hay fever, ventilator associated lung injury, cystic fibrosis, adult respiratory distress syndrome, pneumonitis, alvealitis, epiglottitis, rhinitis, achlasia, respiratory syncytial virus, pharyngitis, sinusitis, pneumonitis, alvealitis, influenza, pulmonary embolism, hyatid cysts and/or bronchiolitis.

Further examples are dermatological diseases and conditions of the skin (such as burns, dermatitis, dermatomyositis, burns, cellulitis, abscess, contact dermatitis, dermatomyositis, warts, wheal, sunburn, urticaria warts, and wheals); diseases involving the cardiovascular system and associated tissues, (such as myocardial infarction, cardiac tamponade, vasulitis, aortic dissection, coronary artery disease, peripheral vascular disease, aortic abdominal aneurysm, angiitis, endocarditis, arteritis, atherosclerosis, thrombophlebitis, pericarditis, myocarditis, myocardial ischemia, congestive heart failure, periarteritis nodosa, and rheumatic fever, filariasis thrombophlebitis, deep vein thrombosis); as well as various cancers, tumors and proliferative disorders (such as Hodgkin's disease), nosocomial infection; and, in any case the inflammatory or immune host response to any primary disease.

Other examples of inflammatory disorders include diseases involving the central or peripheral nervous system and associated tissues, such as Alzheimer's disease, depression, multiple sclerosis, cerebral infarction, cerebral embolism, carotid artery disease, obesity, concussion, subdural hematoma, epidural hematoma, transient ischemic attack, temporal arteritis, spinal cord injury without radiological finding (SCIWORA), cord compression, meningitis, encephalitis, cardiac arrest, Guillain-Barre, spinal cord injury, cerebral venous thrombosis and paralysis.

Inflammatory disorders also include conditions associated with immune or inflammatory response (i.e. acute inflammatory episodes) include injury to nerves or other tissue and pain associated with nerve or other tissue. Injury may be due to a physical, chemical or mechanical trauma. Non-limiting examples of injury include acute trauma, burn, whiplash, musculoskeletal strains, and post-operative surgery complications, such as DVT, cardiac dysrhythmia, ventilator associated lung injury, and post-operative ileus.

Conditions associated with a particular organ such as eye or ear may also include an immune or inflammatory response such as conjunctivitis, iritis, glaucoma, episcleritis, acute retinal occlusion, rupture globe, otitis media, otitis externa, uveitis and Meniere's disease.

Another example of an inflammatory disorder is post-operative ileus (POI). POI is experienced by the vast majority of patients undergoing abdominal surgery. POI is characterized by transient impairment of gastro-intestinal (GI) function along the GI tract as well pain and discomfort to the patient and increased hospitalization costs.

The impairment of GI function is not limited to the site of surgery, for example, patients undergoing laparotomy can experience colonic or ruminal dysfunction. POI is at least in part mediated by enhanced levels of pro-inflammatory cytokines and infiltration of leukocytes at the surgical site. Neural inhibitory pathways activated in response to inflammation contribute to the paralysis of secondary GI organs distal to the site of surgery. Stimulation of neural activity as taught herein may thus be effective in the treatment or prevention of POI.

The invention is particularly useful in treating autoimmune disorders (e.g. rheumatoid arthritis, osteoarthritis, psoriatic arthritis, spondyloarthropathy, ankylosing spondylitis, psoriasis, systemic lupus erythematosus (SLE), multiple sclerosis, Inflammatory Bowel Disease, Crohn's disease, and ulcerative colitis) and sepsis.

This invention is particularly useful for treating B cell mediated autoimmune disorders (e.g. systemic lupus erythematosus (SLE) and rheumatoid arthritis (RA)).

The invention is particularly useful for treating inflammatory conditions associated with bacterial infections. For example, the invention is particularly useful for treating inflammatory conditions caused or exacerbated by *Escherichia coli*, Staphylococcus aureus, Pneumococcus, Haemophilus influenza, Neisseria meningitides, Streptococcus pneumonia, Methicillin-resistant Staphylococcus aureus (MRSA), Klebsiella or Enterobacter infection.

Treatment of the inflammatory disorder can be assessed in various ways, but typically involves determining an improvement in one or more physiological parameters of the subject.

Useful physiological parameters may be one or more of the group consisting of: the level of a pro-inflammatory cytokine, the level of an anti-inflammatory cytokine, the level of a catecholamine, the level of an immune cell population, the level of an immune cell surface co-stimulatory molecule, the level of a factor involved in the inflammation cascade, the level of an immune response mediator, and the rate of splenic blood flow.

Improvement in a determined physiological parameter in the context of the invention may be one or more of the group consisting of: a reduction in a pro-inflammatory cytokine, an increase in an anti-inflammatory cytokine, an increase in a catecholamine, a change in an immune cell population, a change in an immune cell surface co-stimulatory molecule, a reduction in a factor involved in the inflammation cascade, a change in the level of an immune response mediator and a decrease in splenic blood flow. The invention might not lead to a change in all of these parameters.

By stimulating a splenic arterial nerve at a site where the splenic artery is not in direct contact with the pancreas, the spleen may: (a) decrease the secretion of a pro-inflammatory cytokine compared to baseline secretion; and/or (b) increase the secretion of an anti-inflammatory cytokine compared to baseline secretion. For example, the decrease in a pro-inflammatory cytokine secretion may be by: ≤5%, ≤10%, ≤15%, ≤20%, ≤25%, ≤30%, ≤35%, ≤40%, ≤45%, ≤50%, ≤60%, ≤70%, ≤80%, ≤90% or ≤95%. The increase in an anti-inflammatory cytokine secretion may be by: ≤5%, ≤10%, ≤15%, ≤20%, ≤25%, ≤30%, ≤35%, ≤40%, ≤45%, ≤50%, ≤60%, ≤70%, ≤80%, ≤90%, ≤95%, ≤100%, ≤150% or ≤200%.

Once the cytokine is secreted into the circulation, its concentration in the circulation is diluted. Stimulation of the splenic arterial nerve may result in: (a) a decrease in the level of a pro-inflammatory cytokine in the plasma or serum by ≤5%, ≤10%, ≤15%, ≤20%, ≤25%, ≤30%, ≤35%, ≤40%, ≤45%, ≤50%, ≤60%, ≤70%, ≤80%, ≤90%, or ≤95%; and/or (b) an increase in the level of an anti-inflammatory cytokine in the plasma or serum by ≤5%, ≤10%, ≤15%, ≤20%, ≤25%, ≤30%, ≤35%, ≤40%, ≤45%, ≤50%, ≤60%, ≤70%, ≤80%, ≤90%, ≤95%, ≤100%, ≤150% or ≤200%. Preferably the level in the serum is measured.

By stimulating the splenic arterial nerve, the level of catecholamine (e.g. norepinephrine or epinephrine), e.g. its level in the spleen, may increase, for example, by: ≤5%, ≤10%, ≤15%, ≤20%, ≤25%, ≤30%, ≤35%, ≤40%, ≤45%, ≤50%, ≤60%, ≤70%, ≤80%, ≤90%, ≤95%, ≤100%, ≤150% or ≤200%.

For example, the inventors found that stimulating a splenic arterial nerve can decrease the level of a pro-inflammatory cytokine (e.g. TNFα) in the serum by 30%-60%.

Pro-inflammatory cytokines are known in the art. Examples of these include tumor necrosis factor (TNF; also known as TNFα or cachectin), interleukin (IL)-1α, IL-1β, IL-2; IL-5, IL-6, IL-8, IL-15, IL 18, interferon γ (IFN-γ); platelet-activating factor (PAF), thromboxane; soluble adhesion molecules; vasoactive neuropeptides; phospholipase A2; plasminogen activator inhibitor (PAI-1); free radical generation; neopterin; CD14; prostacyclin; neutrophil elastase; protein kinase; monocyte chemotactic proteins 1 and 2 (MCP-1, MCP-2); macrophage migration inhibitory factor (MIF), high mobility group box protein 1 (HMGB-1), and other known factors.

Anti-inflammatory cytokines are also known in the art. Examples of these include IL-4, IL-10, IL-17, IL-13, IL-1α, and TNFα receptor.

It will be recognized that some of the pro-inflammatory cytokines may act as anti-inflammatory cytokines in certain circumstances, and vice-versa. Such cytokines are typically referred to as pleiotropic cytokines.

In some embodiments, stimulation of the splenic arterial nerve may result in: (a) a decrease in the level of an anti-inflammatory cytokine in the plasma or serum by ≤5%, ≤10%, ≤15%, ≤20%, ≤25%, ≤30%, ≤35%, ≤40%, ≤45%, ≤50%, ≤60%, ≤70%, ≤80%, ≤90%, or ≤95%; and/or (b) an increase in the level of a pro-inflammatory cytokine in the plasma or serum by ≤5%, ≤10%, ≤15%, ≤20%, ≤25%, ≤30%, ≤35%, ≤40%, ≤45%, ≤50%, ≤60%, ≤70%, ≤80%, ≤90%, ≤95%, ≤100%, ≤150% or ≤200%.

In this context the invention may be useful for increasing an immune response in a subject. For example, increasing an immune response or a pro-inflammatory response may be beneficial in a subject who is immunocompromised and thus in need of increasing pro-inflammatory cytokines for inducing beneficial pro-inflammatory responses. This may be particularly beneficial in immunocompromised subjects who are particularly vulnerable to infections. Examples of immunocompromised subjects in which this embodiment of the invention may be useful include, but are not limited to, subjects undergoing chemotherapy, subjects with HIV or AIDS, subjects taking a course of steroids, and subjects with immunosenescence, for example, subjects with age-associated immunodeficiency. In some embodiments, the invention may be used to increase a pro-inflammatory response in a subject wherein that subject is undergoing or is about to undergo a therapy in which immunocompromisation is an undesired side effect of that therapy. In other embodiments, the invention is useful for inducing a pro-inflammatory response to boost the acquisition of resistance provided by a vaccine. In other words, the neurostimulation device of the invention may be used in a method of vaccination, e.g. to boost the efficacy of a vaccine.

Factors involved in immune responses may be useful measurable parameters in the context of the invention, for example, TGF, PDGF, VEGF, EGF, FGF, I-CAM, nitric oxide.

Chemokines may also be useful measurable parameters in the context of the invention, such as 6cKine and MIP3beta, and chemokine receptors, including CCR7 receptor.

Changes in immune cell population (Langerhans cells, dendritic cells, lymphocytes, monocytes, macrophages), or immune cell surface co-stimulatory molecules (Major Histocompatibility, CD80, CD86, CD28, CD40) may also be useful measurable parameters in the context of the invention. Applying a signal to the nerves according to the invention can cause a reduction in the total counts of circulating or tissue-specific (e.g. joint-specific in the case of rheumatoid arthritis) leukocytes (including monocytes and macrophages, lymphocytes, neutrophils, etc.).

Factors involved in the inflammatory cascade may also be useful measurable parameters in the context of the invention. For example, the signal transduction cascades include factors such as NFκ-B, Egr-1, Smads, toll-like receptors, and MAP kinases.

Methods of assessing these physiological parameters are known in the art. Detection of any of the measurable parameters may be done before, during and/or after modulation of neural activity in the nerve.

For example, a cytokine, chemokine, or a catecholamine (e.g. norepinephrine or epinephrine) may be directly detected, e.g. by ELISA. Alternatively, the presence or amount of a nucleic acid, such as a polyribonucleotide, encoding a polypeptide described herein may serve as a measure of the presence or amount of the polypeptide. Thus, it will be understood that detecting the presence or amount of a polypeptide will include detecting the presence or amount of a polynucleotide encoding the polypeptide.

Quantitative changes of the biological molecules (e.g. cytokines) can be measured in a living body sample such as urine or plasma. Detection of the biological molecules may be performed directly on a sample taken from a subject, or the sample may be treated between being taken from a subject and being analyzed. For example, a blood sample may be treated by adding anti-coagulants (e.g. EDTA), followed by removing cells and cellular debris, leaving plasma containing the relevant molecules (e.g. cytokines) for analysis. Alternatively, a blood sample may be allowed to coagulate, followed by removing cells and various clotting factors, leaving serum containing the relevant molecules (e.g. cytokines) for analysis.

In the embodiments where the signal is applied whilst the subject is asleep, the invention may involve determining the subject's circadian rhythm phase markers, such as the level of cortisol (or its metabolites thereof), the level of melatonin (or its metabolites thereof) or core body temperature. Cortisol or melatonin levels can be measured in the blood (e.g. plasma or serum), saliva or urine. Methods of determining the levels of these markers are known in the art, e.g. by enzyme-linked immunosorbent assay (ELISA) or radioimmunoassay. If measurements of the subject's circadian rhythm phase markers indicate circadian oscillations of inflammatory markers which may beneficially be regulated by application of a signal with a neurostimulation device or system of the invention, then application of the signal at night at a suitable periodicity according to the subject's circadian rhythm may be appropriate.

As used herein, a physiological parameter is not affected by the modulation (e.g. stimulation) of the splenic neural activity if the parameter does not change (in response to nerve modulation) from the normal value or normal range for that value of that parameter exhibited by the subject or subject when no intervention has been performed, i.e. it does not depart from the baseline value for that parameter. Such a physiological parameter may be arterial pressure, heart rate or glucose metabolism. Suitable methods for determining changes in any these physiological parameters would be appreciated by the skilled person.

The skilled person will appreciate that the baseline for any neural activity in a subject need not be a fixed or specific value, but rather can fluctuate within a normal range or may be an average value with associated error and confidence intervals. Suitable methods for determining baseline values are well known to the skilled person.

As described herein, a physiological parameter is determined in a subject when the value for that parameter exhibited by the subject at the time of detection is determined. A detector (e.g. a physiological sensor subsystem, a physiological data processing module, a physiological sensor, etc.) is any element able to make such a determination.

Thus, in certain embodiments, the method according to this aspect of the invention further comprises a step of determining one or more physiological parameters of the subject, wherein the signal is applied only when the determined physiological parameter meets or exceeds a predefined threshold value. In such embodiments wherein more than one physiological parameter of the subject is determined, the signal may be applied when any one of the determined physiological parameters meets or exceeds its threshold value, alternatively only when all of the determined physiological parameters meet or exceed their threshold values. In certain embodiments, the signal is applied by a system of the invention, which in addition to the neurostimulation device comprises at least one detector configured to determine the one or more physiological parameters of the subject.

In certain embodiments, the physiological parameter is an action potential or pattern of action potentials in a nerve of the subject, wherein the action potential or pattern of action potentials is associated with the disease, disorder or condition to be treated.

A predefined threshold value for a physiological parameter is defined elsewhere herein.

A subject of the invention may, in addition to being treated with a neurostimulation device or system according to the invention, receive medicine for their disease, disorder or condition, as discussed elsewhere herein. In the methods of the invention, anticoagulant therapy, e.g. with heparin, may be administered to the subject prior to, following, and/or simultaneously with the application of the neurostimulation device of the invention.

Suitable Forms of an Electrical Signal

The neurostimulation device according to the invention applies an electrical signal via at least one electrode which is placed in proximity to, i.e. in a signaling relationship with, a splenic arterial nerve when the distal end of the catheter or stent of the neurostimulation device is inserted into a splenic artery. The electrode may be said to be placed in signaling contact with the splenic arterial nerve. As used herein, "signaling contact" is where at least part of the electrical signal applied via the at least one electrode is received at the nerve.

In the context of the treatment of acute medical conditions, the electrical signal preferably provides a single treatment, e.g. in acute clinical settings. That is not to say that the electrical signal is only applied once. During the single treatment, the electrical signal may be applied to the nerve continuously, episodically and/or periodically. Preferably, the electrical signal is applied to the nerve until there is an improvement in a physiological parameter of the subject. In the context of the treatment of acute medical conditions, a catheter may be preferable over a stent.

In the context of the treatment of chronic medical conditions, a stent may be preferable over a catheter.

Electrical signals applied according to the invention (in any medical setting described herein) are ideally non-destructive. As used herein, a "non-destructive signal" is a signal that, when applied, does not irreversibly damage the underlying neural signal conduction ability of the nerve. That is, application of a non-destructive signal maintains the ability of the nerve or fibers thereof, or other nerve tissue to which the signal is applied, to conduct action potentials when application of the signal ceases, even if that conduction is in practice artificially stimulated as a result of application of the non-destructive signal.

Electrical signals applied according to the invention may be a voltage or a current waveform (e.g. constant voltage or a constant current waveform).

The electrical signal may be characterized by one or more electrical signal parameters. The electrical signal parameters include waveform, frequency, and amplitude.

Alternatively or additionally, the electrical signal may be characterized by the pattern of application of the electrical signal to the nerve. The pattern of application refers to the timing of the application of the electrical signal to the nerve. The pattern of application may be continuous application or periodic application.

Continuous application refers to a situation in which the electrical signal is applied to the nerve in a continuous manner. In embodiments where the electrical signal is a series of pulses, the gaps between those pulses (i.e. between the pulse width and the phase duration) do not mean that the signal is not continuously applied.

Periodic application refers to where the electrical signal is applied to the nerve in a repeating pattern (e.g. an on-off pattern).

In the context of the treatment of a disease, disorder or condition associated with inflammation, e.g. an inflammatory disorder, e.g. an autoimmune disorder, the pattern of application of the electrical signal may be continuous application, periodic application and/or episodic application. Episodic application refers to where the electrical signal is applied to the nerve for a discrete number of episodes throughout a day. Each episode may be defined by a set duration or a set number of iterations of the electrical signal. Where the electrical signal is applied periodically and episodically, it means that the signal is applied in a periodic manner for each episode of application. Where the electrical signal is applied continuously and episodically, it means that the signal is applied in a continuous manner for each episode of application.

The inventors have found preferred electrical signal parameters and patterns of signal application for stimulating neural activity in a splenic arterial nerve by applying the signal to the application site for use in accordance with the invention, which parameters and/or patterns lead to increased immunosuppressive effects while reducing possible systemic effects when stimulating neural activity in said nerve. The preferred signal parameters and patterns of application are discussed in detail below.

The inventors have also found improved waveforms of the electrical signal which decrease the pulse height required in order to stimulate neural activity in a human nerve supplying the spleen, whilst reducing the burden on the stimulator. The improved waveforms are discussed in detail below.

Waveform

Modulation (e.g. stimulation) of a nerve supplying the spleen can be achieved using electrical signals applied by the neurostimulation device of the invention which serve to replicate the normal neural activity of the nerve. Thus, the waveform of the electrical signal comprises invention pulse train.

A pulse train comprises a plurality of sequential pulses, which may be characterized by pulse width, pulse height and/or interphase delay. Pulse width refers to the time duration between the start of a pulse and the end of the same pulse. In some cases where a pulse comprises a first phase that is the primary phase and a second phase which is the recovery phase, for example an anodic and/or a cathodic phase, the pulse width refers to a width (or duration) of the first phase. Interphase delay refers to the time period from the end of a pulse to the start of the next pulse. Pulse height, which is also referred to as pulse amplitude, refers to the amplitude of current of the pulse, typically measured in amps.

Pulse width and pulse height are preferably constant for all of the pulses in the pulse train. Likewise, interphase delay is preferably constant between all of the pulses in the pulse train.

The inventors found that for pulse widths of >1 ms (i.e. greater than 1 ms, not including 1 ms) a decrease in the pulse height required to stimulate neural activity in a human splenic nerve is observed. The pulse height required to stimulate neural activity in a nerve is also referred to herein as the 'stimulation threshold' and the 'pulse height threshold'. A decrease in the pulse height threshold is advantageous because the biological efficacy of the electrical signal is improved for use in humans. Moreover, implantable stimulators can have a limitation of the maximum pulse height they can output and in some cases higher amplitudes can have safety concerns. Therefore, with some stimulators a decrease in the pulse height threshold can be advantageous as it translates to a higher degree of nerve activation at a lower amplitude achievable by the stimulator. Therefore, the pulse width of the pulse train may have a lower limit of >1 ms. For example, in cases where the indwelling device is a catheter which may be connectable to an external pulse generator, a lower pulse width may also be used, for example 0.4 ms-1.5 ms, optionally 0.4-1.1 ms.

The inventors also found that for pulse widths over 5 ms there is an increase in both the pulse height threshold and the amount of charge density required in order to stimulate neural activity in a human splenic nerve. As a consequence, the biological efficacy is significantly reduced for pulse widths above 5 ms. Moreover, at these values of pulse height and charge density, the likelihood of tissue scarring in the nerve is increased significantly. Therefore, a pulse width above 5 ms is not desirable for use in humans. Accordingly, the pulse width of the pulse train may have an upper limit of ≤5 ms.

Moreover, the inventors found that for pulse widths greater than 3 ms there is a negligible decrease in the pulse height threshold beyond that experienced by pulse trains having a pulse width of >1 ms. However, for pulse widths greater than 3 ms the amount of charge density per phase required increases. Therefore, the biological efficacy is reduced for pulse widths greater than 3 ms such that diminishing benefits are seen whilst potentially compromising electrochemical integrity of the electrodes, thereby reducing reproducibility of stimulation parameters. More importantly, at pulse widths of around 3 ms tissue scarring starts to be observed. Therefore, the pulse width of the electrical signal may have an upper limit of ≤3 ms.

The inventors also found that for pulse widths around 2 ms both the pulse height threshold required is minimised. Accordingly, the pulse width may be between 1.5 and 2.5 ms, preferably between 1.75 ms and 2.25 ms, more preferably between 1.9 ms and 2.1 ms, even more preferably between 1.95 ms and 2.05 ms, even more preferably between 1.99 ms and 2.01 ms, even more preferably 2 ms.

The inventors additionally found that the inclusion of an interphase delay reduces the threshold of pulse height required to stimulate neural activity in a human splenic nerve. Therefore, in some examples, the pulse train may have an interphase delay.

The inventors further found that longer interphase delays produce greater reductions in pulse height threshold. Accordingly, the interphase delay may have a lower limit of ≥0.1 ms (including 0 ms, i.e. no interphase delay), more preferably ≥0.15 ms, even more preferably ≥0.19 ms, even more preferably still ≥0.2 ms, optionally ≥0.25 ms, optionally ≥0.3 ms. However, at interphase delays greater than 0.3 ms it was found that there is no further reduction in pulse height threshold. Accordingly, the upper limit of interphase delay of the pulse train may be ≤0.3 ms, more preferably ≤0.25 ms. Any combination of the upper and lower limits of interphase delay is possible. Preferred ranges of interphase delay include between 0.1 ms and 0.3 ms, and between 0.2 ms and 0.25 ms. The pulses are preferably square pulses. However, other pulse waveforms such as sawtooth, sinusoidal, triangular, trapezoidal, quasitrapezodial or complex waveforms may also be used with the invention.

The pulses may be biphasic in nature. The term "biphasic" refers to a pulse which applies to the nerve over time both a positive and negative charge (anodic and cathodic phases). For biphasic pulses, the pulse width includes the time duration of a primary phase of the waveform, for example the anodic phase or the cathodic phase. The primary phase may also be referred to herein as the stimulation phase.

The pulses may be charge-balanced. A charge-balanced pulse refers to a pulse which, over the period of the pulse, applies equal amounts (or thereabouts) of positive and negative charge to the nerve. The biphasic pulses are preferably charge-balanced.

The pulses may be symmetric or asymmetric. A symmetric pulse is a pulse where the waveform when applying a positive charge to the nerve is symmetrical to the waveform when applying a negative charge to the nerve. An asymmetric pulse is a pulse where the waveform when applying a positive charge to the nerve is not symmetrical with the waveform when applying a negative charge to the nerve.

If the biphasic pulse is asymmetric, but remains charged balanced, then the areas of the opposing phases must equal Amplitude (see below) can be reduced, but the pulse width would need to be extended to ensure the area under the curve is matched.

In an exemplary embodiment, the waveform is a pulse train with biphasic, asymmetric, charge balanced square pulses.

Amplitude

For the purpose of the invention, the amplitude is referred to herein in terms of charge density per phase. Charge density per phase applied to the nerve by the electrical signal is defined as the integral of the current over one phase (e.g. over one phase of the biphasic pulse in the case of a charge-balanced biphasic pulse). Thus, charge density per phase applied to the nerve by the electrical signal is the charge per phase per unit of surface area of the at least one electrode intravascularly (a stimulating electrode surface area), and also the integral of the current density over one phase of the signal waveform. Put another way, the charge density per phase applied to the nerve by the electrical signal is the charge per phase applied to the nerve by the electrical signal divided by the surface area of the at least one electrode (generally the cathode) intravascularly.

The charge density per phase that is useful for the invention represents the amount of energy required to stimulate neural activity in a nerve supplying the spleen to increase immunosuppressive effects.

The inventors found the current that is most useful to stimulate neural activity in a splenic arterial nerve to be between 1 mA and 400 mA, 1 mA and 100 mA; preferably between 5 mA and 50 mA, optionally between 5 mA and 100 mA, preferably between 10 mA and 40 mA, preferably between 20 mA and 30 mA.

The inventors found the charge density per phase that is useful to stimulate neural activity in a splenic arterial nerve to be up to 4000 μC per $cm^2$ per phase (e.g. between 150 μC to 600 μC per $cm^2$ per phase). For example, the charge density per phase applied by the electrical signal may be ≤20 μC per $cm^2$ per phase, ≤50 μC per $cm^2$ per phase, ≤100 μC per $cm^2$ per phase, ≤150 μC per $cm^2$ per phase, ≤200 μC per $cm^2$ per phase, ≤250 μC per $cm^2$ per phase, ≤300 μC per $cm^2$ per phase, ≤400 μC per $cm^2$ per phase, ≤500 μC per $cm^2$ per phase, ≤750 μC per $cm^2$ per phase, ≤1000 μC per $cm^2$ per phase, ≤1250 μC per $cm^2$ per phase, ≤1500 μC per $cm^2$ per phase, ≤1800 μC per $cm^2$ per phase, ≤2000 μC per $cm^2$ per phase, ≤2500 μC per $cm^2$ per phase, ≤3000 μC per $cm^2$ per phase, or ≤3500 μC per $cm^2$ per phase. Additionally or alternatively, the charge density per phase applied by the electrical signal may be ≥20 μC per $cm^2$ per phase, ≥50 μC per $cm^2$ per phase, ≥100 μC per $cm^2$ per phase, ≥150 μC per $cm^2$ per phase, ≥200 μC per $cm^2$ per phase, ≥250 μC per $cm^2$ per phase, ≥300 μC per $cm^2$ per phase, ≥400 μC per $cm^2$ per phase, ≥500 μC per $cm^2$ per phase, ≥750 μC per $cm^2$ per phase, ≥1000 μC per $cm^2$ per phase, ≥1250 μC per $cm^2$ per phase, ≥1800 μC per $cm^2$ per phase, ≥2000 μC per $cm^2$ per phase, ≥2500 μC per $cm^2$ per phase, ≥3000 μC per $cm^2$ per phase, or ≥3500 μC per $cm^2$ per phase. Any combination of the upper and lower limits above is also possible. For example, the charge density per phase applied by the electrical signal may be between 20 μC to 3500 μC per $cm^2$ per phase, optionally between 50 μC to 3000 μC per $cm^2$ per phase, optionally between 200 μC to 2000 μC per $cm^2$ per phase, optionally between 300 μC to 1800 μC per $cm^2$ per phase, optionally between 400 μC to 1500 μC per $cm^2$ per phase, optionally between 500 μC to 1500 μC per $cm^2$ per phase.

The charge density per phase required to stimulate neural activity in a human splenic arterial nerve may depend on the pulse width being used. The inventors found that the charge density per phase required to stimulate neural activity in a human splenic arterial nerve with a pulse width of 2 ms may to be up to 4000 μC per $cm^2$ per phase (e.g. up to 850 μC per $cm^2$ per phase). Accordingly, the charge density per phase applied by the electrical signal when the pulse width is 2 ms may be ≤20 μC per $cm^2$ per phase, ≤80 μC per $cm^2$ per phase, ≤140 μC per $cm^2$ per phase, ≤170 μC per $cm^2$ per phase, ≤230 μC per $cm^2$ per phase, ≤250 μC per $cm^2$ per phase, ≤300 μC per $cm^2$ per phase, ≤350 μC per $cm^2$ per phase, ≤400 μC per $cm^2$ per phase, ≤450 μC per $cm^2$ per phase, ≤500 μC per $cm^2$ per phase, ≤600 μC per $cm^2$ per phase, ≤700 μC per $cm^2$ per phase, ≤800 μC per $cm^2$ per phase, or ≤835 μC per $cm^2$ per phase. Any combination of the upper and lower limits above is also possible. For example, the charge density per phase may be between 20 μC to 800 μC per $cm^2$ per phase, optionally100 μC to 700 μC per $cm^2$ per phase, optionally between 200 μC to 600 μC per $cm^2$ per phase, optionally between 300 μC to 400 μC per $cm^2$ per phase.

When using other pulse widths, the charge density per phase required to input to stimulate neural activity in a human splenic arterial nerve may be ≤4000 μC per $cm^2$ per phase, optionally between 20 μC to 3500 μC per $cm^2$ per phase, optionally between 50 μC to 3000 μC per $cm^2$ per phase, optionally between 200 μC to 2000 μC per $cm^2$ per phase, optionally between 300 μC to 1800 μC per $cm^2$ per phase, optionally between 400 μC to 1500 μC per $cm^2$ per phase, optionally between 500 μC to 1500 μC per $cm^2$ per phase.

The charge density used may depend on the desired recruitment of the nerve. For example, the lower charge densities may represent threshold (minimum required charge density), whereas the upper (or higher) charge densities may represent charge densities required for full recruitment (or higher requirement).

The total charge applied to the nerve by the electrical signal in any given time period is a result of the charge density per phase of the signal, in addition to the frequency of the signal, the pattern of application of the signal and the surface area of at least one electrode intravascularly. The frequency of the signal, the pattern of application of the signal and the surface area of at least one electrode intravascularly are discussed further herein.

It will be appreciated by the skilled person that the amplitude of an applied electrical signal necessary to achieve the intended stimulation of the neural activity will depend upon the positioning of the electrode and the associated electrophysiological characteristics (e.g. impedance). It is within the ability of the skilled person to determine the appropriate current amplitude for achieving the intended modulation of the neural activity in a given subject.

It would be of course understood in the art that the electrical signal applied to the nerve would be within clinical safety margins (e.g. suitable for maintaining nerve signaling function, suitable for maintaining nerve integrity, and suitable for maintaining the safety of the subject). The electrical parameters within the clinical safety margin would typically be determined by pre-clinical studies.

The table below demonstrates example electrical signal parameters for each corresponding recruitment level of human splenic nerve using computational models. These are example values only, where a different current amplitude or pulse width may be used depending on the electrode surface area or electrode configuration of a device to achieve a corresponding charge density. In the examples given below, the electrode area is assumed to be 0.067 $cm^2$. A range around the example values provided may also be used.

| | Recruitment (10%) | | Recruitment (50%) | | Recruitment (100%) | |
|---|---|---|---|---|---|---|
| Pulse width | Stimulation amplitude | Charge densities | Stimulation Amplitude | Charge densities | Stimulation Amplitude | Charge densities |
| 200 μs | ~84.2 mA | ~250 μC/cm$^2$ | ~139.7 mA | ~417 μC/cm$^2$ | ~385.2 mA | ~1149 μC/cm$^2$ |
| 400 μs | ~43 mA | ~250 μC/cm$^2$ | ~75.25 mA | ~449 μC/cm$^2$ | ~209.6 mA | ~1251 μC/cm$^2$ |
| 600 μs | ~28.67 mA | ~250 μC/cm$^2$ | ~55.55 mA | ~497 μC/cm$^2$ | ~152.3 mA | ~1363 μC/cm$^2$ |
| 800 μs | ~21.5 mA | ~250 μC/cm$^2$ | ~44.79 mA | ~534 μC/cm$^2$ | ~130.8 mA | ~1561 μC/cm$^2$ |
| 1000 μs | ~17.92 mA | ~267.3 μC/cm$^2$ | ~39.41 mA | ~590 μC/cm$^2$ | ~112.9 mA | ~1685 μC/cm$^2$ |
| 2000 μs | ~16.12 mA | ~481 μC/cm$^2$ | ~37.62 mA | ~1123 μC/cm$^2$ | ~107.5 mA | ~3208 μC/cm$^2$ |

Periodic Application

Periodic application refers to where the electrical signal is applied to the nerve in a repeating pattern. The preferred repeating pattern is an on-off pattern, where the signal is applied in a sequence of pulse trains for a first duration, referred to herein as an 'on' duration, then stopped for a second duration, referred to herein as an 'off' duration, then applied again for the first duration, then stopped again for the second duration, etc.

The periodic on-off pattern may have an on duration of between 0.1 and 10 s and an off duration of between 0.5 and 30 s. For example, the on duration may be ≤0.2 s, ≤0.5 s, ≤1 s, ≤2 s, ≤5 s, or ≤10 s. Alternatively or additionally, the on duration may be ≥0.1 s, ≥0.2 s, ≥0.5 s, ≥1 s, ≥2 s, or ≥5 s.

Any combination of the upper and lower limits above for the on duration is also possible. For example, the off duration may be ≤1 s, ≤3 s, ≤5 s, ≤10 s, ≤15 s, ≤20 s, ≤25 s, or ≤30 s. Alternatively or additionally, the off duration may be ≥0.5 s, ≥1 s, ≥2 s, ≥5 s, ≥10 s, ≥15 s, ≥20 s, or ≤25 s. Any combination of the upper and lower limits above for the off duration is also possible.

In an exemplary embodiment, the periodic on-off pattern has an on duration of 0.5 s on, and an off duration of 4.5 sec off.

Periodic application may also be referred to as a duty cycled application. A duty cycle represents the percentage of time that the signal is applied to the nerve for a cycle of the periodic pattern. For example, a duty cycle of 20% may represent a periodic pattern having an on duration of 2 s, and an off duration of 10 s. Alternatively, a duty cycle of 20% may represent a periodic pattern having a on duration of 1 s, and an off duration of 5 s.

Duty cycles suitable for the present invention are between 0.1% and 100%. For example, the duty cycle may be 10% which may reduce smooth muscle contraction of the artery.

Episodic Application

Episodic application refers to where the electrical signal is applied to the nerve for a discrete number of episodes throughout a day. The electrical signal according to the invention may be applied for up to a maximum of twenty four episodes per day. For example, the number of episodes of signal application per day may be one, two, three, four, five, six, seven, eight, nine, ten, eleven, twelve or another number up to twenty four. When the indwelling device is a catheter, the maximum number of episodes per day may be higher.

The electrical signal may be applied episodically every 2 to 3 hours. For example, the electrical signal may be applied episodically once every 2 hours, 2 hour 15 min, 2 hour 30 min, 2 hour 45 min, or 3 hours.

Each episode may be defined by a set duration or a set number of iterations of the electrical signal. In some embodiments, each episode comprises applying to the nerve between 10 and 3000 pulses of the electrical signal, optionally between 100 and 2400 pulses of the electrical signal, further optionally between 50 and 2400 pulses, e.g. between 200 and 1200 pulses of the electrical signal, between 400 and 600 pulses of the electrical signal, etc. For example, each episode may comprise applying ≤10, ≤50, ≤60, ≤100, ≤400, ≤600, ≤800, ≤1200, ≤1600, ≤2000, or ≤2400 pulses of the electrical signal. In another example, each episode may comprise applying ≤200, ≤400, ≤600, ≤800, ≤1000, or ≤1200 pulses of the electrical signal. In a further example, each episode may comprise applying ≤400, ≤425, ≤450, ≤475, ≤500, ≤525, ≤550, ≤575, or ≤600 pulses of the electrical signal.

In other embodiments, each episode comprises between 20 and 40 iterations of the periodic pattern. For example, each episode comprises applying 20, 25, 30, 35, or 40 iterations of the periodic pattern, or any number therebetween. The higher the frequency, the lower the number of iterations.

As mentioned previously, in some embodiments, the episodes may be based on the subject's sleep-wake cycle, in particular the episodes may be whilst the subject is asleep. In some such embodiments, the episodes may be applied between 10 pm and 6 am. This may also be influenced by the surgery times. The sleep-wake cycle may be measured via known methods by detecting the subject's circadian rhythm phase markers (e.g. cortisol level, melatonin level or core body temperature), and/or a detector for detecting the subject's movements.

Frequency

Frequency is defined as the reciprocal of the phase duration of the electrical waveform (i.e. 1/phase), or put another way the interpulse timing (pulse to pulse timing).

The inventors have found preferred frequencies for stimulating a splenic arterial nerve when using the device of the invention. In particular, the inventors have found preferred frequencies for embodiments where the electrical signal is applied periodically and for embodiments where the electrical signal is applied continuously.

In embodiments where the electrical signal is applied periodically, the electrical signal has a frequency of ≤300 Hz, preferably ≤50 Hz, more preferably ≤10 Hz. For example, the frequency of the electrical signal may be ≤50 Hz, ≤100 Hz, ≤150 Hz, ≤200 Hz, ≤250 Hz or ≤300 Hz. In other examples, the frequency of the electrical signal may be ≤10 Hz, ≤15 Hz, ≤20 Hz, ≤25 Hz, ≤30 Hz, ≤35 Hz, ≤40 Hz, ≤45 Hz, or ≤50 Hz. In further examples, the frequency may be ≤1 Hz, ≤2 Hz, ≤5 Hz, or ≤10 Hz. Additionally or alternatively, the frequency of the electrical signal may be ≥10 Hz, ≥15 Hz, ≥20 Hz, ≥25 Hz, ≥30 Hz, ≥35 Hz ≥40 Hz, ≥45 Hz, or ≥50 Hz. In other examples, the frequency of the electrical signal may be ≥0.1 Hz, ≥0.2 Hz, ≥0.5 Hz, ≥1 Hz, ≥2 Hz, or ≥5 Hz. Any combination of the upper and lower limits above is also possible.

In embodiments where the electrical signal is applied continuously, the electrical signal has a frequency of ≤50 Hz, preferably ≤10 Hz, more preferably ≤2 Hz, even more preferably ≤1 Hz. For example, the frequency may be ≤1 Hz, ≤2 Hz, ≤5 Hz, or ≤10 Hz. In other examples the frequency may be ≤0.1 Hz, ≤0.2 Hz, ≤0.3 Hz, ≤0.4 Hz ≤0.5 Hz, ≤0.6 Hz ≤0.7 Hz, ≤0.8 Hz, or ≤0.9 Hz. Additionally or alternatively, the frequency of the electrical signal may be ≥0.1 Hz, ≥0.2 Hz, ≥0.5 Hz, ≥1 Hz, ≥2 Hz, or ≥5 Hz. Any combination of the upper and lower limits above is also possible.

Where the signal waveform comprises a pulse train, the pulses are applied to the nerve at intervals according to the above-mentioned frequencies. For example, a frequency of 50 Hz results in 50 pulses being applied to the nerve per second.

General Definitions

The term "comprising" encompasses "including" as well as "consisting" e.g. a composition "comprising" X may consist exclusively of X or may include something additional e.g. X+Y. The term "around" or "about" in relation to a numerical value is optional and means, for example, x±10%. Unless otherwise indicated each embodiment as described herein may be combined with another embodiment as described herein.

Any range or device value given herein may be extended or altered without losing the effect sought, as will be apparent to the skilled person.

It will be understood that the benefits and advantages described above may relate to one embodiment or may relate to several embodiments. The embodiments are not limited to those that solve any or all of the stated problems or those that have any or all of the stated benefits and advantages.

Any reference to 'an' item refers to one or more of those items. The term 'comprising' is used herein to mean including the method blocks or elements identified, but that such blocks or elements do not comprise an exclusive list and a method or apparatus may contain additional blocks or elements.

The steps of the methods described herein may be carried out in any suitable order, or simultaneously where appropriate. Additionally, individual blocks may be deleted from any of the methods without departing from the spirit and scope of the subject matter described herein. Aspects of any of the examples described above may be combined with aspects of any of the other examples described to form further examples without losing the effect sought.

It will be understood that the above description of a preferred embodiment is given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the scope of this invention.

MODES OF THE INVENTION

Study 1: Effects of Electrostimulation in an In Vivo LPS Animal Model The inventors sought to determine the effect of innervation on the clinical response of pigs in an endotoxemic shock model

Materials and Methods

Animals

A total of 12 pigs (over the initial 38) (age/weight) were used for this section of the study. None of these 12 pigs were excluded from the analysis.

General Design

Three hours after the initial stimulations performed in study 1, 12 animals received an intravenous injection of 2.5 μg/kg endotoxin (Purified lipopolysaccharides from the cell membrane of *Escherichia coli* O111:B4; Sigma Aldrich), administered over a period of 5 minutes. This dose was selected through a thorough review of the available literature and personal experiences. This dose was chosen to be in the lower end of the range of doses used previously by other groups. Animals which received SpN stimulation for the ex vivo part of the study were divided in 2 groups; the SpN 'Prophylactic' group (SpN-P) did not receive any further stimulation whereas the SpN 'Therapeutic' group (SpN-T) received another second SpN stimulation during the LPS injection.

The stimulation parameters include a 1 minute duration, with square, biphasic, charge balanced symmetrical pulses at 10 Hz, with a 400 μs pulse duration and a current amplitude corresponding to a charge density per phase of 30 to 90 $\mu C/Cm^2$/phase. The stimulation was applied once and then repeated a second time 3 hours later at the time where LPS was injected in vivo.

Peripheral venous blood was collected immediately prior to LPS injection (baseline), and then every half hour up to 2 hours post injection. At the end of this time-window pigs were euthanized or used for further final electrophysiological tests. For all of these time points, cytokine analysis (TNFα and IL-6), and routine hematology and biochemistry analyses were performed. Serum was diluted 1:10 for the cytokine analyses.

In animals where the LPS injection caused clinical changes in systemic blood pressure and/or cardiac function, standard clinical therapies such as vasopressin (2.5 IU bolus injections administered i.v. and repeated as needed) and anti-arrhythmic drugs (lidocaine; 2 mg/kg i.v. and/or atropine; 40 μg/kg; i.v.) were given at the discretion of the anesthetist. Animals were euthanized when mean systemic arterial pressure could not be maintained >40 mm Hg, or when the animal completed the pre-determined endpoint.

Statistical Analyses

All analyses were performed with commercially available statistical software (JMP Pro 13.0.0). Continuous variables were visually inspected for normality and outliers. When outliers were identified, statistical tests were performed including and excluding these animals as stated in the result section.

Changes in cytokine and leukocyte levels were calculated as the percentage of baseline samples collected immediately prior to LPS injection. Cytokine and leukocyte levels were subsequently analyzed using a mixed model with stimulation group, time and stimulation group*time as fixed effects, and animal as random effect. Pairwise Student's t-tests were used for Post Hoc analysis. Differences in survival time between stimulation groups was analyzed using the Log Rank test and plotted in a Kaplan Meier plot. Cytokine levels, leukocytes and electrolytes were compared between the different treatment groups at 30 minutes post LPS injection using a two-way ANOVA analysis with Post Hoc All Pairs Student's t-test analysis; this test was also used to compare maximal reduction in mean arterial blood pressure between groups. Statistical significance was defined as $P<0.05$.

Results

Survival

Figure 6A:
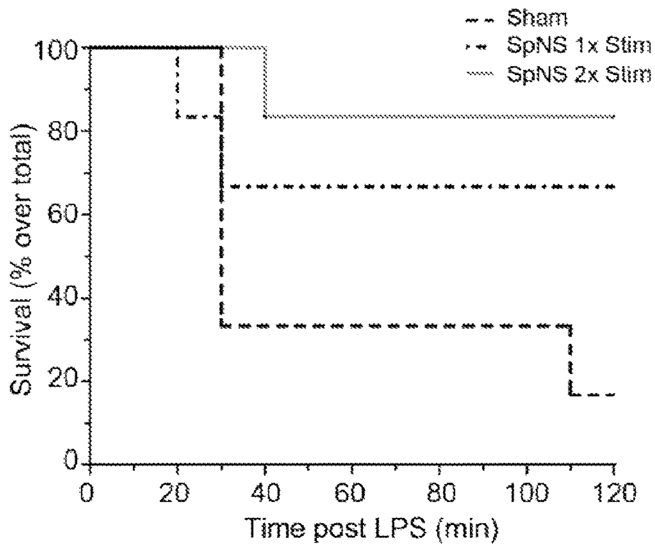
FIGS. 6A, 6B, 6C and 6D show that SpN stimulation 3 hours prior to the in vivo LPS injection promoted survival.
Figure 6B:
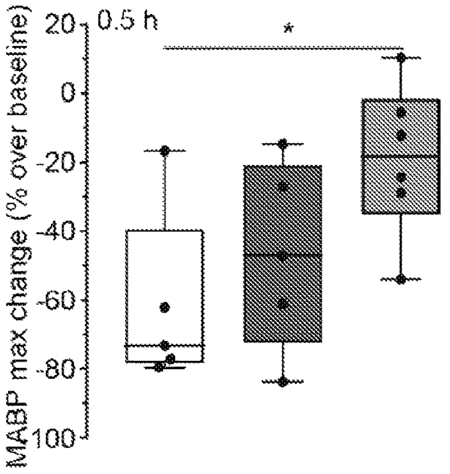

The 2 hours post injection survival rate is reported in FIG. 6A. There was a statistical significant difference in survival rate between the SpN-T vs. Sham (P=0.0194). In brief, LPS injection evoked severe cardiovascular compromise within 10-20 minutes in 5/6 sham animals, necessitating euthanasia (MAP<40 mm Hg despite treatment) prior to reaching the pre-determined endpoint. Conversely, in 5/6 SpN-T stimulated animals, and 4/6 SpN-P stimulated animals, vital parameters including mean arterial blood pressure remained stable throughout the experiment period; for these groups, MAP at 2 hours post injection was 95.3±13.5, 85.9±7.5 and 86.8±9.7% of baseline values, respectively. Likewise, there was a statistically significant difference in maximal reduction in MAP between the SpN-T vs. Sham (P=0.0296, FIG. 6B); mean MAP at the time of euthanasia was 87.1±23.5% of baseline in the SpN-T group (mean survival time 1.8±0.5 hours post injection); 62.7±33.0% of baseline in the SpN-P group (mean survival time 1.4 ±0.8 hours post injection); and 48.6±37.9% of baseline in the Sham group (mean survival time 0.9±0.7 hours post injection).

Figure 6C:
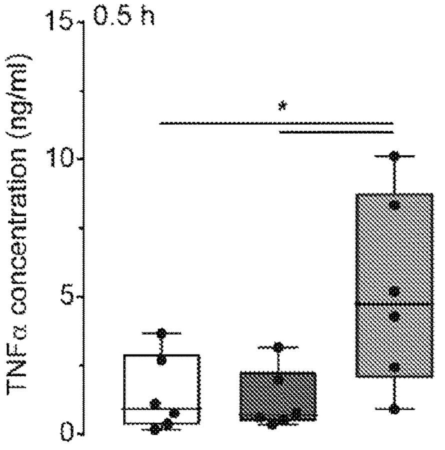
Figure 6D:
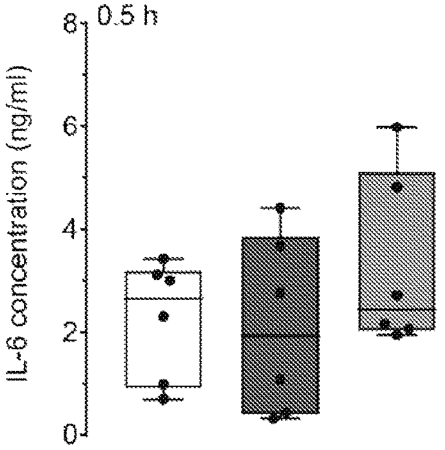
Figure 7A:
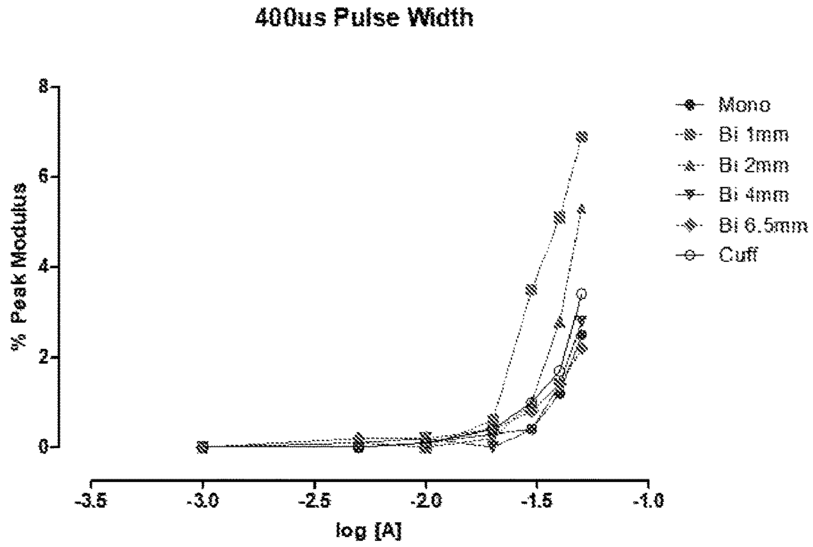
FIG. 7 illustrates an ex vivo comparison of current response curves of compound action potential (CAP) recordings from pig SpN stimulation using either a cuff neurostimulation device or an intravascular neurostimulation device.
Figure 7C:
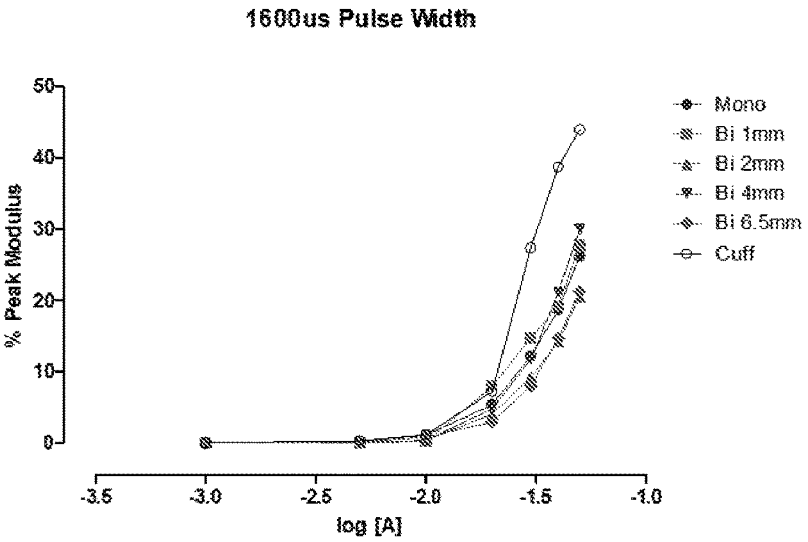
Figure 7E:
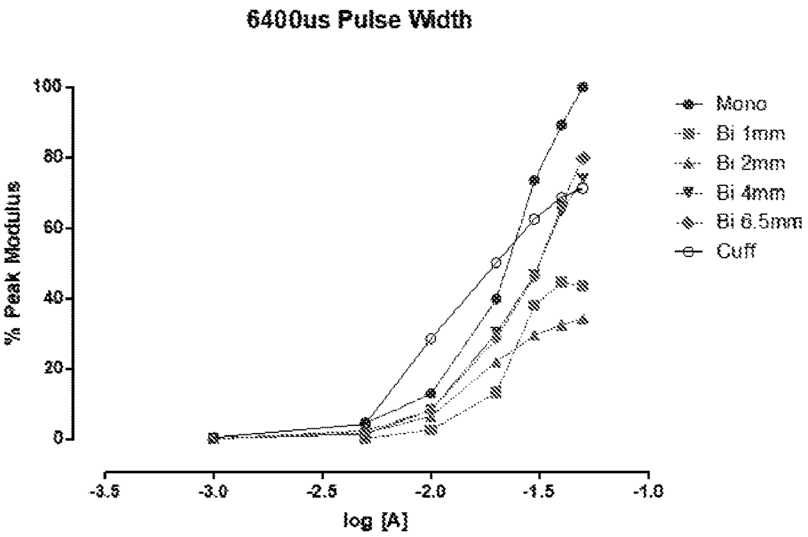
Figure 7B:
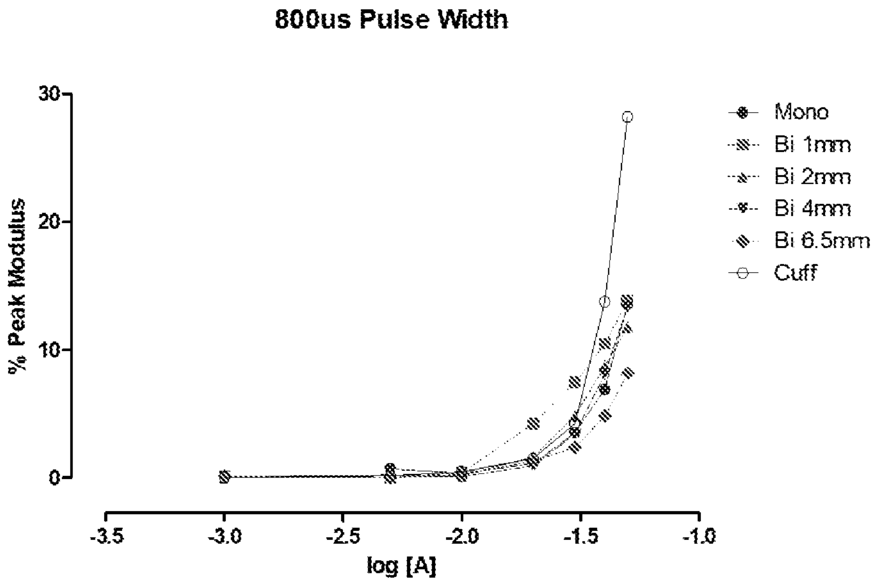
Figure 7D:
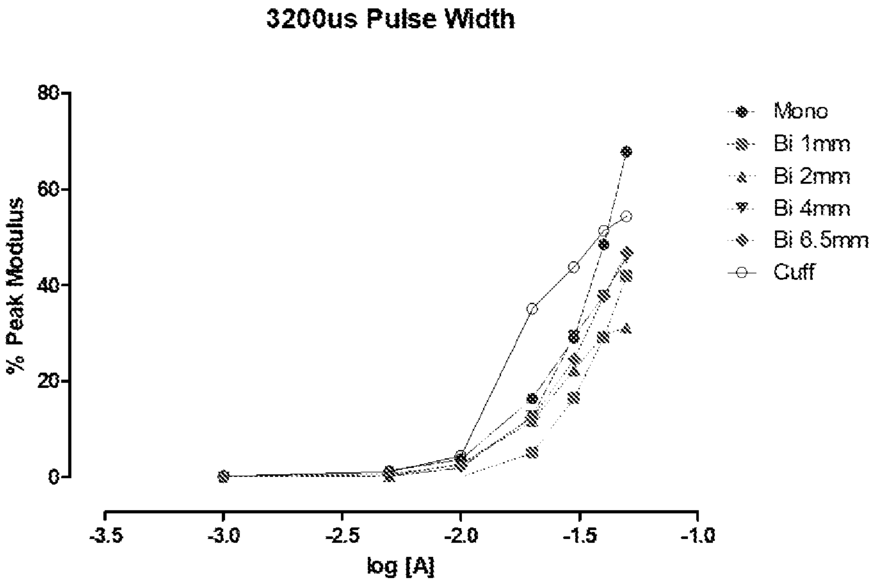

Cytokine quantification. For all groups, LPS injection resulted in a significant increase in TNFα levels in all post-injection samples compared to baseline (P<0.001; FIG. 6C to 6D), with the peak response observed at 1 hour post injection. IL-6 was significantly higher at 2 hours post injection compared to baseline across all groups (P<0.0001).

When comparing cytokine levels at 0.5 hours post injection, TNFα levels were significantly higher in the SpN-T group vs the SpN-P group (P=0.117), and vs the sham group (P=0.0043; FIG. 6C). No difference was found between stimulation groups for IL-6 (FIG. 6D).

Discussion

The administration of LPS in vivo to mimic an inflammatory response provided a good model to test the efficacy of SpN. The administration of LPS (2.5 μg/Kg of body weight) in 45-50 kg pigs caused upregulation of cytokines (TNFα and IL-6) in the blood of all the animals tested. In particular, TNFα reached a peak value of about 12 ng/ml at lh post injection while IL-6 picked around 15 ng/ml at 2 h post LPS. The LPS also caused significant changes in the peripheral blood composition, with reduction in circulating lymphocytes and neutrophils (results not shown). White blood cells in fact probably leaves the circulation to infiltrate tissues and organs during the systemic infection mimicked by the LPS. A significant increase in blood urea, creatinine and total bilirubin as well as an increase in CK and ALP over time was also observed after LPS (results not shown). All these changes indicated that the model was effective and reproducible between animals.

Strikingly sham animals showed a very rapid and strong decrease in systemic MABP, at about 10-15 minutes post LPS administration. Reductions in systemic MABP reached levels that would be rapidly life threatening, thus requiring the administration of vasopressin. However, in most of the controls this was not sufficient to stably restore a normal sMABP. Even when further injections of vasopressin were performed, 4/6 sham controls had to be euthanized at 30 minutes post LPS injection since their sMABP could not be kept above 40 mmHg One of the sham was instead euthanized 110 minutes post LPS injection for the same reason. In some cases, arrhythmias were also observed.

On the opposite, most of the animals that were stimulated (at either −3 h or at −3 h and 0 h, relative to LPS) did not show such strong changes in sMABP. Most of them did not require any pharmacological intervention (i.e. vasopressin). This pro-survival effect of SpN stimulation, however, could not be explained by a lowering of the concentration of LPS-induced cytokines. TNFα and IL-6, in fact, measured at 30 minutes post LPS injection were not reduced in the stimulated animals when compared to sham animals Therefore, even though this model provided the proof that SpN stimulation is able to modulate the response to an inflammatory stimulus, this could not be simply explained by a reduction in the inflammatory response. It has to be considered, however, that since most of the controls had to be euthanized within 30 minutes post LPS administration, further comparison of cytokine levels (at 1, 1.5 and 2 h post LPS) could not be performed between stimulated and sham animals. It is possible, therefore, that a difference in cytokine levels could have been observed in later time points, where TNFα and IL-6 reach their peak values.

Therefore, the data suggest that the pro-survival effect was due to the modulation of some other mechanisms.

Summary

In summary, the inventors found that neural stimulation of a nerve supplying the spleen, and in particular, the splenic arterial nerve, showed pro-survival effects in an in vivo LPS animal model. The inventors also found that applying an electrical signal to the splenic arterial nerves stabilized blood pressure, which drops dramatically in LPS-treated animals, and reduced the maximum reduction in blood pressure. Hence, stimulation of the neural activity of splenic nerves can be particularly useful for treating acute medical conditions, such as life-threatening conditions having physiological changes associated with shock, and cardiovascular dysfunction (e.g. trauma, haemorrhaging and septic shock).

Study 2: Comparison of the Effects of Applying an Electrical Signal to the Splenic Arterial Nerve Ex Vivo Using Either an Intravascular Neurostimulation Device or a Cuff Electrode Background The objective of this study was to compare charge density requirements for intravascular and extravascular neurostimulation devices for stimulating compound action potentials (CAPs) in pig splenic arterial nerves (SpN).

Materials and Methods

Hardware:

- Grass S48 square pulse stimulator
- Digitimer DS5 Isolated Bipolar Current Stimulator
- Power 1401 625 kHz data acquisition interface (CED)
- A-M Systems microelectrode AC amplifier Model 1800
- Custom 2 chamber perfused bath
- Warner Instrument Corp Dual Automatic Temperature Controller TC-344B
- Tektronix TPS2012 oscilloscope
- Custom in-house catheter ("intravascular neurostimulation device"—2.5 mm diameter tubing, 0.5 mm wide rings, approx. 80% circumference, 4 pole, variable spacing)
- 5 mm Oscor Omega Cuff
- Ground electrode for hook recording utilized platinum wire in contact or wrapped around nerve. Hook recording electrodes were Ag/AgCl. Stimulation performed on proximal splenic artery.

Recording Settings:
- Notch: out
- Low Cut-off: 10 Hz
- High Cut-off: 1 kHz
- Gain: 10000-adjusted as needed Stimulation Settings:
- DS5 range: 5 mA/V (10V/50 mA)
- Grass S48 Multiplier: 0.1X or 1X adjustable as needed Software:
- Spike2 v8.04 (CED)
- GraphPad Prism v5.03
- Assay Buffer (mM)
- NaCl (113.0), KCl (4.8), $CaC_{12}$ (2.5), $KH_2PO_4$ (1.2), $MgSO_4$ (1.2), $NaHCO_3$ (25.0) and dextrose (5.55) and equilibrated with 95% $O_2$: 5% $CO_2$
- IACUC Protocol
- Tissue obtained by removal from naïve porcine carcass euthanized via blow to the head at RVC, Hatfield UK Procedure Splenic artery, vein, and nerve was removed from the pig carcass and placed in ice cold Krebs-Henseleit buffer, modified with 1 g/L (+) dextrose and 2.1 g/L sodium bicarbonate. A small section of the nerve complex on the distal end was carefully dissected away from the artery and peeled back. The distal artery was removed and the remaining nerve plexus was kept for recording. The middle and proximal portion of the nerve complex was left intact around the splenic artery with the vein. Surgical silk (5.0) was tied to clean nerve endings. Tissue was then transferred to a nerve conduction chamber. The proximal end of the plexus was pinned in the large bath while the other end was pinned down and placed over Ag/AgCl recording hooks in the smaller bath, through a grease gap. The chamber of the large bath was then perfused with fresh assay buffer, set to a middle bath temp of 27° C. A platinum wire in the bath was utilized as ground. The small bath was also manually filled with fresh Krebs-Henseleit buffer periodically.

Custom catheters were made prior to experiments in the range of 2.5-4 mm using silicone tubing with platinum rings (0.5 mm wide) wrapped circumferentially around the tubing (about 80% of the total circumference was exposed) and spot welded to Pt/Ir single strand wire internally. Sylgard was used to back fill the catheter. The custom catheter was inserted into the proximal splenic artery.

The recording bath was drained and a 1 Hz to 2 Hz square wave was applied across the stimulating electrodes to test for nerve activity. If active, the small chamber was filled with Krebs-Henseleit buffer and allowed to equilibrate for 30 min After checking viability one more time, the recording bath was drained and rapidly filled with paraffin oil and recording commenced. The multiplier on the voltage controlled current source was adjusted to achieve a range of current outputs. Current response curves were generated with pulse widths of 400, 800, 1600, 3200 and 6400 μsec using a monopole, 1 mm, 2 mm, 4 mm, and 6.5 mm spacing. A platinum wire in the bath was used as a common anode for the monopolar stimulation. Compound action potentials, bath temp, and stimulation timing and intensity level were recorded digitally.

After catheter stimulations, a 5000 μm Oscor cuff was positioned around the proximal splenic artery/nerve plexus with vein intact. Stimulation parameters were repeated as was done for the intravascular neurostimulation device.

Rectified AUC (modulus) wave responses for select pulse durations were normalized to the maximal response observed. Percent maximal responses plotted vs log current or log charge density were fit to sigmoidal 4-parameter dose response curves.

Results and Discussion

Figure 8A:
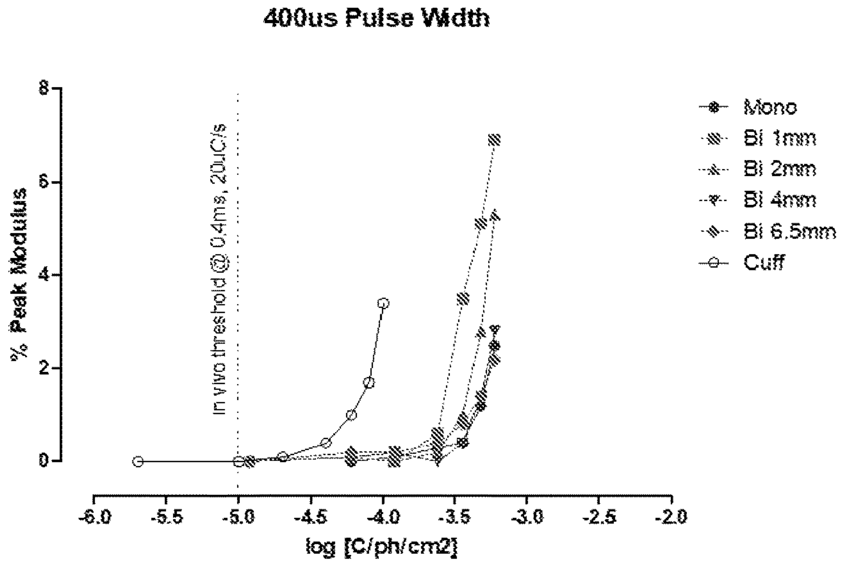
FIG. 8 illustrates an ex vivo comparison of charge density response curves of compound action potential recordings from pig SpN stimulation using either a cuff neurostimulation device or an intravascular neurostimulation device.
Figure 8C:
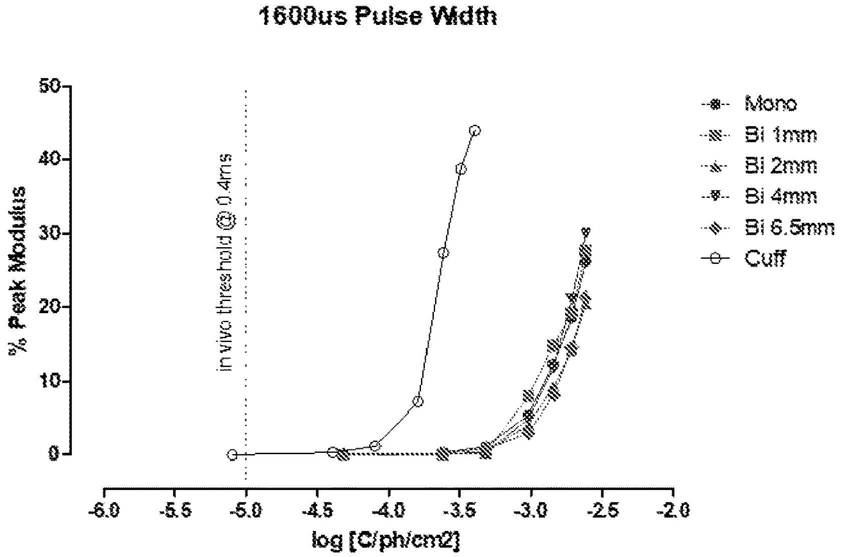
Figure 8E:
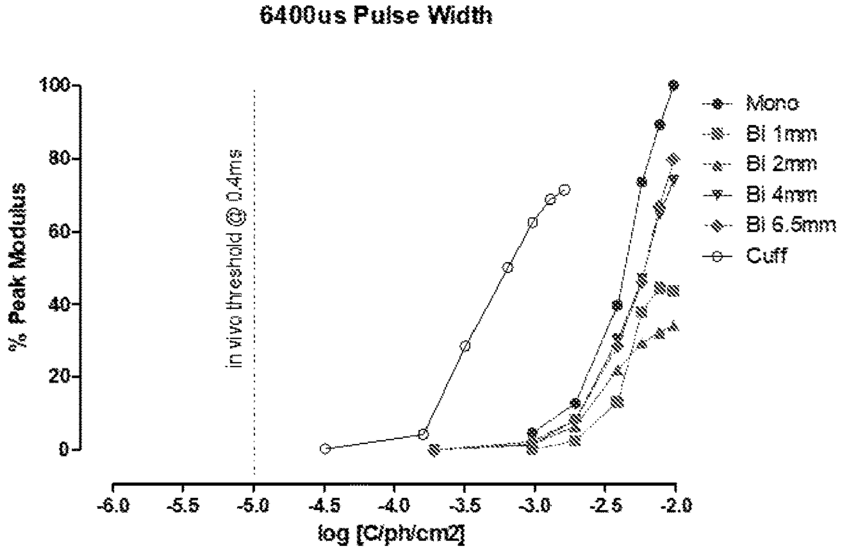
Figure 8B:
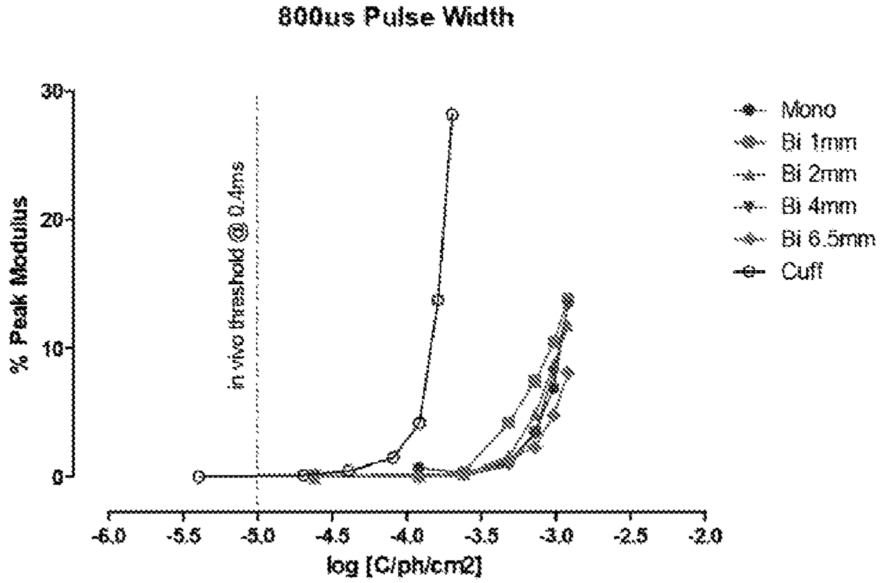
Figure 8D:
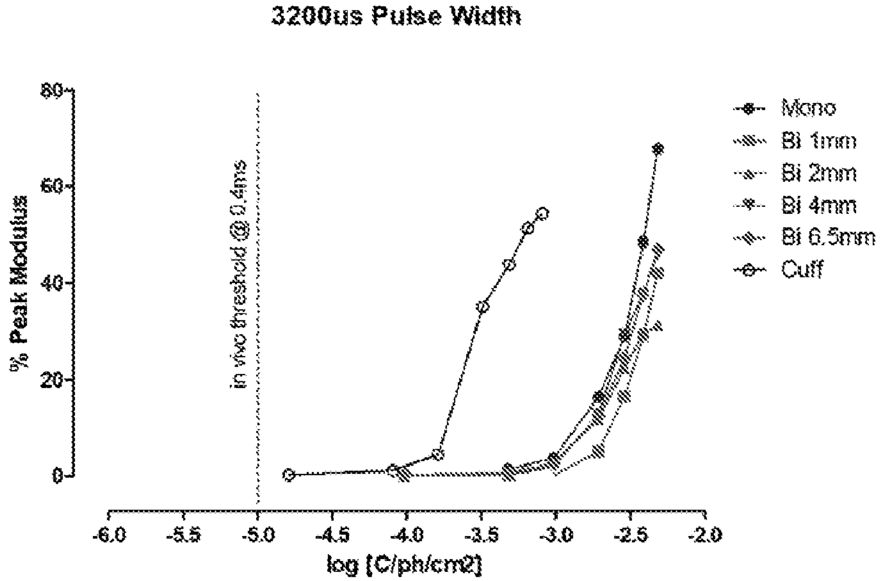

Current response curves are presented by pulse width with varying stimulation configurations with catheter and cuff (FIG. 7). Stimulation via intravascular device or cuff device reach thresholds at similar currents (approximately 10-20 mA). At low pulse widths, there appears to be a benefit to close proximity bipolar electrode placement (in other words, a smaller distance between electrodes on the catheter—see FIG. 7A) compared to wider electrode placement or monopolar stimulation (e.g. FIGS. 8B-C). This effect dissipates at higher pulse widths where monopolar outperforms other intravascular configurations (FIGS. 8D-E). Cuff stimulation is observed slightly left shifted from catheter stimulation at longer pulse widths. Currents were converted to charge density for each pulse width and electrode surface area (FIG. 8). Charge density plots are presented by pulse width as well as by inter-electrode distance (IED) spacing (FIG. 9).

On charge density, the extravascular approach yielded a more potent stimulation than intravascular stimulation (as evidenced by the left-shift in FIG. 8), but with similar efficacy to monopolar catheter stimulation. This is not unexpected, as the surface area of an extravascular interface will be larger than the surface area of an intravascular interface. Therefore, if the intravascular and extravascular yield the same current response curves, the charge density plots separate with extravascular response curves left of intravascular curves due to the larger extravascular surface area.

Figure 9A:
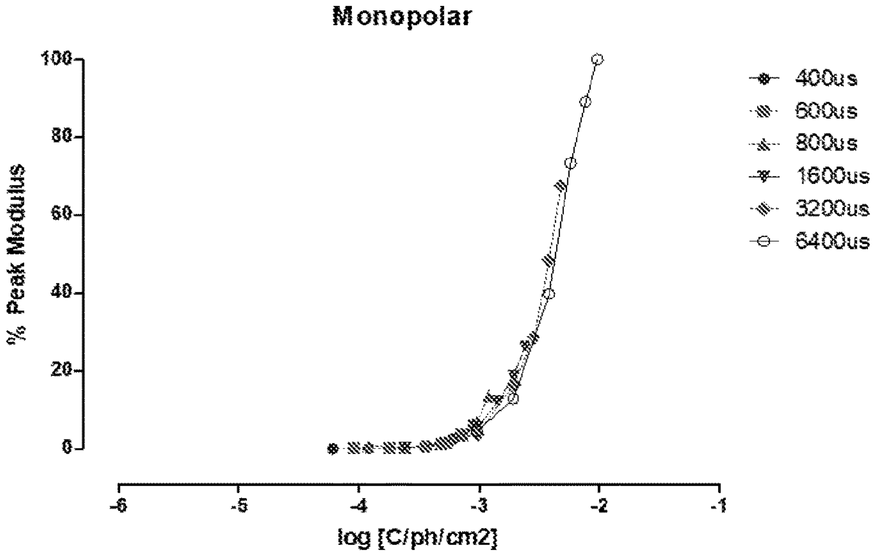
FIG. 9 illustrates an ex vivo comparison of charge density response curves of compound action potential recordings from pig SpN stimulation using either a cuff neurostimulation device or an intravascular neurostimulation device. Graphs show charge density requirement for a given spacing across multiple pulse widths.
Figure 9C:
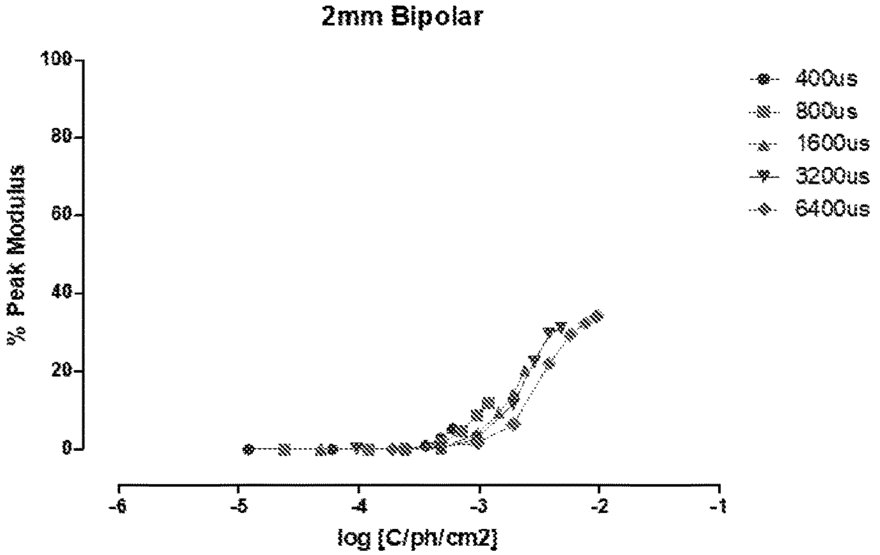
Figure 9E:
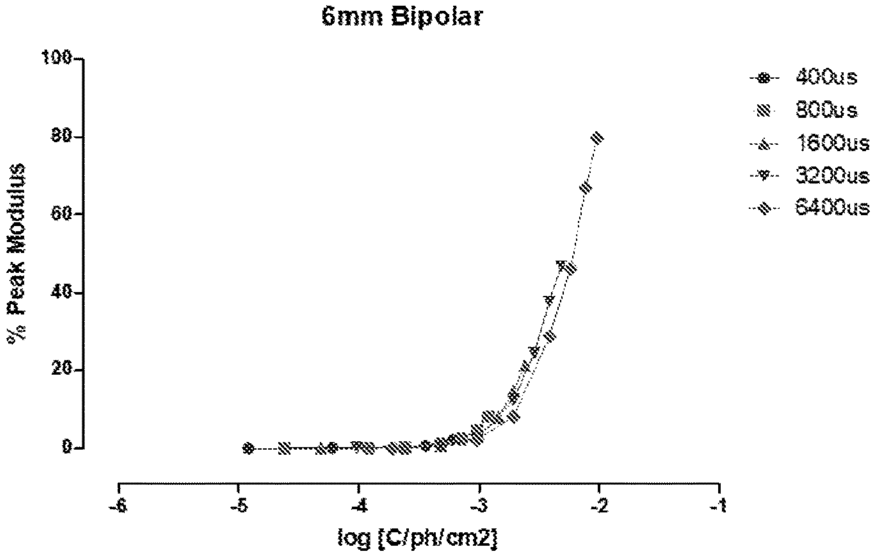
Figure 9B:
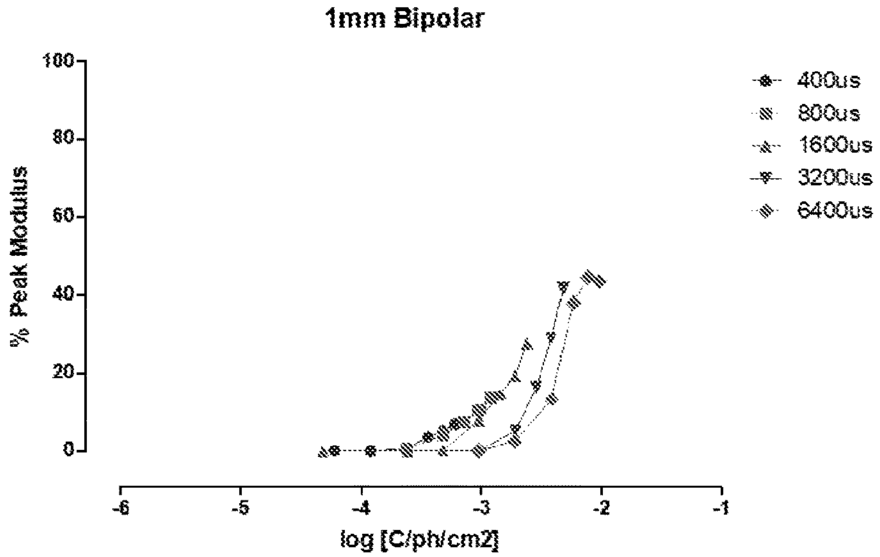
Figure 9D:
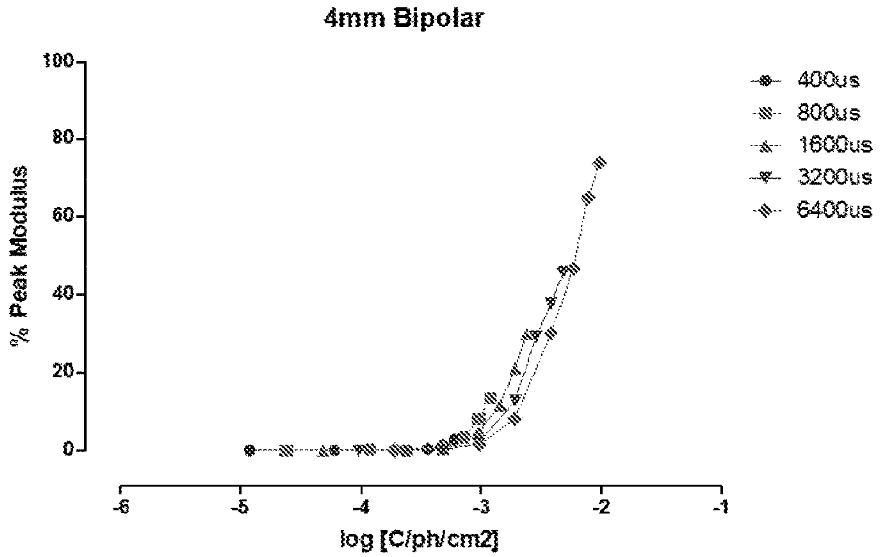
Figure 9F:
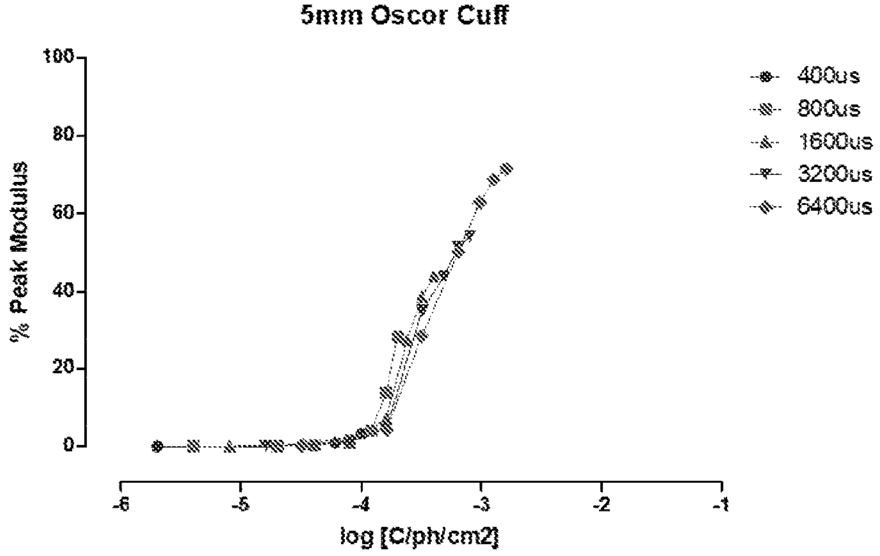

In general, efficacy of the CAP response increased with inter-electrode distance of the bipolar catheter. Wider electrode spacing yielded larger efficacy with monopolar providing the largest efficacy (FIG. 9). The 1 mm bipolar configuration was able to activate approximately 50% of the available CAP signal (FIG. 9B).

Summary

The experiments show that the SpN can be activated by both intravascular and extravascular electrical signals. Intravascular stimulation requires approximately ten times higher charge density over extravascular stimulation to achieve similar stimulatory responses. The % total recruitment of intravascular stimulation is positively correlated with the inter-electrode distance.

Study 3: Comparison of Intravascular and Extravascular Splenic Arterial Nerve (SpN) Stimulation in Pigs The inventors sought to determine with intravascular stimulation of the splenic nerve induced a similar physiological response compared to the extravascular stimulation observed in study 1.

Material and Methods

Studies were performed in two female 70 kg farm pigs.

Each day one animal was instrumented and the intravascular neurostimulation device rerouted into the splenic artery via access from the left femoral artery using fluoroscopy guidance.

An OSCOR RAM V1 perivascular cuff was also placed around the proximal portion of the splenic artery (just distal to the bifurcation from the celiac artery) as extravascular stimulation control. Blood flow probe was placed around the distal SpA just proximal to the left gastroepiploic artery.

Recording cuffs were placed on dissected fascicles of the SPN at different levels between the RAM and blood flow probe.

Several stimulations were tested while recording evoked compound action potentials (eCAP) and also recording physiological changes.

Changes in systemic blood pressure were monitored to determine nerve activation.

Results

Figure 10:
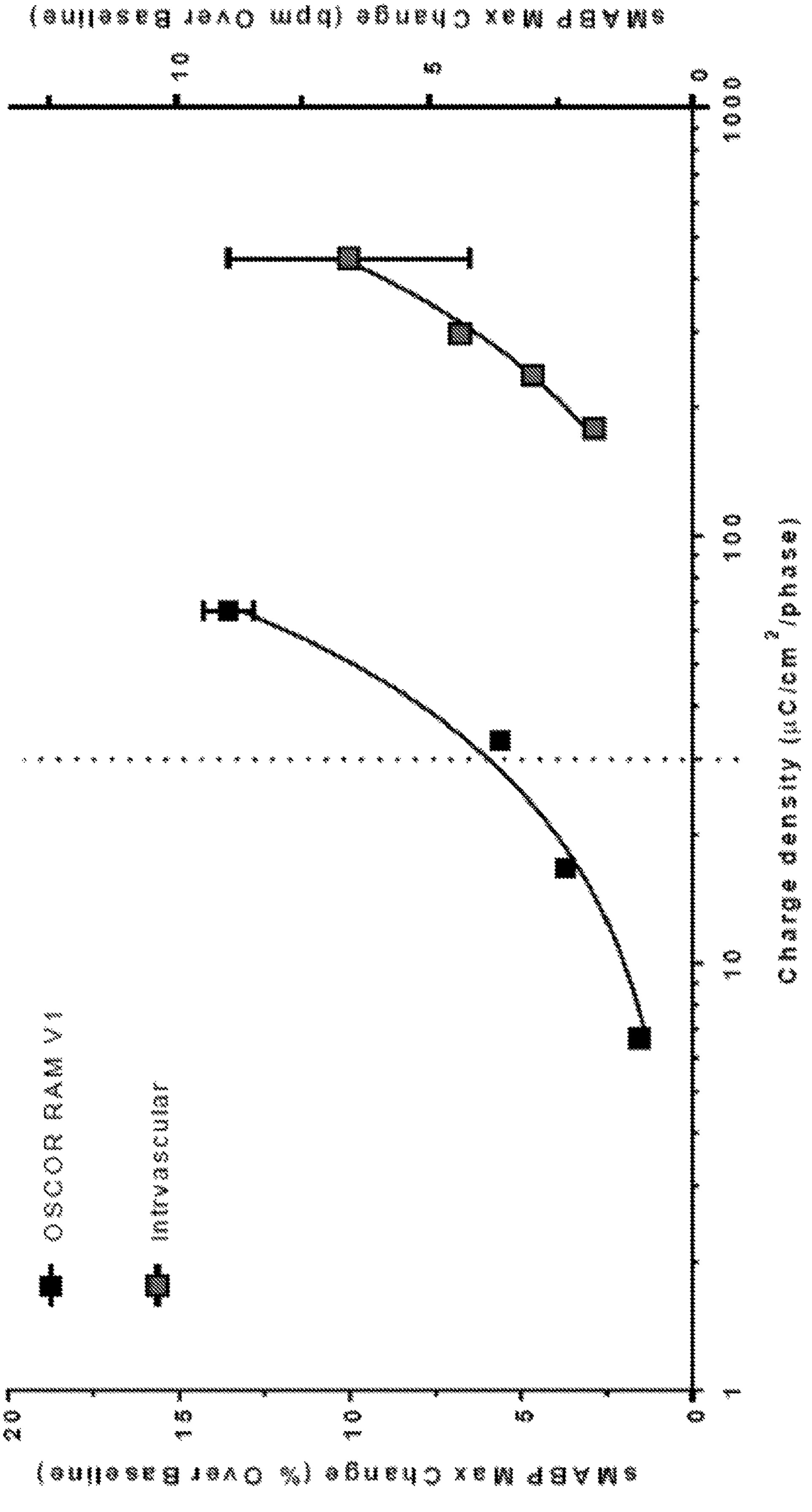
FIG. 10 shows that intravascular stimulation achieves a similar degree of change in sMABP compared to extravascular stimulation.

Stimulation was performed at a range of charge densities using both the intravascular and extravascular devices. Both approaches were able to yield similar physiological responses with respect to changes in systemic mean arterial blood pressure (FIG. 10). This shows that intravascular stimulation is effective in evoking similar physiological responses that were shown to be effective in prolonging survival of pigs in the endotoxemic model of study 1.

Study 4: Effects of Intravascular Splenic Arterial Nerve (SpN) Stimulation in Pigs

Materials and Methods

Animals

SpA Intravascular Stimulation was performed in 2 female 70Kg farm pigs.

General design

Each day one animal was sedated (Ketamine/midazolam), anesthetised (with Propofol) and maintained under Sevoflurane anaesthesia and artificial ventilation. The animal was then instrumented by placing introducing ports into both femoral arteries. The animal was also instrumented with a catheter into the tail artery (to monitor systemic arterial blood pressure), and a catheter into the right jugular vein (to administer fluids and monitor central venous pressure). An access port catheter was then placed into the right femoral artery and used to reroute the intravascular neurostimulation device into the SpA using fluoroscopy guidance.

In both days the stimulation of the splenic artery was attempted at proximal and distal levels along the SpA. In the first day only one version of the neurostimulation device (long anode) was used. In the second day both long and short anode versions were tested. SpN activation was assessed by monitoring systemic arterial blood pressure (sMABP) changes as well as heart rate (HR) and mean central venous pressure (mCVP).

In both pigs, 5000 IU of Heparin was administered prior to insertion of the neurostimulation device, to reduce risks of clot formation into the SpA.

Stimulation was applied using square, biphasic symmetric pulses delivered at 10 Hz over 30 s with 1 ms PW and the following amplitude range:

| | | | | | | | | | | |
|---|---|---|---|---|---|---|---|---|---|---|
| Charge Density (μC/cm2) | 100 | 150 | 200 | 250 | 300 | 350 | 400 | 500 | 600 | 650 |
| Pulse duration (ms) | 1 | 1 | 1 | 1 | 1 | 1 | 1 | 1 | 1 | 1 |
| Current Amplitude (mA) | 6.6 | 10 | 13.3 | 16.6 | 20 | 23.3 | 26.6 | 33.3 | 40 | 43.3 |

Figure 11:
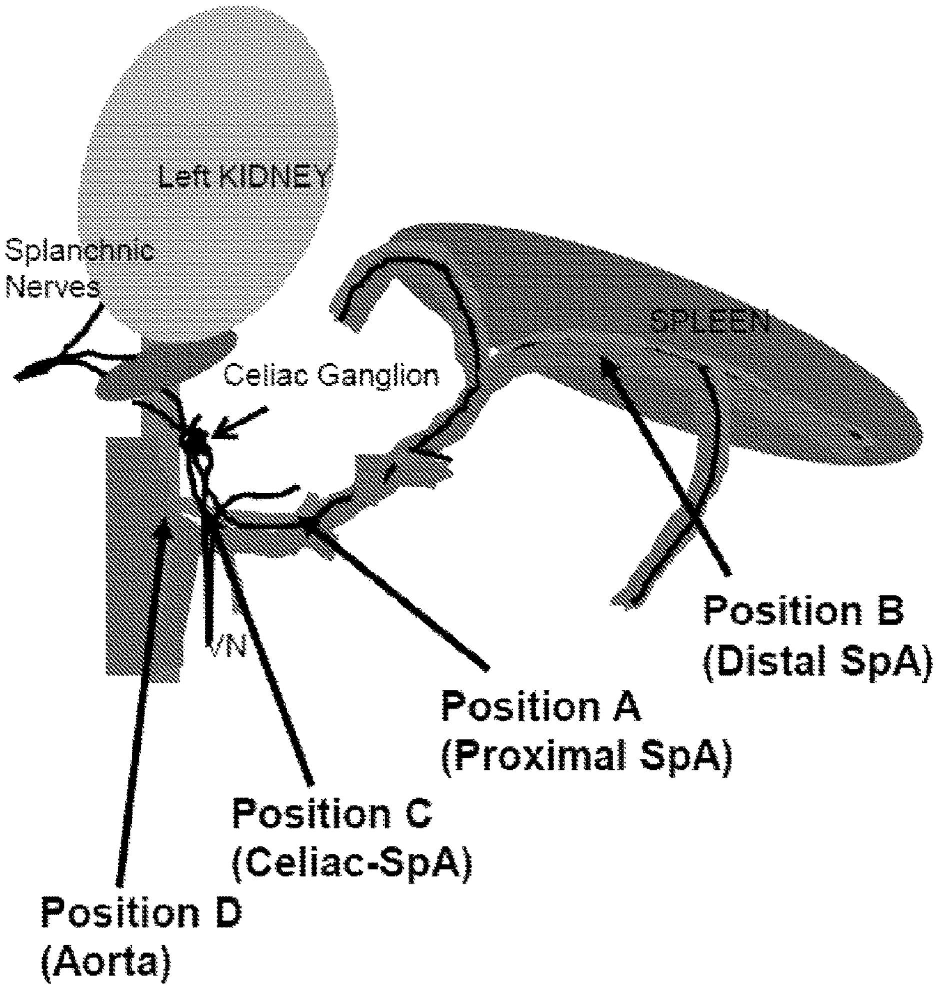
FIG. 11 illustrates the response evoked in vivo by intravascular innervation at Positions A, B, C and D.
Figure 11:
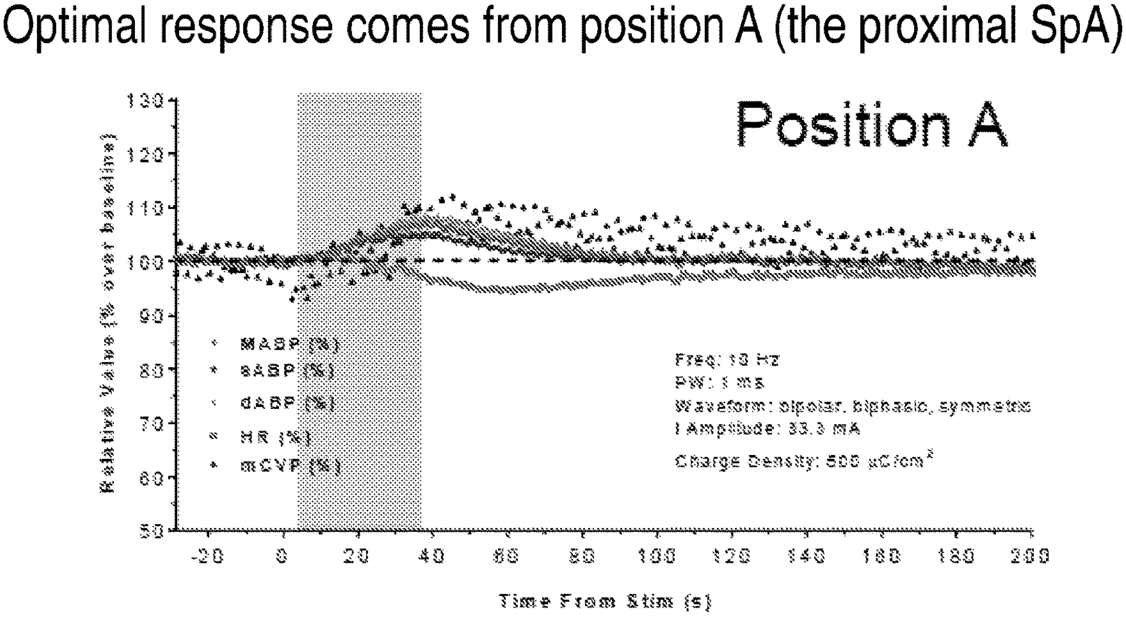
Figure 11:
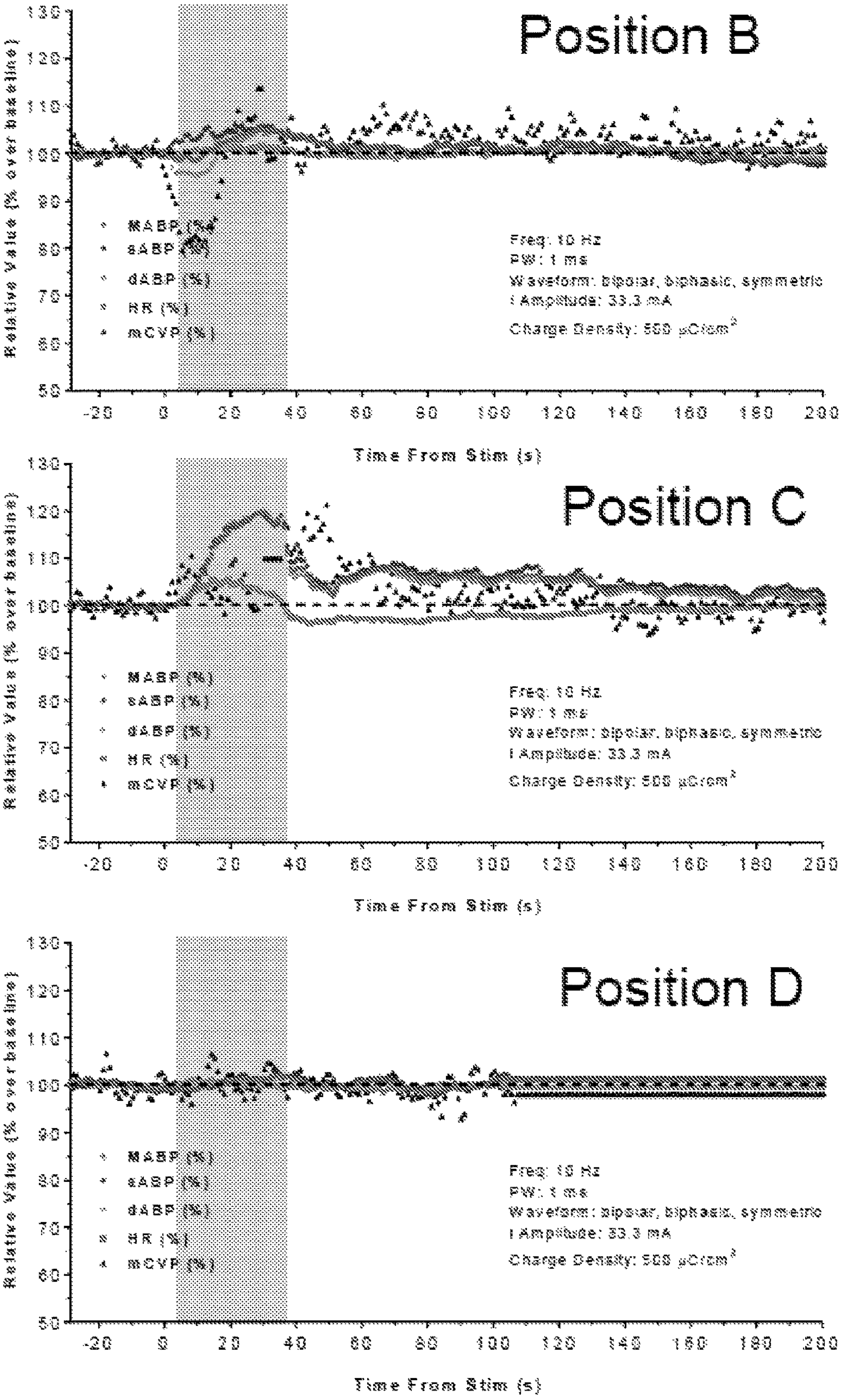

Response to stimulation was tested at the four positions shown in FIG. 11 (position A—the "proximal" SpA (i.e. closer to the celiac trunk than the spleen); B—the "distal" SpA (i.e. closer to the spleen than the celiac trunk); C—Celiac artery); and D—Aorta).

Results and Discussion

Figure 12A:
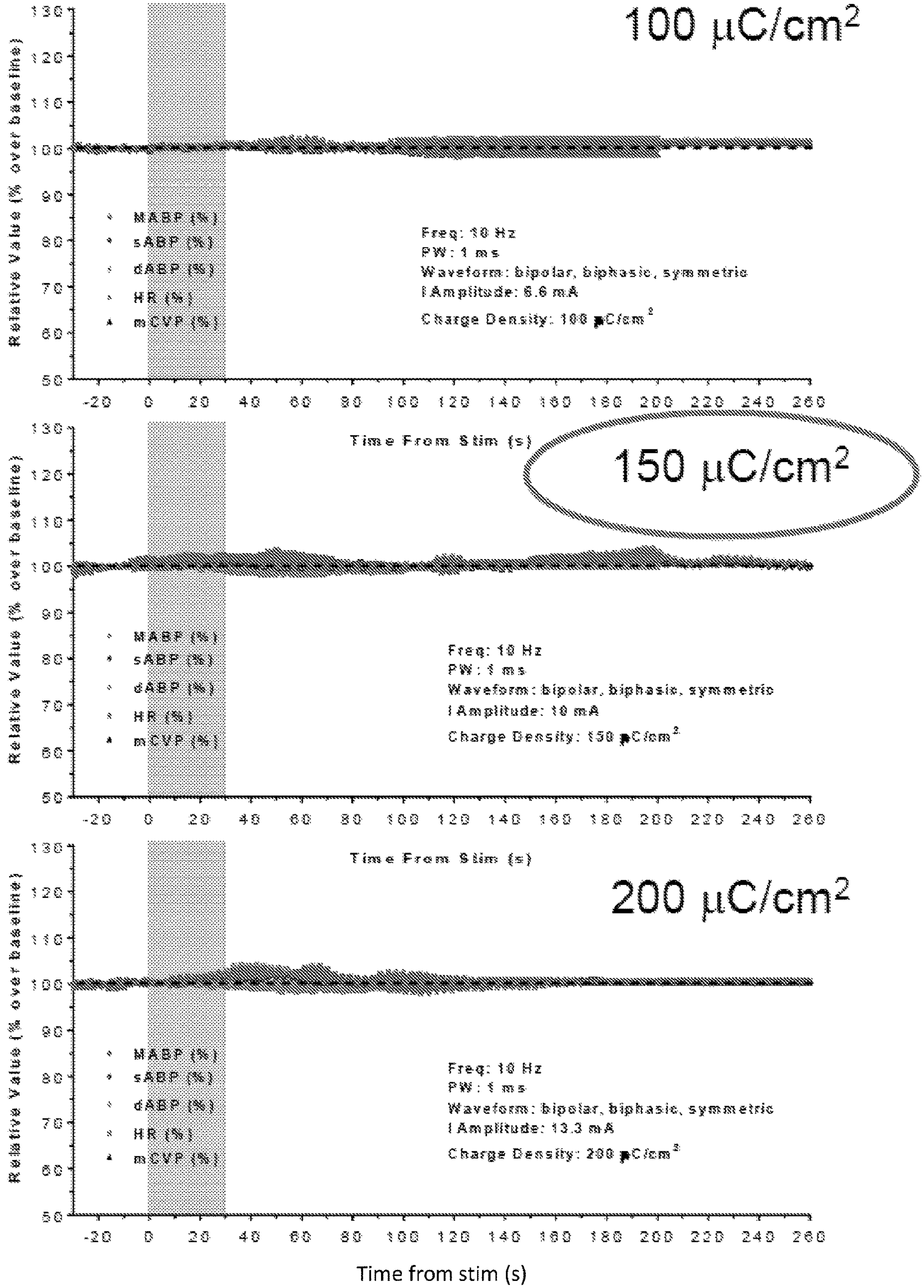
FIG. 12A illustrates that response evoked by innervation at position A is charge density-dependent (A).
Figure 12A:
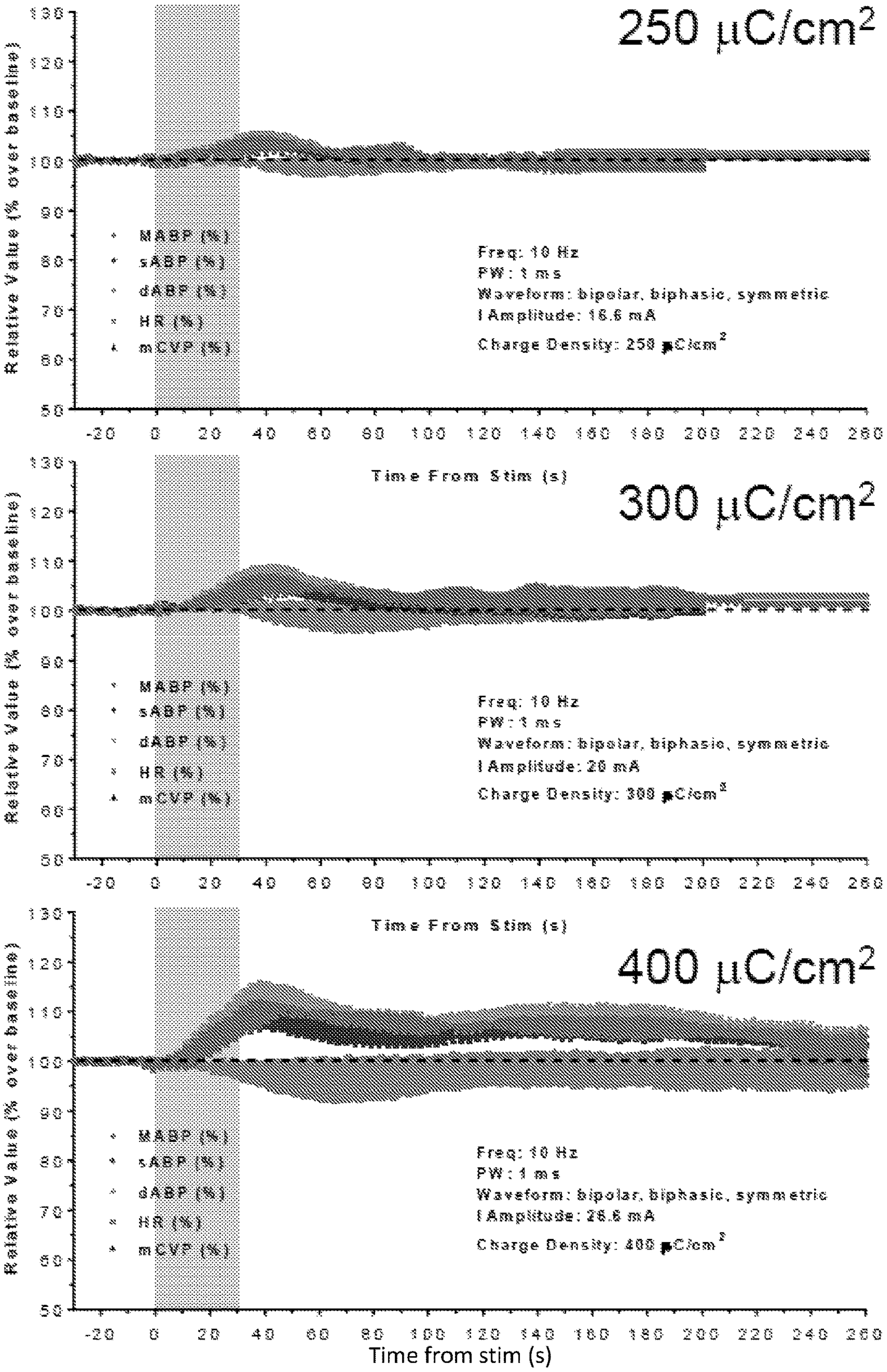
Figure 12B:
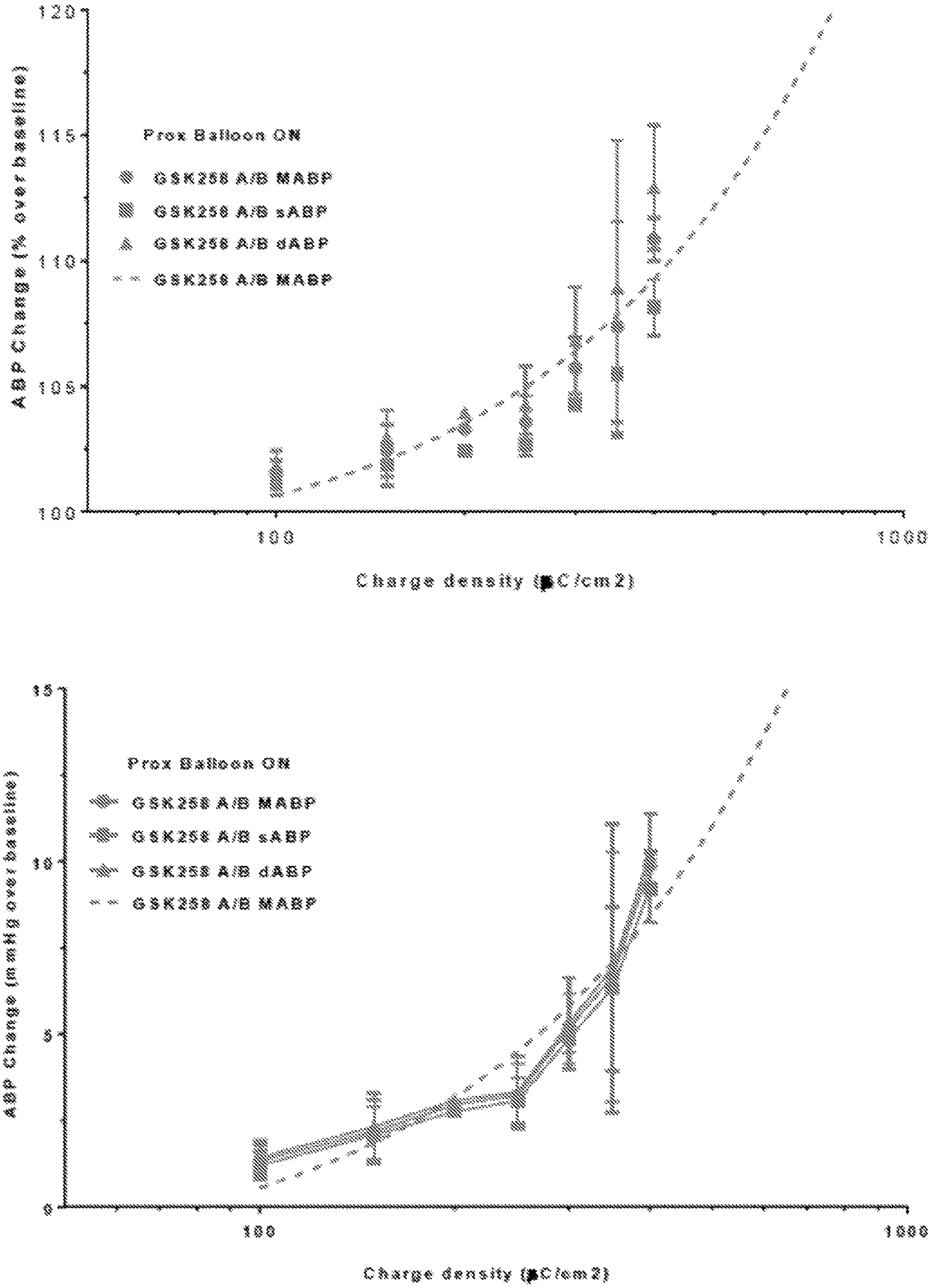
FIG. 12B summarises the response evoked by innervation at position A using different charge densities.
Figure 13:
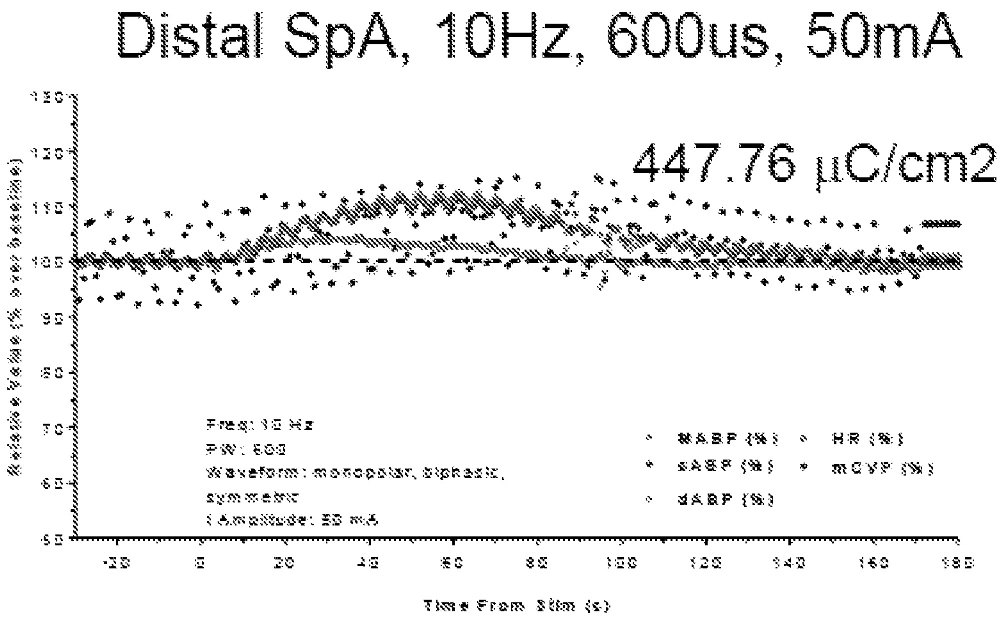
FIG. 13 shows that application of an electrical signal using an intravascular device at the distal SpA generates a physiological response.

FIG. 11 shows that an in vivo change in systemic mean arterial blood pressure (MABP or "sMABP") during the application of an intravascular electrical signal is obtained when a signal is applied at position A. FIG. 12 shows that application of charge densities of 150 $\mu C/cm^2$ and above at position A evoked a response in sMABP similar to that observed when using the extravascular cuff electrode disclosed in Study 1 (see FIG. 7A). Changes in sMABP on application of a range of charge densities are shown in FIG. 12B. The use of either 0.5 ms or 1.0 ms pulse width (PW) did not significantly alter the amplitude of the response (data not shown). Another study observed that physiologically-relevant alterations in sMABP can also be achieved when applying the intravascular electrical stimulus at the distal position (FIG. 13). Higher charge densities were required. This provides the benefit of being able to more rapidly tune the physiological response achieved in vivo by re-positioning the position of the device. Such rapid changes are not as readily achievable when using extravascular cuff-based electrodes.

Figure 14:
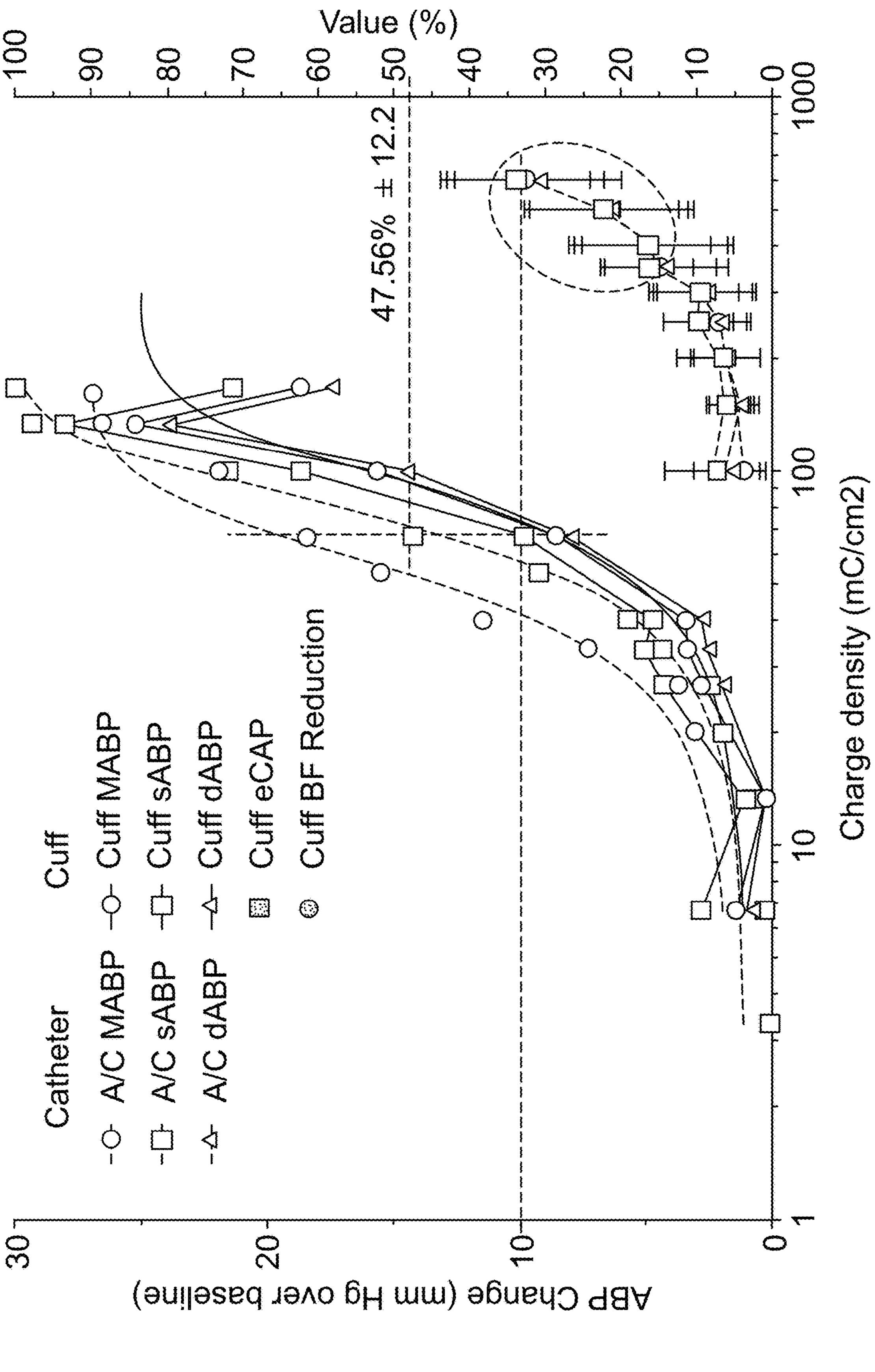
FIG. 14 illustrates that a charge density of 600 $\mu C/cm^2$ when applied using the neurostimulation device of the invention evokes a similar eCAP (on the right axis) response to the optimal charge density applied by the cuff neurostimulation device employed in Study 2 corresponding to about 50% activation of the splenic nerve.

The results show that intravascular stimulation of the SpN via the use of an intravascular neurostimulation device is effective in achieving clinical relevant alterations in sMABP. The amplitude of the alterations achieved by the cuff electrode are equivalent to the amplitude changes achieved by the intravascular neurostimulation device tested in Study 3 (FIG. 14). Stimulations at 1 ms PW and 40 mA using the intravascular neurostimulation device (corresponding to a charge density of 600 $\mu C/cm^2$) results in a mean 10 mmHg increase in systemic MABP, which corresponds to about 50% eCAP stimulation. Efficacy with a cuff electrode was achieved with 20-30% eCAP stimulation. Thus, the intravascular neurostimulation device of the invention may be used to obtain the pro-survival effects in this in vivo LPS animal model. Hence, stimulation of the neural activity of splenic nerves using the neurostimulation device of the invention may also be particularly useful for treating acute medical conditions.

Moreover, the position of the device can be more easily altered in vivo to ensure the desired physiological response is obtained.

Study 5: Ex-Vivo Electrophysiological Study of Human Splenic Nerves

The objective of this study was to estimate indicative stimulation parameters of human splenic nerves in order to de-risk and optimize the biological efficacy and reproducibility of stimulation parameters of the electrical signal for use in humans, in particular for stimulation of a human splenic nerve. The study was performed using ex-vivo using human splenic samples.

Figure 15A:
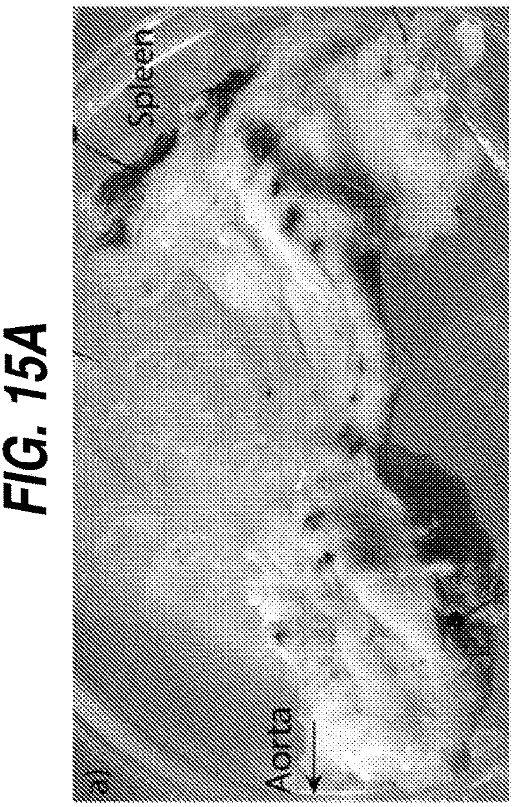
FIG. 15 shows (A) an example of the human splenic tissue. The dark stained spots on the sample indicate the splenic artery with aorta towards the left end, and spleen on the right end of the sample (for orientation). (B) shows placement of a peri-arterial cuff around the neurovascular bundle (I) and placement of a smaller diameter cuff around a few nerves (III). The nerve is dissected, placed in a bath with Kreb's solution, and traced all along till the end of the sample, where the hooks are placed to record compound action potentials (C, III). (D) shows a conceptual sketch of tissue with the cuff, and hook placement, and (E) shows an example of an eCAP observed on the oscilloscope.

Materials and Methods FIG. 15A shows an example of fresh splenic sample from a 63-year-old female donor (it is noted that the range of age of donors making up the data described below is 23-63 years). The sample, approximately 15 cm in length, was placed in a petri dish, and the splenic neurovascular bundle (SNVB) was then carefully surgically isolated from excess adipose tissue and splenic vein under a microscope. The dots on the sample indicates the top part of the splenic artery used in order to maintain the orientation of the sample. The sample was tortuous and seemed to have loops. A few splenic nerves were carefully isolated distally for the purpose of recording eCAPs.

Figure 15C:
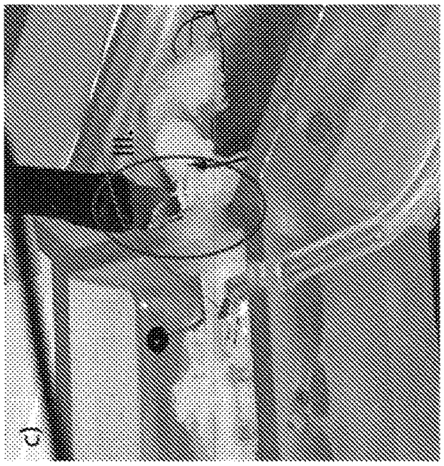
Figure 15B:
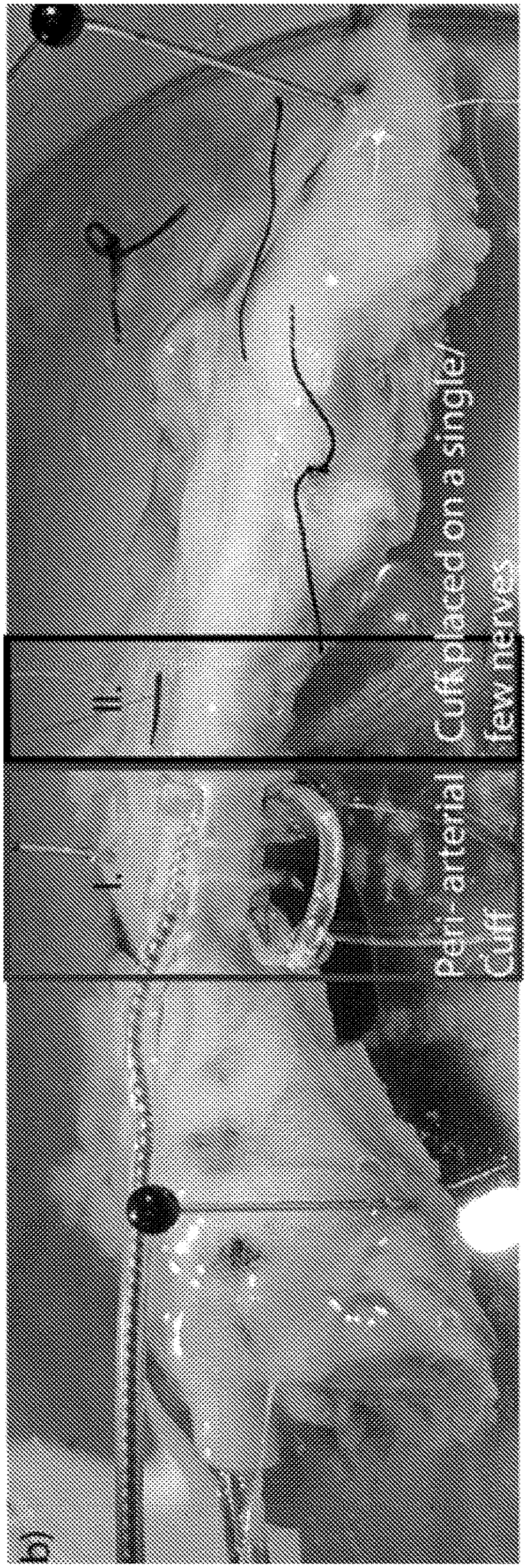
Figure 15D:
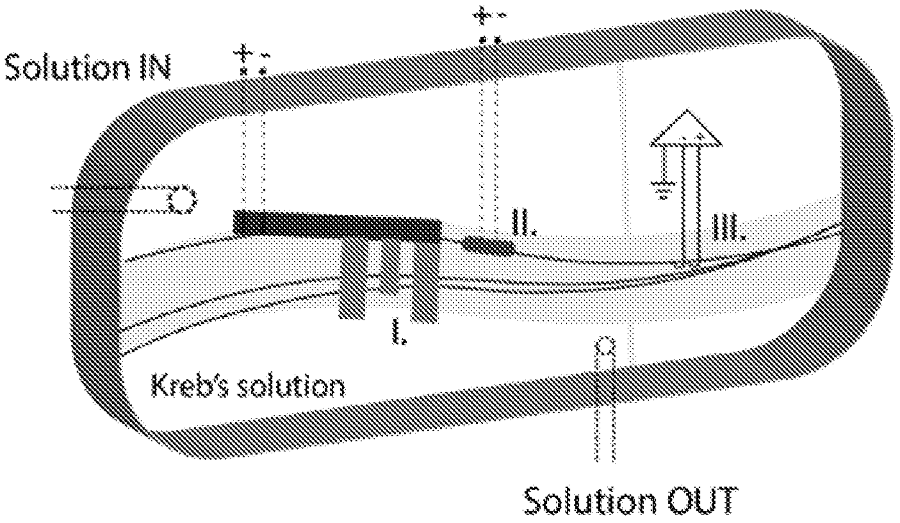
Figure 15E:
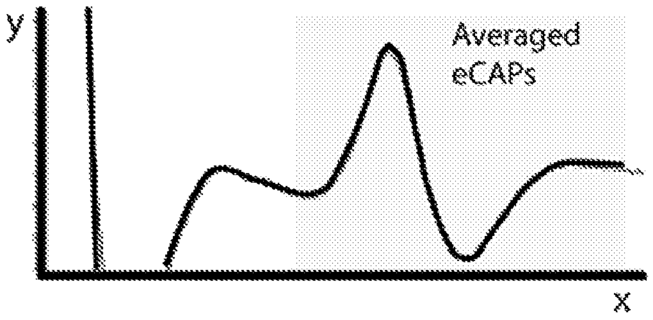

An isolated fascicle was used as a control and cuffed with a smaller diameter Cortec Cuff electrode (500 μm diameter) for recording and stimulation, as shown in FIG. 15B, (II). A bigger periarterial cuff of approximately 6 mm diameter was placed on the neurovascular bundle (see FIG. 15B, (I)). Subsequently, the tissue with the cuff was moved into the recording chamber which was constantly circulated with fresh, oxygenated and warm Kreb's solution (34-36 degrees Celsius). The stimulation cuffs were connected to a DS5 instrument (current stimulator) and recording cuff was connected to a bioamplifier (CWE, USA) as indicated in the schematics (see FIG. 15C, FIG. 15D). For stimulation, a bipolar configuration with monophasic pulses were used. The schematics of the evoked compound action potential is represented in FIG. 15E.

Results

The nerve viability on isolated nerves was verified with a smaller 500 μm cuff electrodes, used as a control. The current strength-pulse width results from stimulation in eight human SNVB samples stimulated with 6 mm cuff demonstrates that the use of a 2 ms pulse width permits a 2.5- to 3-fold reduction of the stimulation threshold of pulse height for a 2.5-fold increase of pulse width i.e. from 0.4 to 2 ms (see FIG. 16A).

Figure 16A:
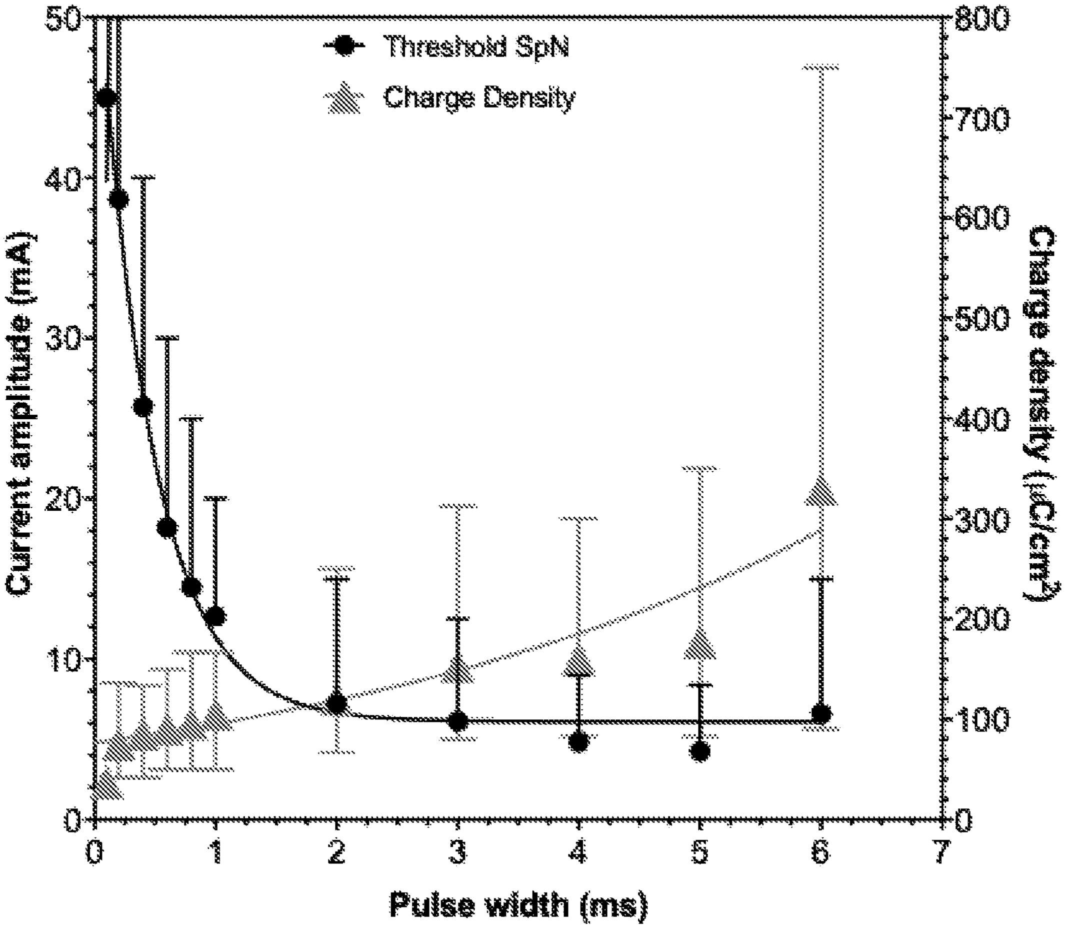
FIG. 16 shows results from an ex-vivo electrophysiological study of the human splenic samples. (A) shows current amplitude-pulse width and charge density-pulse width curves. The error bars demonstrates the range, and the lower bar of the range is not presented on the graph. (B), (C), and (D) show recruitment graphs for 0.4 ms, 1 ms and 2 ms pulse widths respectively.

Interestingly, 400 μs pulse width, which seems to be a more suitable stimulation parameter in the porcine in-vivo study, did not experimentally prove preferable in the case of human ex-vivo and in-silico tissue preparations. The mean pulse height from N=6 in an acute porcine study was approximately 3.5mA, whereas in humans it was found to be at an average seven-eight times higher at approximately 25 mA. The reason why trade-off between pulse width and pulse height is important is to inform a preferable output level for implantable stimulator design and electrode charge injection capacities. With reference to FIG. 16A, 3 ms also seems a suitable pulse width, however, there is an increase in charge density with negligible decrease in pulse-duration. A significant increase in charge density is observed at and above 5 ms.

Figure 16B:
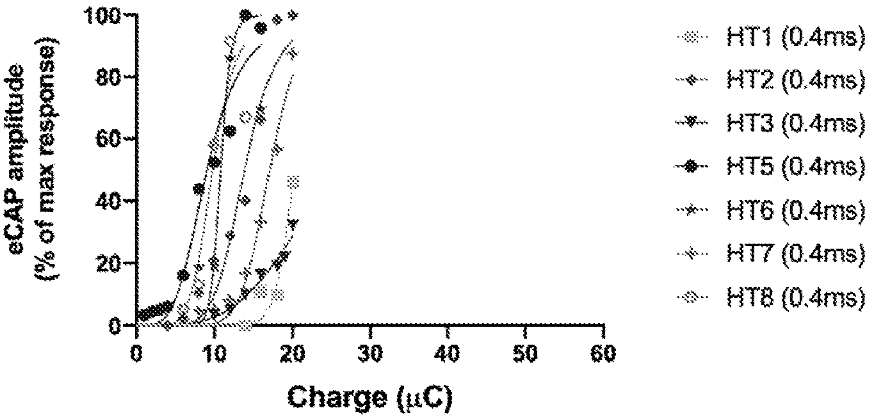
Figure 16C:
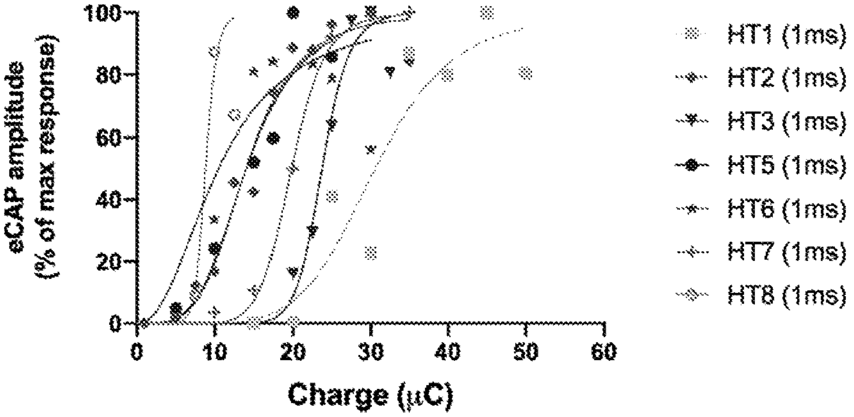
Figure 16D:
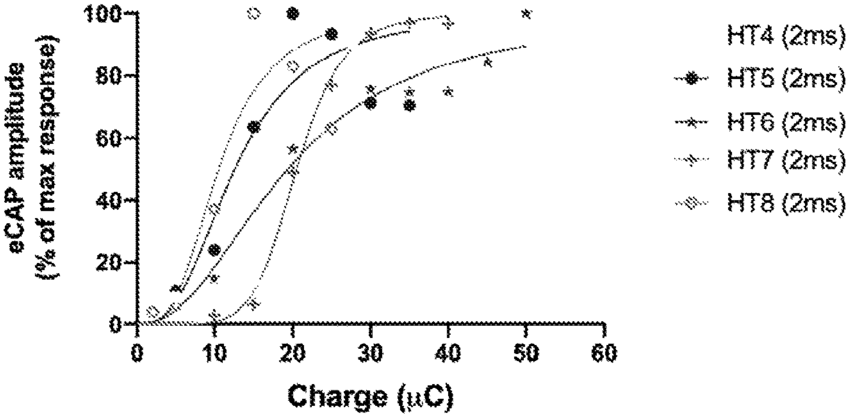
Figure 21:
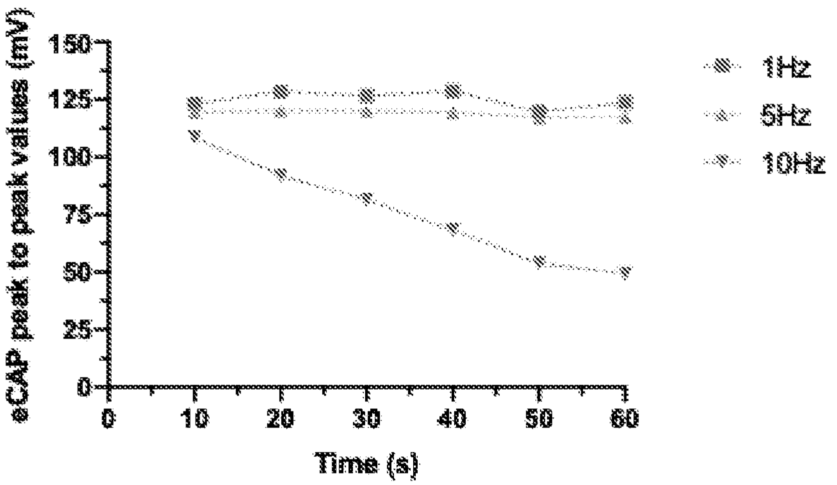
FIG. 21 shows comparison of frequency. An increase in frequency from 1 Hz to 10 Hz indicates a reduction in eCAP amplitude and is indicative of nerve fatigue, thus re-confirming porcine data assumptions on frequency.

An increase in frequency from 1 Hz to 10 Hz indicates a reduction in eCAP amplitude and is indicative of nerve fatigue (see FIG. 21). Thus in this instance re-confirming porcine data assumptions on frequency. Nerve recruitment curves from individual donor samples at different pulse width of 0.4, 1 and 2 ms are illustrated in FIG. 16B, 16C, and 16D respectively. The compound action potentials are normalised with respect to the maximum eCAP amplitude response recorded on the oscilloscope. DS5 instrument has a limitation of 50 mA in amplitude, which was not enough to recruit 100% nerves at 0.4 ms (as seen in FIG. 16B). Thus, moving to 1 m and 2 ms pulse width effectively proves to be a more ideal trade-off. It is estimated that the charge requirements in human ex-vivo sample for 100% axon recruitment can be as high as 400 $\mu C/cm^2$ (assuming a 0.12 $cm^2$ total electrode surface area) as can be seen in FIG. 16D. Based on assumptions of fibrotic encapsulation modelling, and the effects we have seen in pre-clinical animal models, a right shift effect is observed (as also seen in literature such as in W M Grill J T Mortimer. Electrical properties of implant encapsulation tissue. Annals of biomedical engineering, 22:23-33, 1994) by factors of ×1.5, ×2 and ×3, for example, on the charge requirements in chronic. This can be seen in FIG. 17, where our estimation of charge requirements in chronic clinical scenario could be as high as approximately 100 μC (850 $\mu C/cm^2$). A similar trend of charge requirements is observed from in-silico results for both 0.4 and 1 ms pulse width.

Discussion

It was found that for increasing pulse width, particularly pulse widths greater than 1 ms, a decrease in the pulse height threshold needed to trigger an action potential in a human splenic nerve is observed. This is a surprise based on the porcine model which showed the more suitable pulse width to be far lower, at 0.4 ms. Lower pulse height thresholds are generally desirable because the biological efficacy and reproducibility of the stimulation parameters for use in humans is improved.

It has also been found that at a pulse width of 3 ms or above (3-5 ms shown in data) there is no further decrease in pulse height, whereas there is an increase in charge density. Therefore, the strain of the electrodes outweighs the benefits seen in the stimulator beyond a pulse width of 3 ms. Between 2 ms and 3 ms, there is a negligible decrease in pulse height threshold but the amount of charge density required increases. Therefore it may be desirable to use a pulse width of less than 3 ms in humans Pulse width around 2 ms offer an optimal trade-off between ensuring a low charge density being required, and a low pulse height being required for the stimulation of a human splenic nerve.

Figure 17:
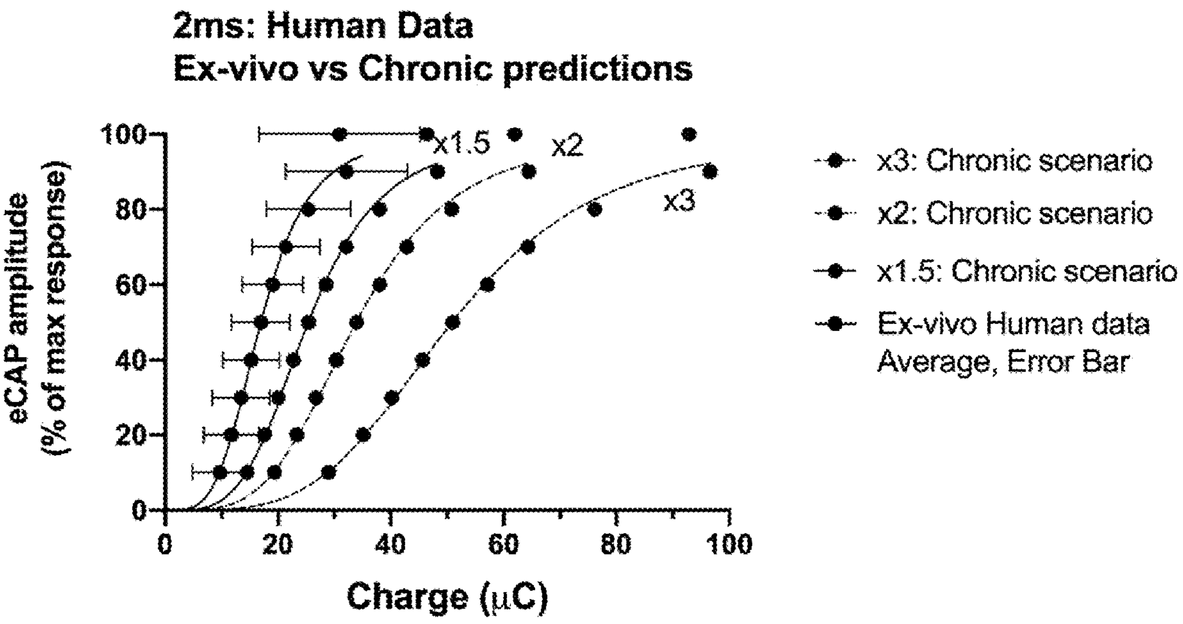
FIG. 17 shows predictions of recruitment curves for a human splenic nerve in chronic scenarios based on human ex-vivo data at 2 ms pulse width. The y-axis represents the eCAP amplitude as a percentage of maximum response and the x-axis represents the total charge (μC) injected into the human splenic nerve.

It is estimated that the charge density per phase requirements in human ex-vivo sample for 100% nerve recruitment can be as high as 400 $\mu C/cm^2$. However, it is expected that for chronic stimulation, the formation of scar tissue may reduce the nerve recruitment by a factor of between 1.5 and 3. FIG. 17 shows the 2 ms pulse width human ex-vivo data multiplied by a factor of 1.5×, 2× and 3×, and the change in recruitment based on the charge injected into the human splenic nerve. FIG. 17 suggests that up to 100 μC charge may need to be injected for recruitment of 100% nerves in humans in chronic scenario. This equates to a charge density per phase of approximately 850 $\mu C/cm^2$ based on a 0.12 $cm^2$ total electrode surface area. Accordingly, the charge density per phase required in order to achieve 100% recruitment of the human splenic nerve is expected to be up to approximately 850 $\mu C/cm^2$ for a pulse width of 2 ms.

Study 6: Human Chronic Model Stimulations

The purpose of this study was to determine the biological effect varying of interphase delay and pulse width. The study was conducted using a human chronic model simulation.

Materials and Methods Hybrid electromagnetic (EM) and neuronal simulations were used to predict axonal recruitment in two representative image-based and 3D computational neurostimulation models of human and porcine splenic neurovascular bundle, for multiple variations of dielectric parameters of the nerve bundles, stimulus waveforms (0.4 ms, 1 ms and 2 ms biphasic pulses), and fibre diameters (0.5-1 mm). One representative cross section histological image of splenic neurovascular bundle for each species was segmented using iSEG within Sim4Life platform. Tissues were differentiated to identify vessel wall, blood, extra fascicular medium—internal and external to the electrode—and the endoneurium tissue within fascicles. The segmented tissue surfaces were extruded in 3D using extrusion functionalities. The bundle models were combined with cuff electrodes geometries, were surrounded by saline solution tissue to mimic experimental conditions, and fascicles were populated with multiple parallel axonal trajectories randomly distributed within each fascicle cross section.

EM simulations were performed using a FEM solver in the quasi-static approximation that handles anisotropic electric tensors conductivity and support thin layer settings. FEM calculations were executed on unstructured meshes created on the model geometries, built within Sim4Life using adaptive criteria and mesh quality adjustment. The meshes were edited to extract patches at the electrode surface to assign flux density boundary conditions, and at the interfaces between fascicles and interfascicular tissues to define thin layers mimicking the perineurium. In order to execute transient neuroelectric simulations for a given set of stimulation conditions (fibre diameters, pulse waveform, temperature), the range of parametrised axon electrophysiology in Sim4Life was extended by a c-fibre model (Sundt Model) completing the functionality required to stimulate nerves featuring distribution of unmyelinated c-fibres with arbitrary fibre diameters. Sim4Life functionalities such as the automatic sweeping and titration procedure were used to quantify stimulation thresholds (e.g. the pulse height threshold), investigate strength-duration (SD) curves and perform sensitivity analysis e.g. with respect to dielectric properties of tissues or pulse parameters. The creation of neuroelectric models, the creation and the setup of hybrid EM-neuronal simulations, and the post-processing of the results was assisted by 1) Python scripts facilitating the flexible, parametrised generation of functionalised nerve models, 2) the assignment of heterogeneous tissue properties and anisotropic electrical conductivities, 3) the creation of mesh and its editing, 4) the distribution of fibre models within fascicles, 5) the assignment of electrophysiological behaviour as well as for automised post-processing analysis, e.g. the quantification of stimulation thresholds, extraction of recruitment curves, identify location of spike initiation and latencies (time of first spikes) with respect to stimulus pulse-shape.

The image-based models of neurovascular bundles developed were adapted to include fibrotic tissue surrounding the electrodes and the insulating silicone to mimic the presence of a post-implantation fibrotic tissue. Hybrid EM-neuronal simulations were used to calculate the neuroelectric responses of electrophysiological models of individual unmyelinated C-fiber axons inserted within the fascicles of the bundles to quantify the stimulation thresholds (e.g. pulse height threshold) for initiation of the action potentials. From the calculated thresholds, recruitment curves were plotted for both acute and the chronic scenarios based on biphasic waveforms with different pulse durations (τdur) and interphase delays (τinter). The results are based on the following principal assumptions: (i) the dielectric properties, the structure, and the composition of the fibrotic tissue are uniform across all simulations; (ii) the fibrotic tissue is homogeneous and isotropic; (iii) there is no distinction between the fibrotic tissue formed around the electrodes vs. the silicone; (iv) the position of the fascicles is kept constant moving from acute to chronic scenario. The diameter of the neurovascular bundle is also kept constant and 0.5 mm of interfascicular tissue has been replaced by fibrotic tissue layer.

Results

Figure 18:
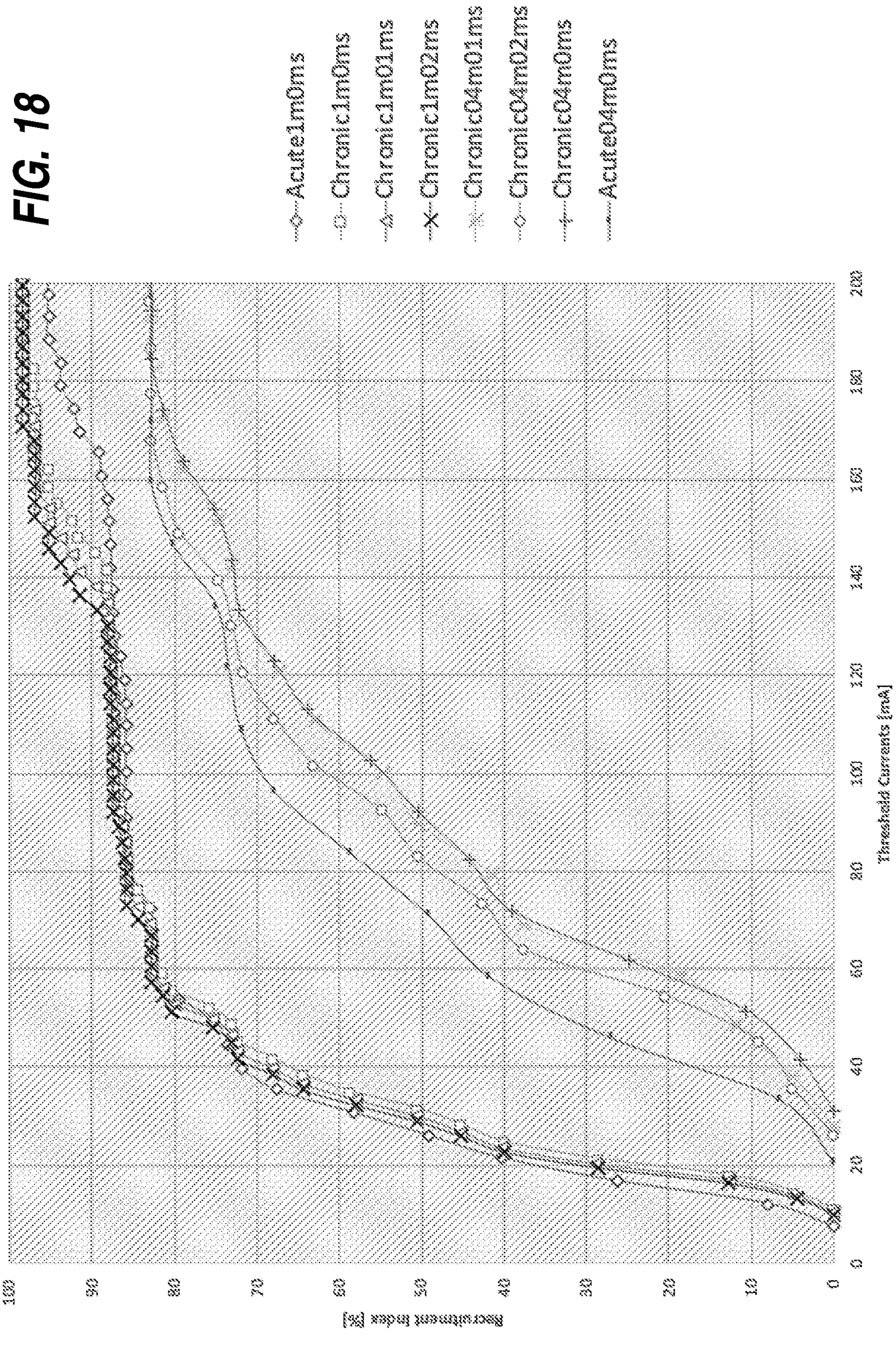
FIG. 18 shows comparisons of recruitment curves calculated for the human model for acute and chronic stimulations with different parameterisations of biphasic pulse waveforms, in particular different pulse widths (0.4 ms, 1 ms) and different interphase delays (0 ms, 0.1 ms, 0.2 ms). In the key (e.g. 'Chronic1m0ms'), the word represents the type of stimulation (e.g. 'Chronic'), first number represent the pulse width in ms (e.g. '1' ms), and the second number represents the interphase delay in ms (e.g. '0' ms).
Figure 20:
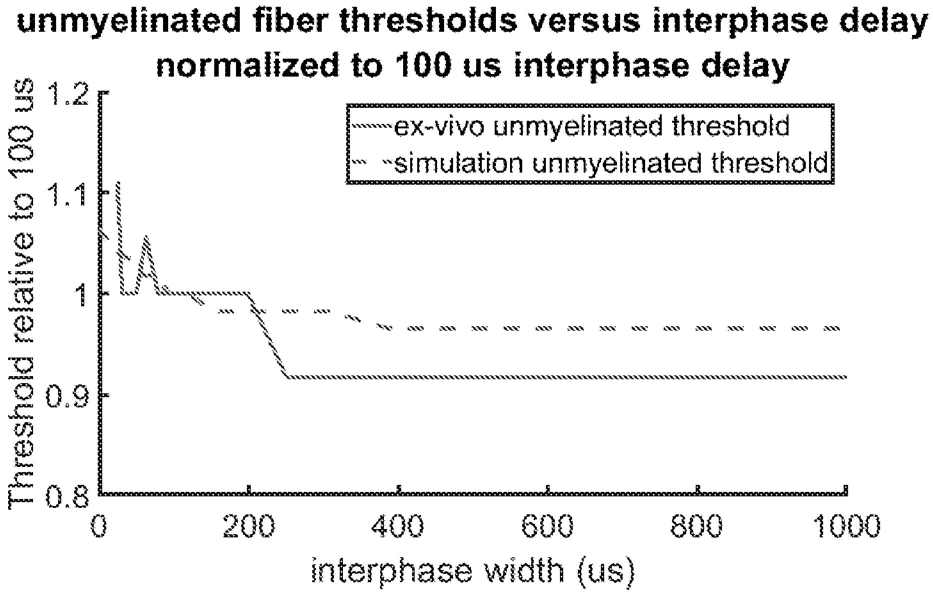
FIG. 20 shows unmyelinated fiber pulse height thresholds verses interphase delay normalised to a 100 μs interphase delay. The y-axis represents the threshold relative to an interphase delay of 100 μs and the x-axis represents the interphase delay (μs).

FIG. 18 shows comparisons of the recruitment curves calculated for the human model for acute and chronic stimulations with different parameterisations of the biphasic pulse waveforms. For the chronic case, it was found that the presence of the fibrotic encapsulation increases the pulse height threshold required to trigger the creation of an action potential, with the increase for a fixed pulse duration being smaller for larger interphase delays. The increase in pulse height threshold is dependent on the specific parameters of the biphasic pulse waveform. For instance τdur=1 ms, the pulse height threshold increase is 37% when τinter=0 ms (simulations Acute1ms0ms vs. Chronic1ms0ms) but is 29% when τinter=0.2 ms (simulations Acute1ms0ms vs. Chronic1ms02ms). Similar results were found for τdur=0.4 ms: the pulse height threshold increase is 49% (simulation Acute04ms0ms vs. Chronic04ms0ms) vs. 27% with τinter=0.2 ms (Acute04ms0ms vs. Chronic04ms02ms). The results for 0.1 ms interphase have also been demonstrated in the graph for both the pulse durations (Chronic04ms0.1ms and Chronic1ms0.1ms). The impact of the pulse duration on pulse height threshold increase is large, ranging from 133% for the comparison of biphasic pulses of 0.4 ms vs. 1 ms in the acute case (Acute1ms0ms vs. Acute04ms0ms). Importantly, these results are for fibre diameter 1 μm. The variations in pulse height threshold due to acute vs. chronic stimulations were also investigated for dependence on fibre diameter for fibers of 0.5 μm vs. 1 μm. It was found for the acute scenario, thresholds increase by approximately 80-90% for a fiber of diameter 0.5 μm compared to one of 1 μm fiber. The studies have indicated that the pulse height threshold increases with decreasing fiber diameters and the pulse height threshold may be decreased by increasing the pulse duration. In particular, the interphase delay of 0.2 ms demonstrated a potential advantage of 5-10% over a 0 ms interphase delay. FIG. 20 shows the ex-vivo validation of these in-silico calculations, and beyond 0.3 ms no further improvement in threshold reduction is noted, thereby further illustrating 0.2 ms as an optimal interphase parameter.

Figure 19:
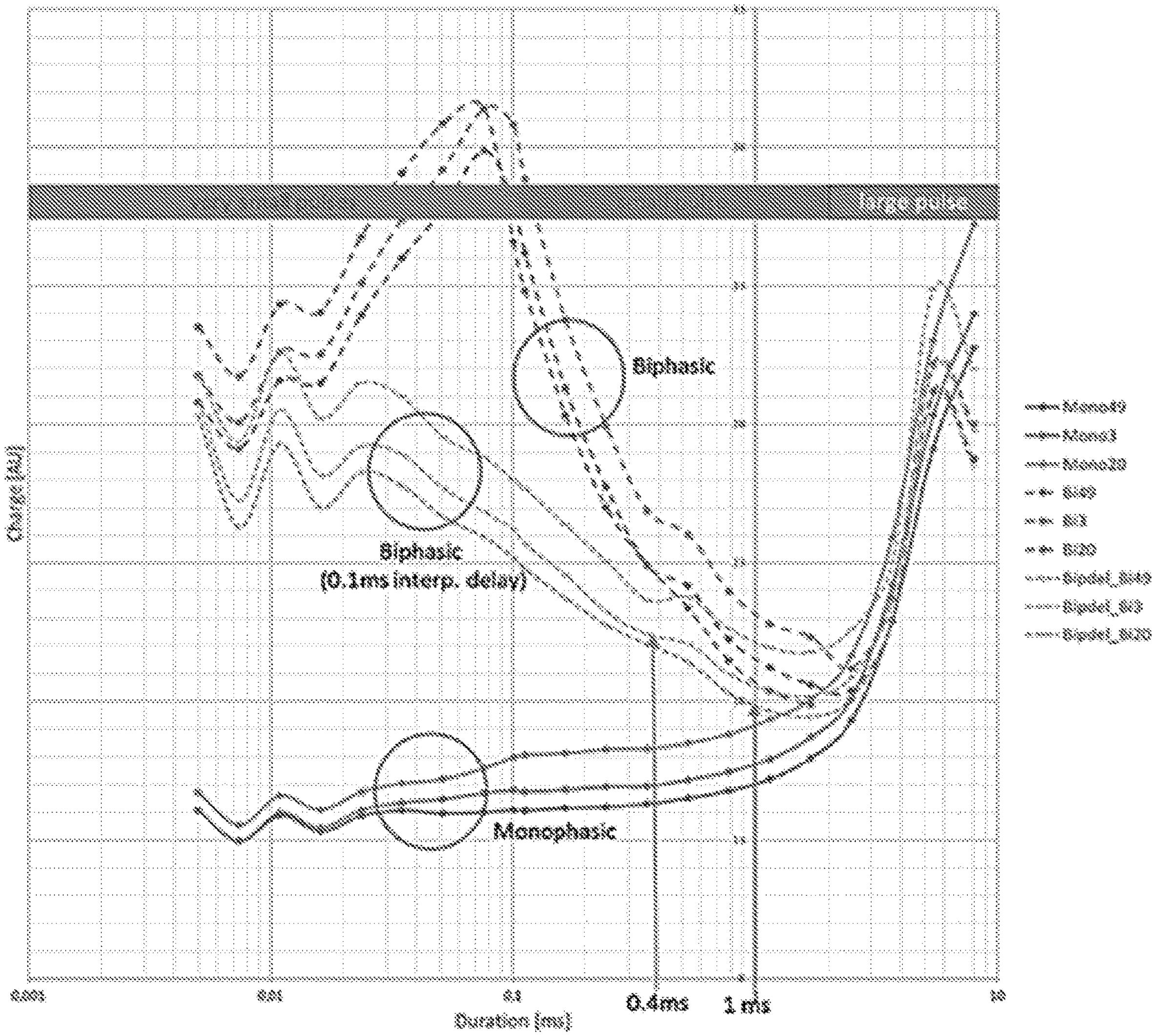
FIG. 19 shows the charge required to stimulate neural activity per pulse width in a human splenic nerve based on in-silico modelling data. Simulations are based on electrical signals with pulse trains having biphasic pulses with a 0 ms interphase delay ("Biphasic"), biphasic pulses with a 0.1 ms interphase delay ("Biphasic (0.1 ms interp. delay"), and monophasic pulses ("Monophasic").

The findings on pulse width in the ex-vivo preparations are further supported by this in-silico modelling data, as shown in FIG. 19. In particular, this figure shows that as the pulse width increases beyond 1 ms for a biphasic pulse train, the charge required to stimulate neural activity is reduced. Then, for pulse widths of 3 ms or higher, the charge required significantly increases.

Discussion

It was found that effects of interphase delay and pulse width are prominent. In particular, the interphase delay of 0.2 ms demonstrated a potential advantage of 5-10% over 0 ms interphase delay.

It is noted that these findings are supported by in-silico modelling data, as shown in FIG. 19. In particular, FIG. 19 shows that as the interphase delay of a biphasic pulse train is increased from 0 ms to 0.1 ms, the charge required to stimulate neural activity is reduced. It is further expected that as the interphase delay is increased beyond 0.1 ms, that the charge required to stimulate neural activity will reduce further and become closer to that required by a monophasic pulse train. Since it is not desirable to stimulate the nerve with a monophasic pulse train, a biphasic pulse train with an interphase delay greater than 0.1 ms is preferable. Other ex-vivo studies in unmyelinated fibers have found that for interphase delays greater than 300 μs, no further reduction in pulse amplitude threshold is found. This is depicted in FIG. 20. Accordingly, the preferable interphase delay for stimulation of a human splenic nerve is likely to be between 100 μs and 300 μs, more particularly between 200 μs and 250 μs.

Study 7: Porcine Ex-Vivo Comparator Studies

Figure 34:
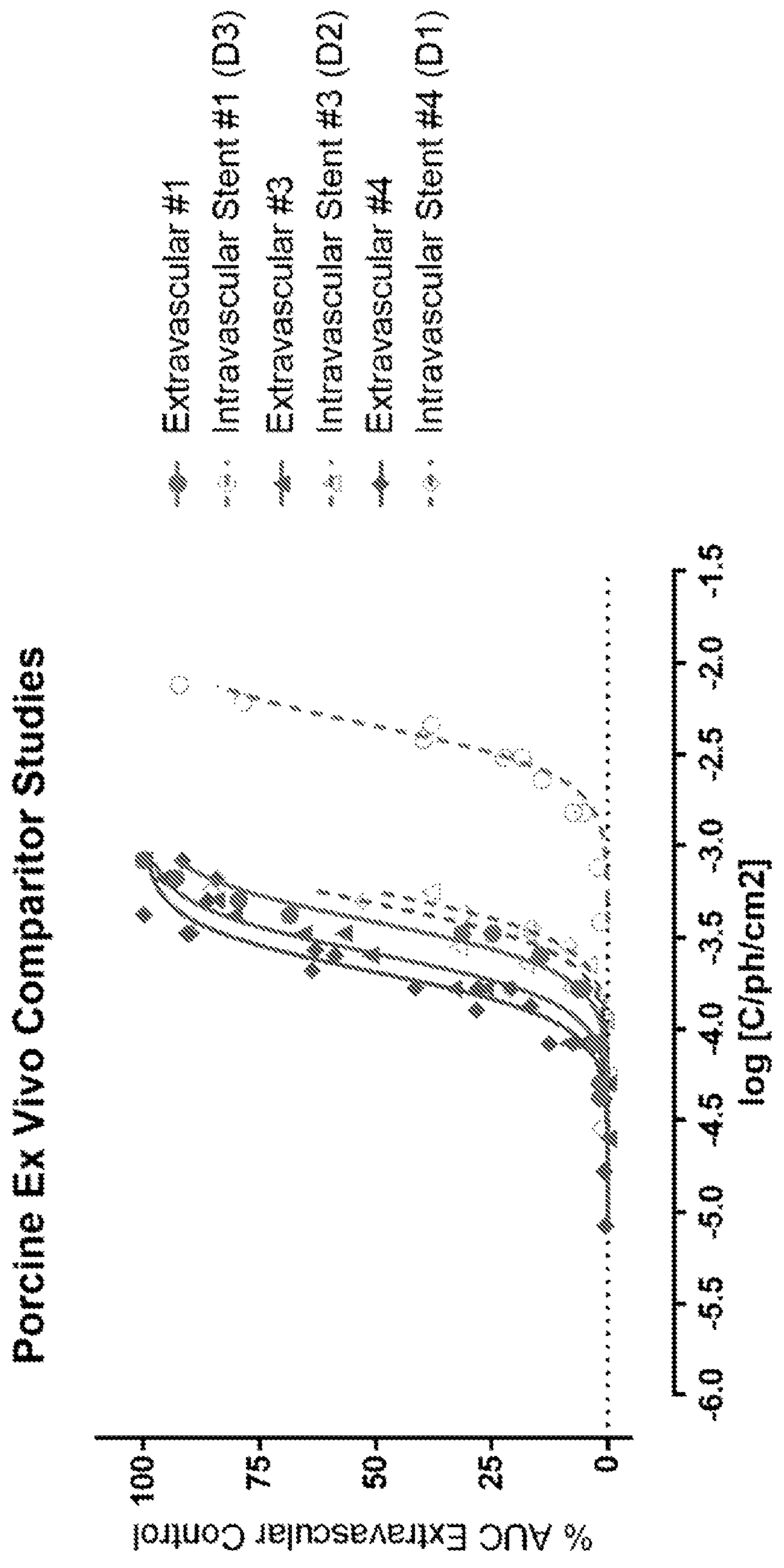
FIG. 34 shows porcine ex-vivo compartitor studies using a stent.

FIG. 34 shows results of a study in which an ex-vivo porcine splenic artery was utilized to compare nerve activation via extravascular (filled) vs intravascular (open) interfaces Similar symbols/colors represent paired measurements. The results of three varied intravascular designs are shown. The indwelling device used for these studies was a stent comprising electrodes. Current response curves have been converted to charge density (which may also be referred to as charge density per phase, C/ph/cm2) to illustrate the shift in charge density requirements when comparing extravascular to intravascular interfaces. As can be seen, x-axis refers to log[C/ph/cm$^2$]. Thus, the scale on the x-axis which spans from −6.0 to −1.5 refers to $10^{-6.0}$ to $10^{-1.5}$ C/ph/cm$^2$. The y-axis refers to area under the curve (AUC) for eCAP measurements (response curve from each experiment has been normalised). Intravascular stimulation requirements show a dextral displacement of the charge density curve by an average factor of 5.45×, ranging from 2.18 to 11.8×. Extravascular stimulation was delivered with 0.5-2 msec biphasic pulses up to 50 mA. Intravascular stimulation was delivered with 1-4 msec biphasic pulses up to 50 mA. Internal circumferential coverage of the intravascular electrodes ranged from 100% (D1/D2) to 50% (D3) of the arterial wall.

Study 8: Analysis of Porcine Model Simulation

The purpose of this study was to analyse the porcine computational models that use a catheter-based approach to simulate the neural tissue. The catheter is inserted into the splenic artery and unmyelinated axons are stimulated through the arterial wall.

Materials and Methods

Figure 22A:
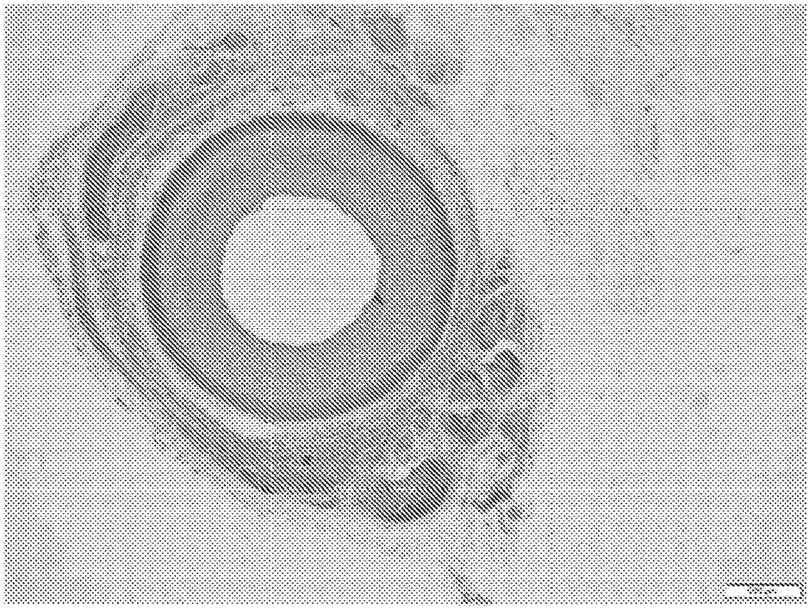
FIG. 22A shows a histology that served as the basis for the model in Study 8.
Figure 22B:
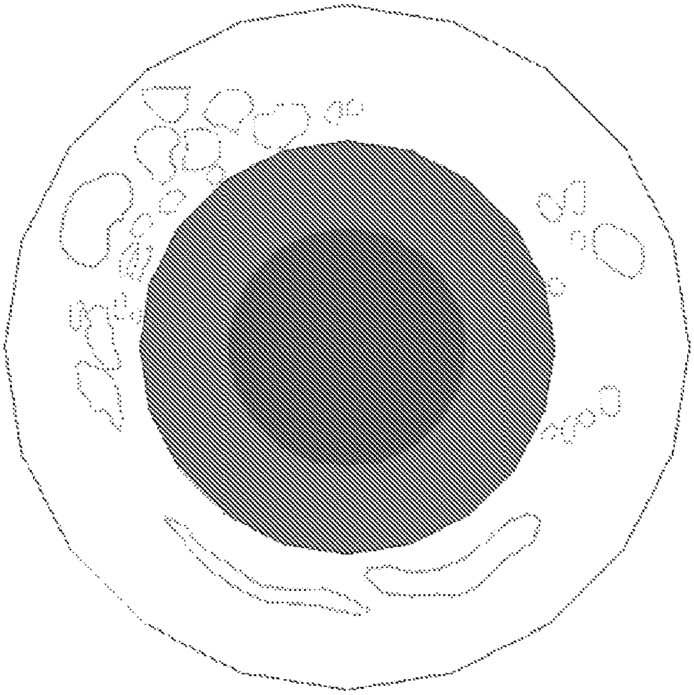
FIG. 22B shows the traced histology.

A histological cross section of the splenic artery is shown in FIG. 22A. The salient features of this cross section were traced and used to develop a model shown in FIG. 22B. After initially tracing the boundaries of the inner and outer arterial walls and the boundaries of the fascicles, the tissues were increased in size to account for an assumed 10% shrinkage that typically occurs during histological processing. A perineurium was added to every fascicle with a thickness equal to 3% of the equivalent fascicle diameter. The traced histology as well as the details about the catheter (discussed below) were used to develop the finite element model (FEM). The catheter was modelled as a 20-sided polyhedron composed of platinum electrodes.

Figure 23:
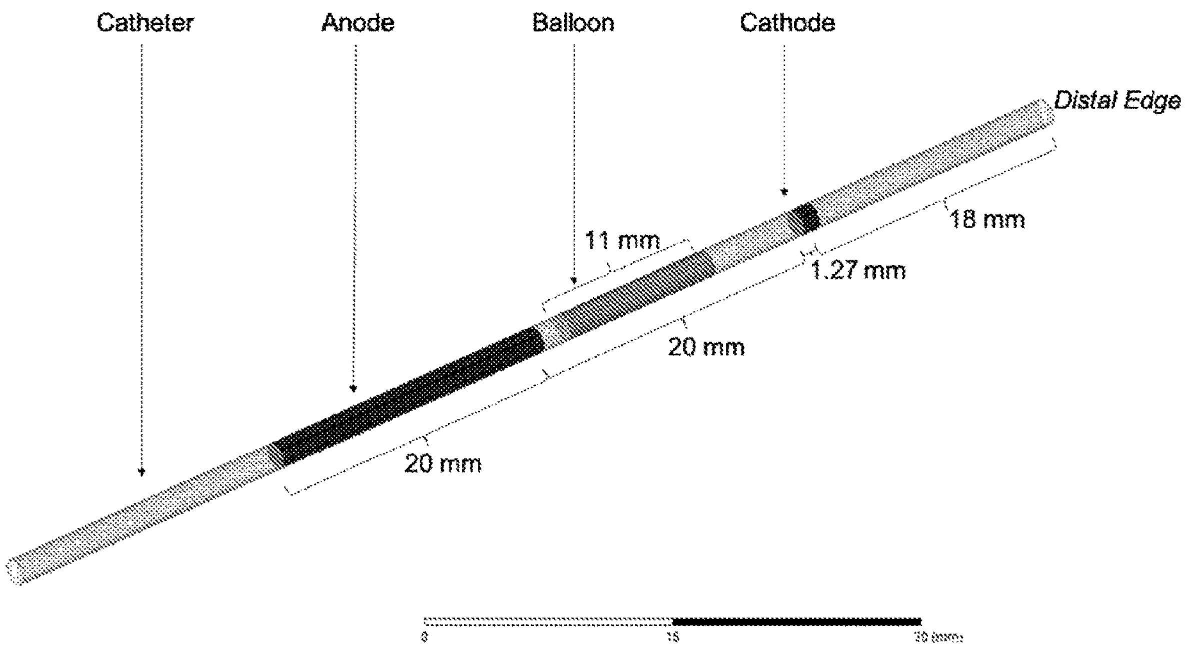
FIG. 23 shows the catheter of Study 8 developed in ANSYS Maxwell 3D. All dimensions are in mm
Figure 24:
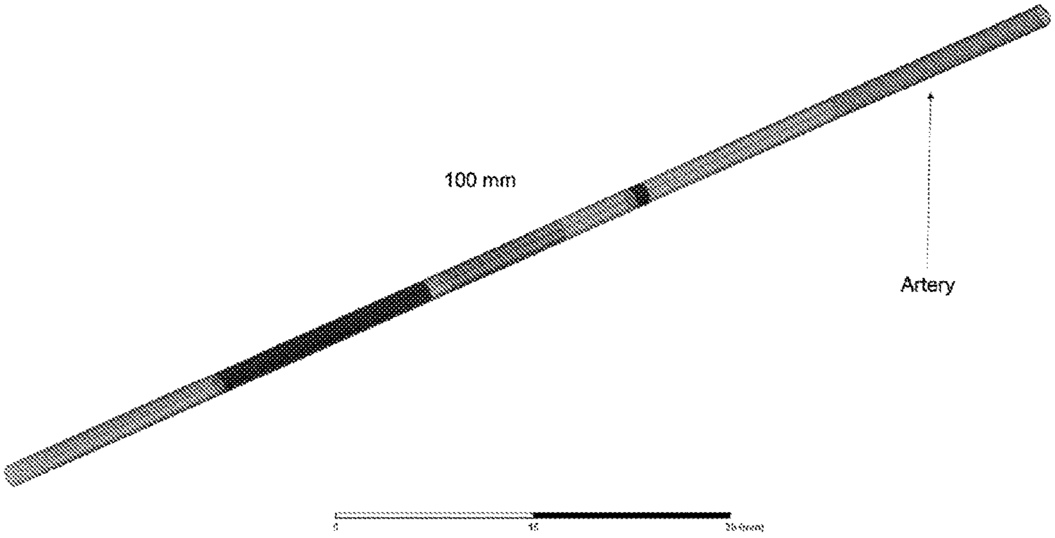
FIG. 24 shows the catheter of FIG. 23 within the artery of Study 8. All dimensions are in mm
Figure 25:
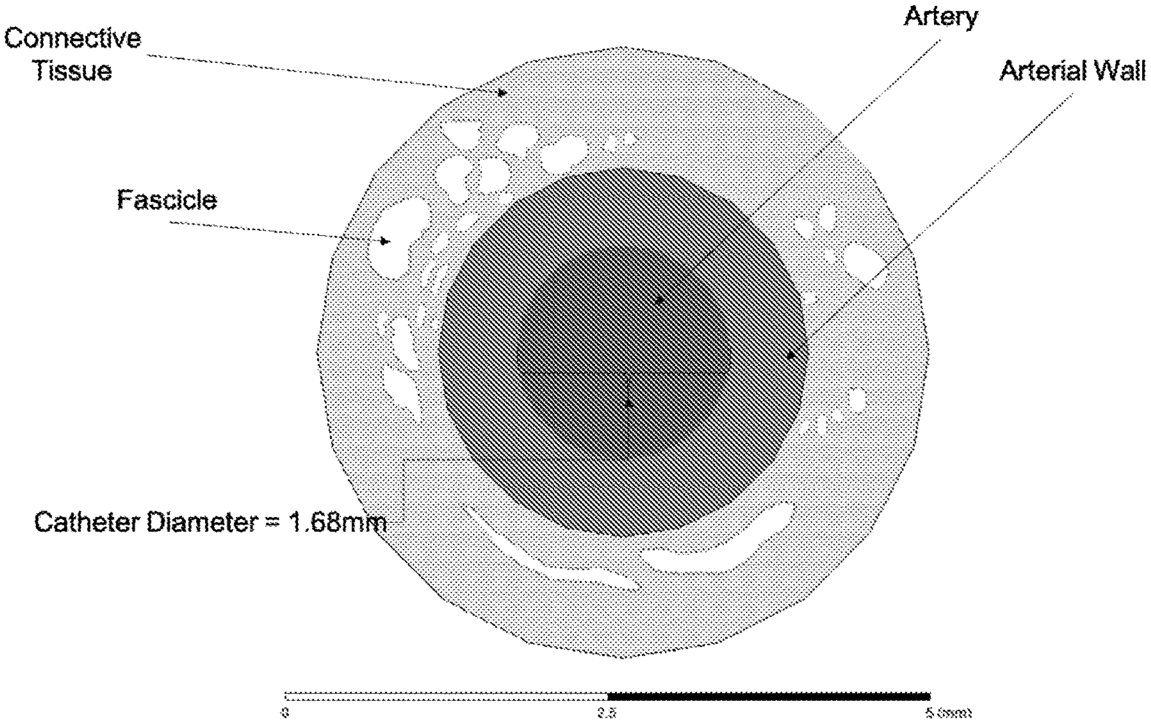
FIG. 25 shows the final cross-sectional image of the FEM following re-sizing to allow the catheter to fit in the artery.

The traced histology and the details about the catheter were used to develop the finite element method model (FEM). The catheter was modelled as a 20-sided polyhedron composed of platinum electrodes. The full length of the catheter was 79.27 mm Because the catheter was larger than the internal diameter of the artery, the artery was slightly increased in diameter to fit the catheter. The arterial wall thickness was fixed. The fascicles required a slight shift outward to ensure there was no overlap with the arterial wall. A figure illustrating the catheter is illustrated in FIG. 23. Similar to the catheter, the artery was modelled as concentric 20-sided polyhedrons. The artery was 100 mm in length. A figure illustrating the catheter inside the artery is shown in FIG. 24. The connective tissue surrounding the artery was modeled as a 20-sided polyhedron with a 4.8 mm diameter and a 100 mm length. A cross sectional image of the model is shown in FIG. 25. The catheter, artery, neural tissue, and surrounding connective tissue were enclosed in a 200 mm×200 mm×200 mm saline cube.

Dimensions of the catheter and tissues are provided in Table 1. Electrical conductivities are provided in Table 2, and material conductivities are provided in Table 3.

TABLE 1

Catheter and Tissue dimensions

| Dimensions | Value (mm) |
|---|---|
| Catheter | |
| Total length | 79.27 |
| Anode | 20 |
| Cathode | 1.27 |
| Balloon | 11 |
| Cathode-to-Edge | 18 |
| Anode-to-Cathode | 20 |
| Diameter | 1.68 |
| Artery | |
| Inner Artery Diameter | 1.68 |
| Artery Wall thickness | 0.61 |
| Outer Artery Diameter | 2.90 |
| Total length | 100 |
| Connective tissue | |
| Diameter | 4.8 |
| Length | 100 |

TABLE 2

Tissue conductivity

| Material | Conductivity (S/m) | Reference |
|---|---|---|
| Arterial Wall | 0.251 | [1] |
| Blood | 0.700 | [1] |
| Connective Tissue | 0.251-2.00 | [1], [2] |
| Endoneurium | 0.083 transverse (across)<br>0.571 longitudinal (along) | |
| Perineurium | 0.002 | [2] |
| Saline | 2.0 | [2] |

The assess the effect of connective tissue on threshold, the conductivity of the connective tissue was assumed to be 2.0 S/m, which is equal to saline. The current through the cathode was set to −1.0 mA. The current through the anode was set to +1.0 mA. Simulations were allowed to run with an iterative mesh refiner until error in the model fell below 1%, or 100 passes were completed.

TABLE 3

Material Conductivity (Non-tissues)

| Material | Conductivity (S/m) |
|---|---|
| Catheter | 0 |
| Balloon | 0 |
| Platinum | 9,300,000 |

Figure 26:
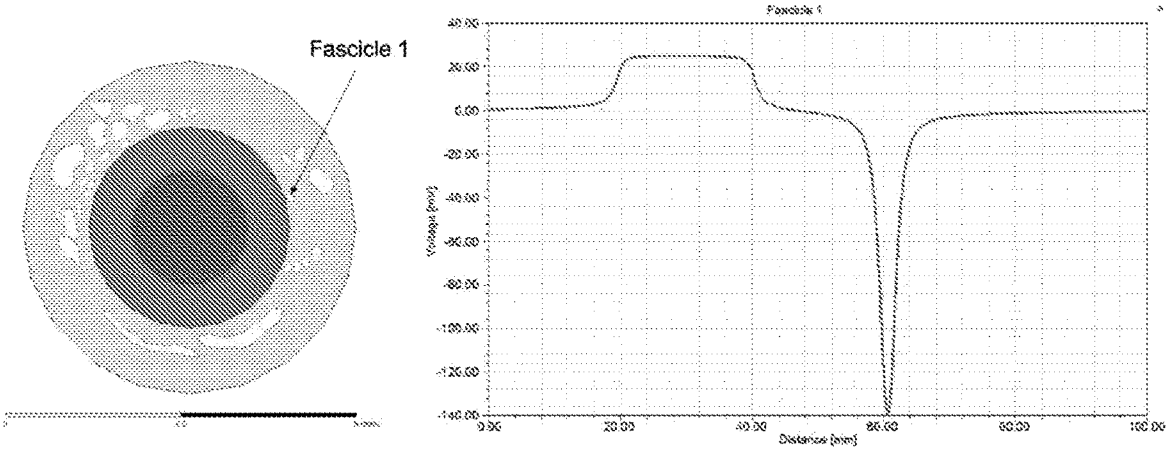
FIG. 26 shows the voltage along a line at the center of a fascicle resulting from a +1.0 mA anodic current and a −1.0 mA cathodic current.

FIG. 26 is an illustration of the voltage along a line at the center of Fascicle 1 near the artery. The 3D voltage fields contained in the nerve were exported to MATLAB for axon simulations.

The Tigerholm unmyelinated axon model was selected for the axon simulations [3]. 100 axons were randomly positioned in each fascicle. The extracellular potential along each axon was interpolated using a 3D cubic spline. With the given extracellular field, the strength-duration (threshold) curve was calculated for each axon for pulse widths ranging from 100-2000 μs.

Figure 27:
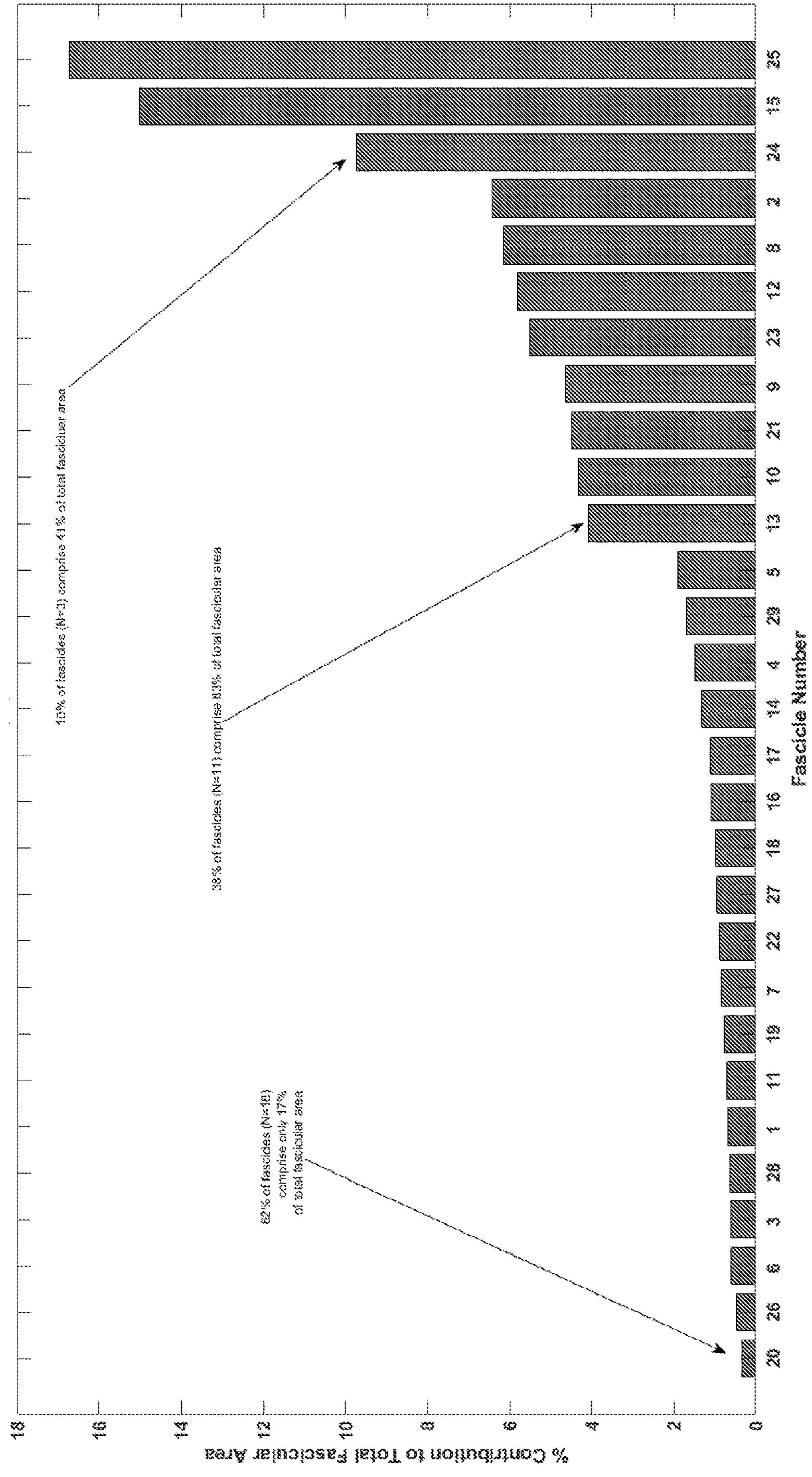
FIG. 27 shows a graph showing that most of the fascicles in the model were small, containing relatively few axons. 38% of the fascicles comprised 83% of the total fascicle area.

Results 100 axons were randomly positioned within each fascicle. Because each fascicle varied in size, in reality each fascicle would have different number of axons. Large fascicles would have more axons than small fascicles. Therefore, when calculating the overall thresholds of the axons, the threshold of the axons in the large fascicles were weighted more than the threshold in the smaller fascicles to produce a weighted average. Within this model, the 3 largest fascicles comprised 41% of the total fascicular area and, therefore, 41% of the overall axonal threshold response. Conversely, the 18 smallest fascicles comprised only 17% of the total fascicular area. Each fascicle's relative contribution to the total fascicular area, and, therefore, weighted contribution to the average threshold, is shown in FIG. 27.

Figure 28:
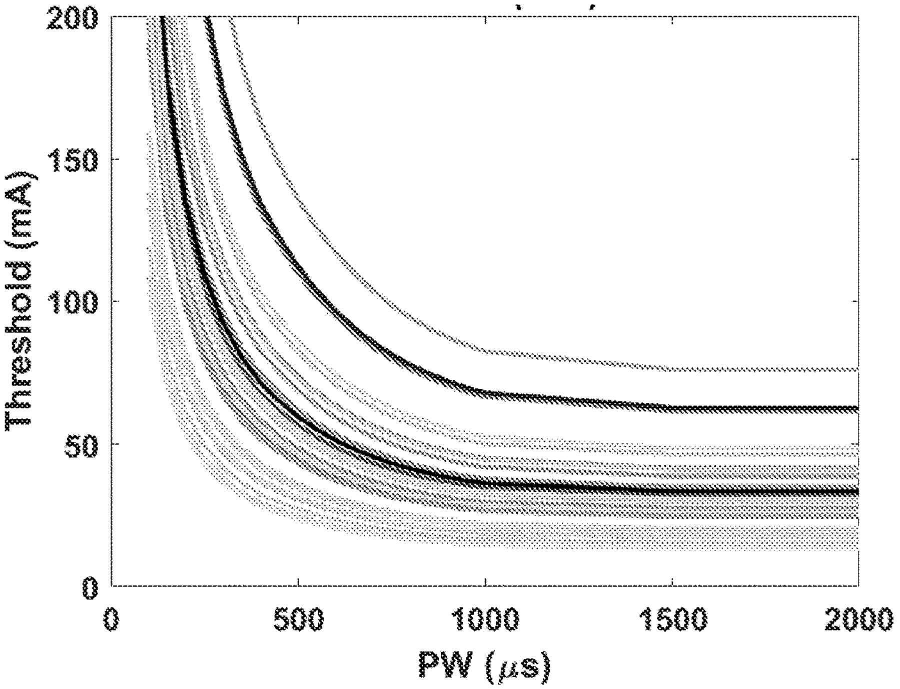
FIG. 28 shows a graph showing the average threshold for the 100 axons within each fascicle. The 29 lines are from the 29 fascicles in the model. The darker the line, the larger the cross-sectional area of that fascicle and the more axons within the entire axon population that are represented by the line.
Figure 29:
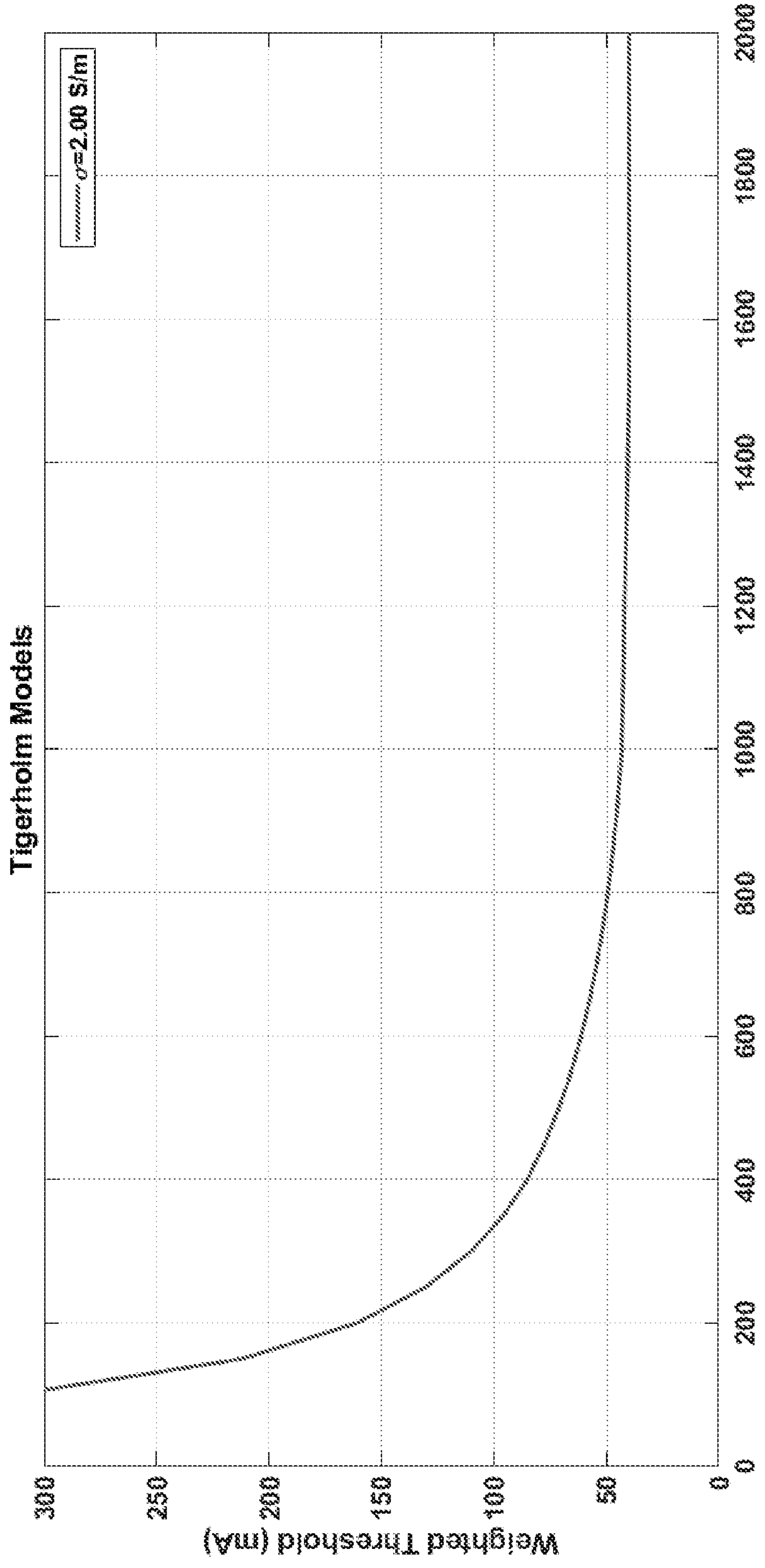
FIG. 29 shows a graph showing the average threshold for all axons within the model.

The average threshold of the 100 axons within each of the 29 fascicles are shown in FIG. 28. The darker the curve, the larger the fascicle and overall relative contribution to the average. Using the weighting method described above, the overall threshold for the axons within the population was found and plotted in FIG. 29.

The data illustrates that for 1 ms pulse width, a charge density of approximately 600 μC/cm$^2$ (approx. 40 mA) is required to recruit 50% of the axon population. 100% recruitment can be interpolated to approx. 1500 μC/cm2. The data also suggests that a higher pulse width is more appropriate for recruitment as the steepness of the curve increases with decreasing pulse width. Furthermore, the data is in good alignment with the experimental data where ~50% eCAP activation is noted at approximately 600 μC/cm$^2$.

Figure 30:
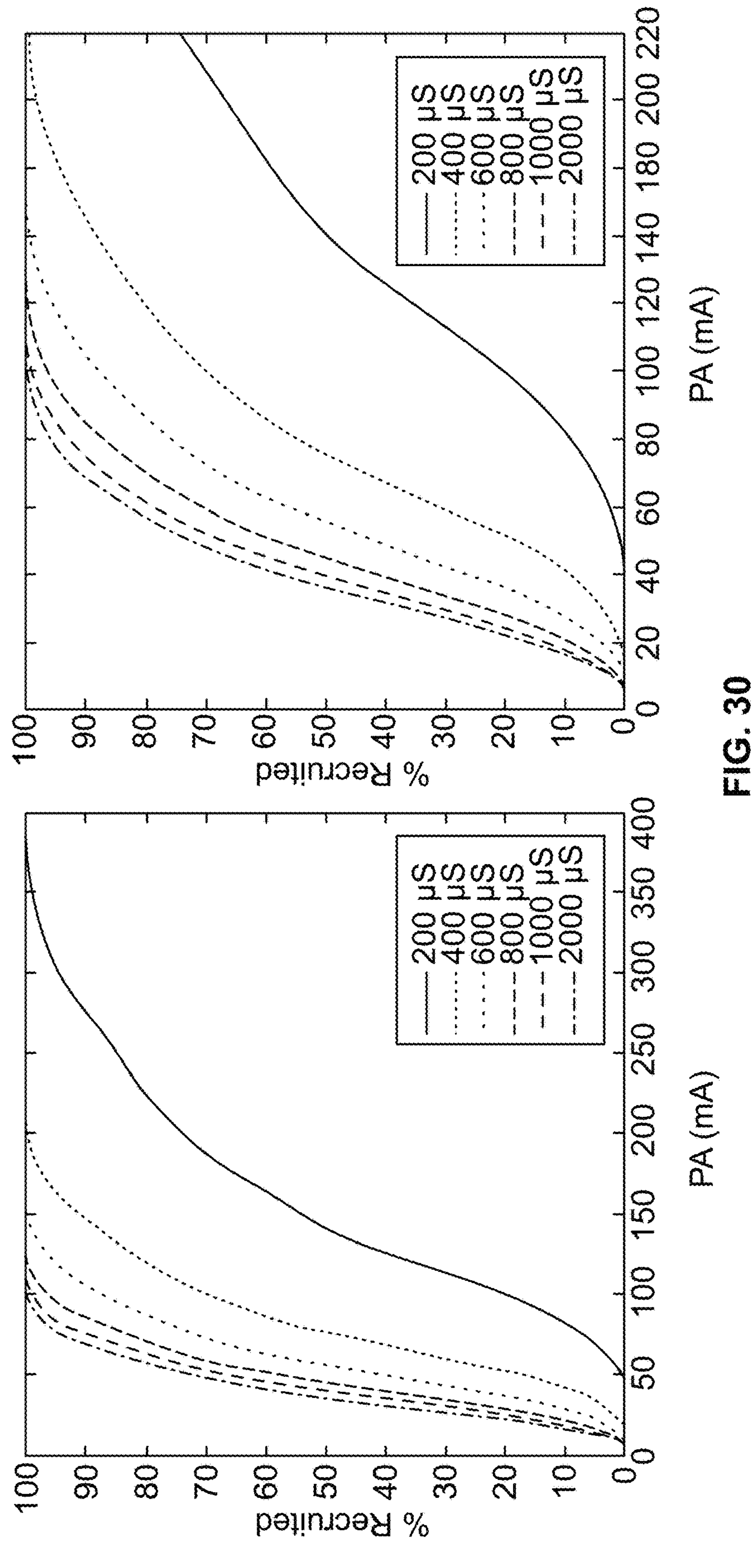
FIG. 30 shows results from Study 8.
Figure 31:
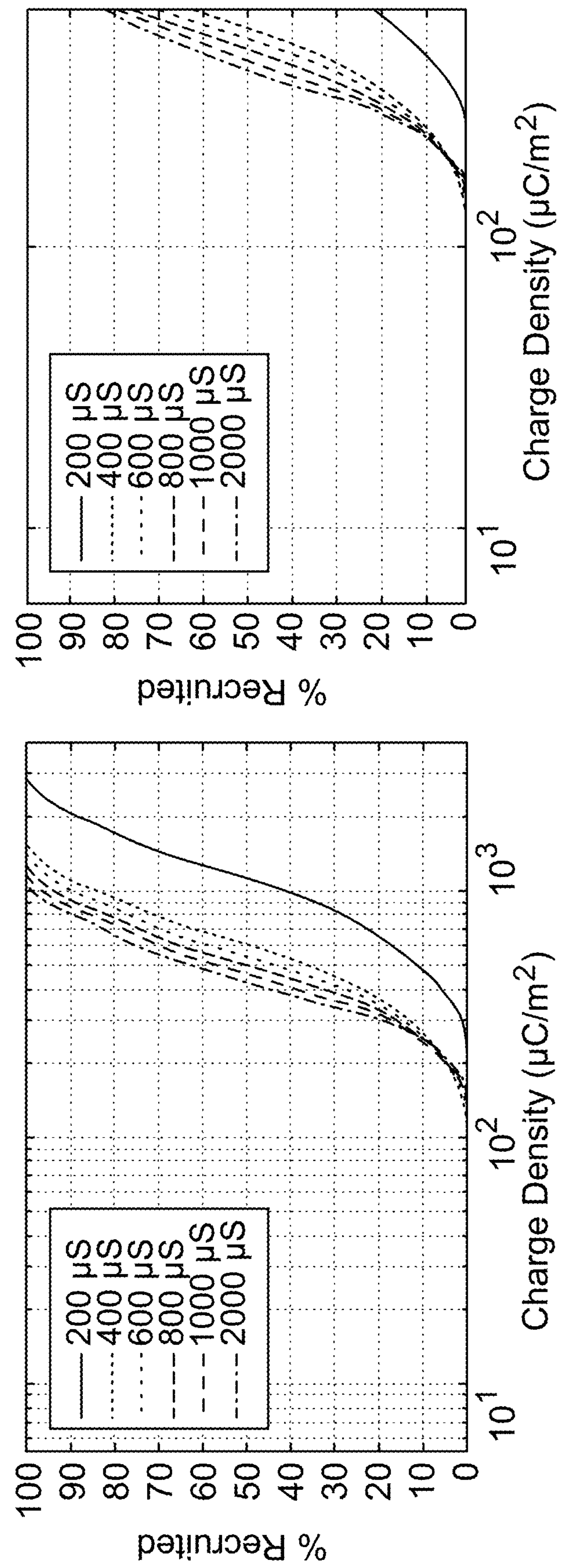
FIG. 31 shows results from Study 8.
Figure 32A:
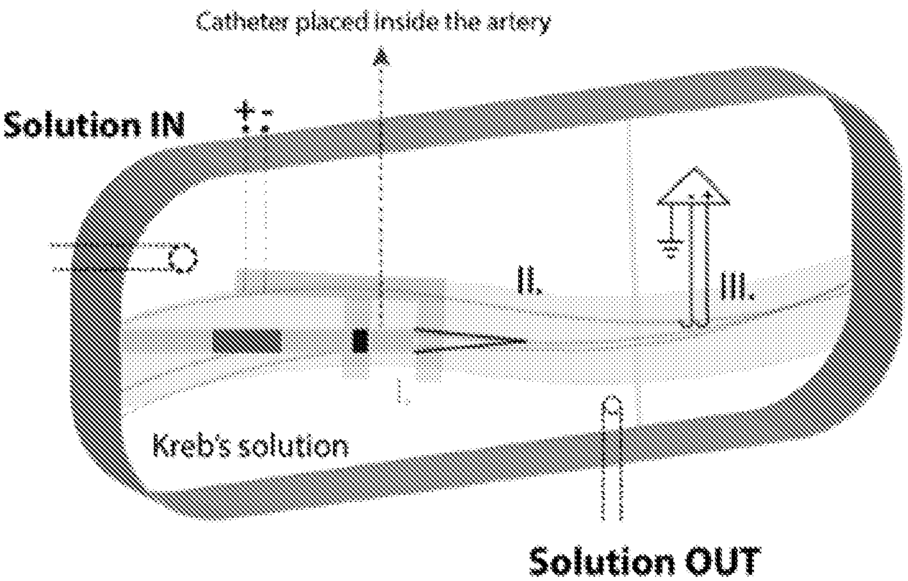
FIG. 32 shows electrophysiological characterisation in human splenic neurovascular bundle. (A) Conceptual sketch of tissue with the catheter, and hook placement for recording the compound action potentials, (B) An illustration of used catheter, (C) An example of the human splenic tissue as received. The purple dots on the sample indicates the top part of the splenic artery with aorta towards the left end, and spleen on the right end of the sample (for orientation), (D) This nerve is dissected, placed in a bath with Kreb' s solution, and traced all along till the end of the sample, where the hooks are placed to record compound action potentials, and (E) An example of eCAP observed on the oscilloscope.
Figure 32B:
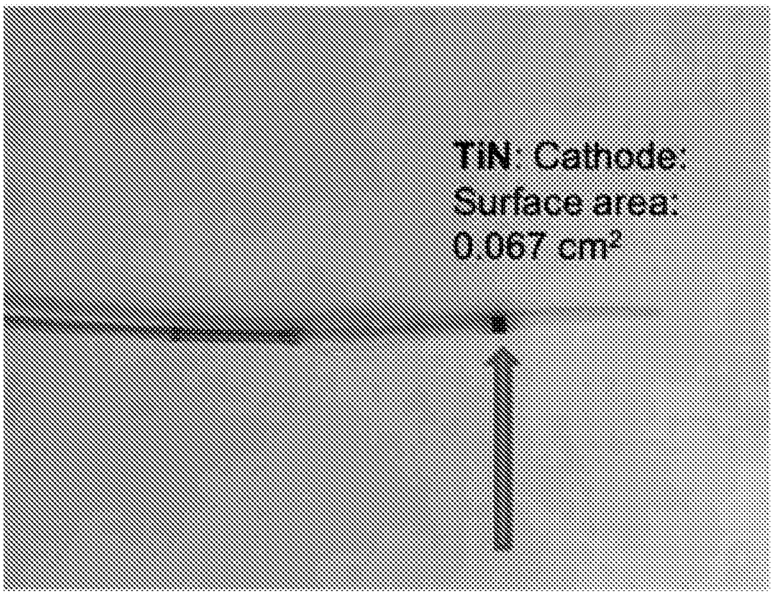
Figure 32C:
Figure 32D:
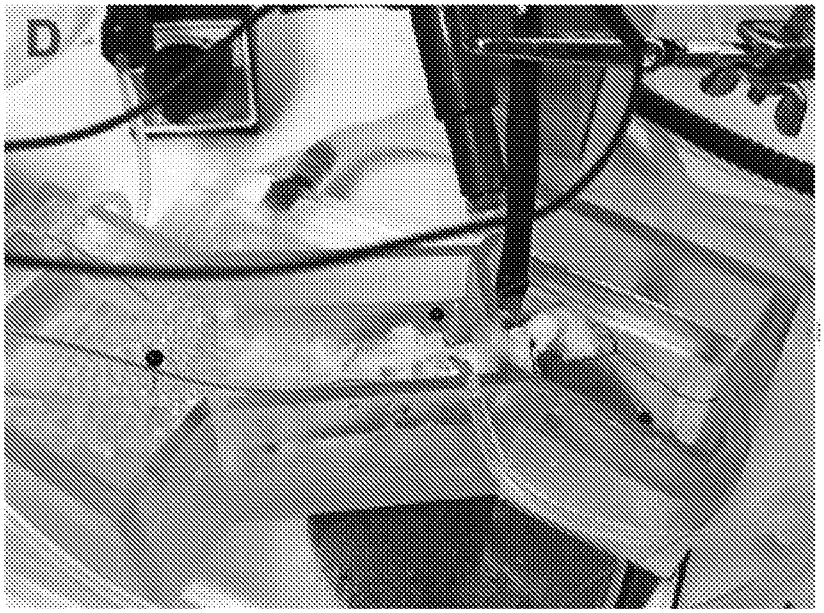
Figure 32E:
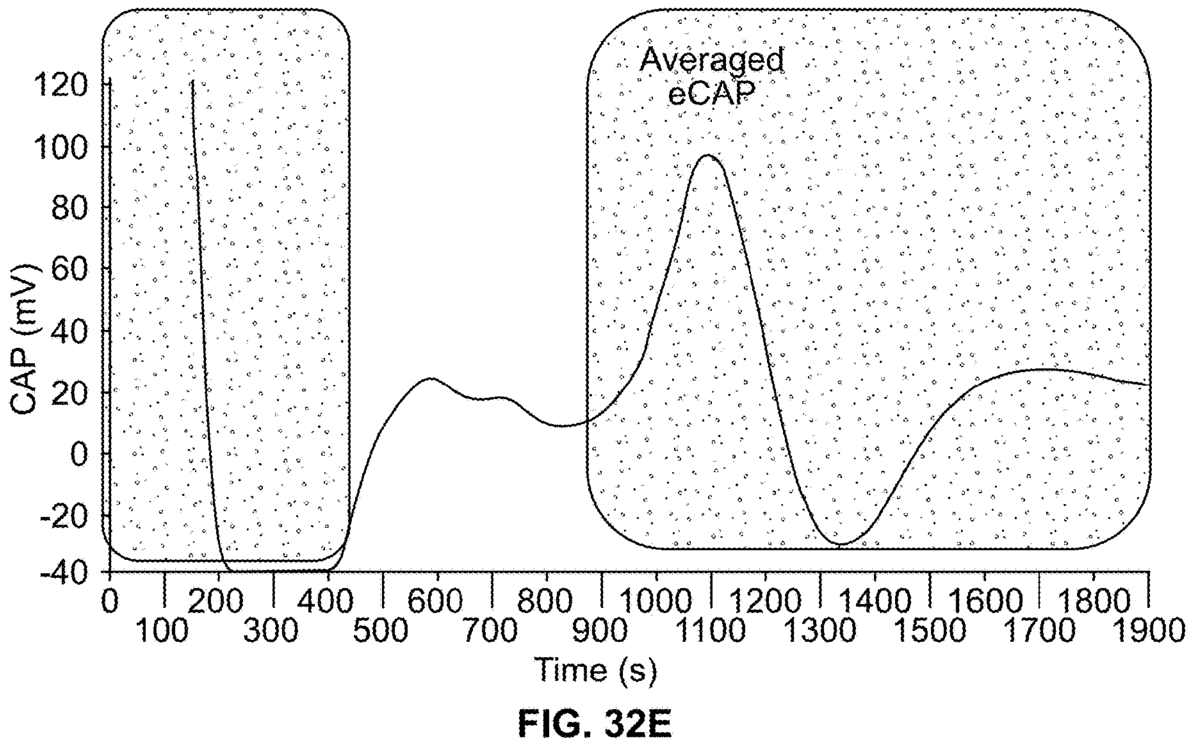

FIG. 30 shows pulse amplitude recruitment curve for different pulse widths in the model (200-2000 μs). FIG. 31 shows charge density curves for different pulse widths in the model (200-2000 μs).

Study 9: Ex-Vivo Electrophysiological Study of Human Tissue

The purpose of this study was to estimate indicative stimulation parameters of human splenic nerves in order to de-risk and optimize the biological efficacy and reproducibility of stimulation parameters of the electrical signal for use in humans using a catheter, in particular for stimulation of a human splenic nerve. The study was performed using ex-vivo using human splenic samples.

Materials and methods

FIG. 32 show the setup for the electrophysiological characterisation of the human splenic neurovascular bundle using a catheter placed inside the artery. The setup of the study is shown in FIG. 32A, B. A catheter is placed inside the artery as oppose to the peri-vascular cuff. An example of fresh NVB sample from a donor is illustrated in FIG. 32C. The sample is placed in a petri dish containing Kreb's solution and the NVB is carefully surgically isolated from excess adipose tissue under a microscope. The purple dots on the sample indicates the top part of the splenic artery used in order to maintain the orientation of the sample. A few splenic nerves were carefully isolated distally for the purpose of recording eCAPs (FIG. 32D). Nerve activity in the human electrophysiology study was continuously monitored using an oscilloscope, and digitally recorded with a 1401 acquisition system and Spike 2 v8.0 software with a sample rate set at 20 KHz (FIG. 32E). Evoked CAPs were averaged (8 pulses) and rectified for area under the curve for the average response.

Results

Figure 33:
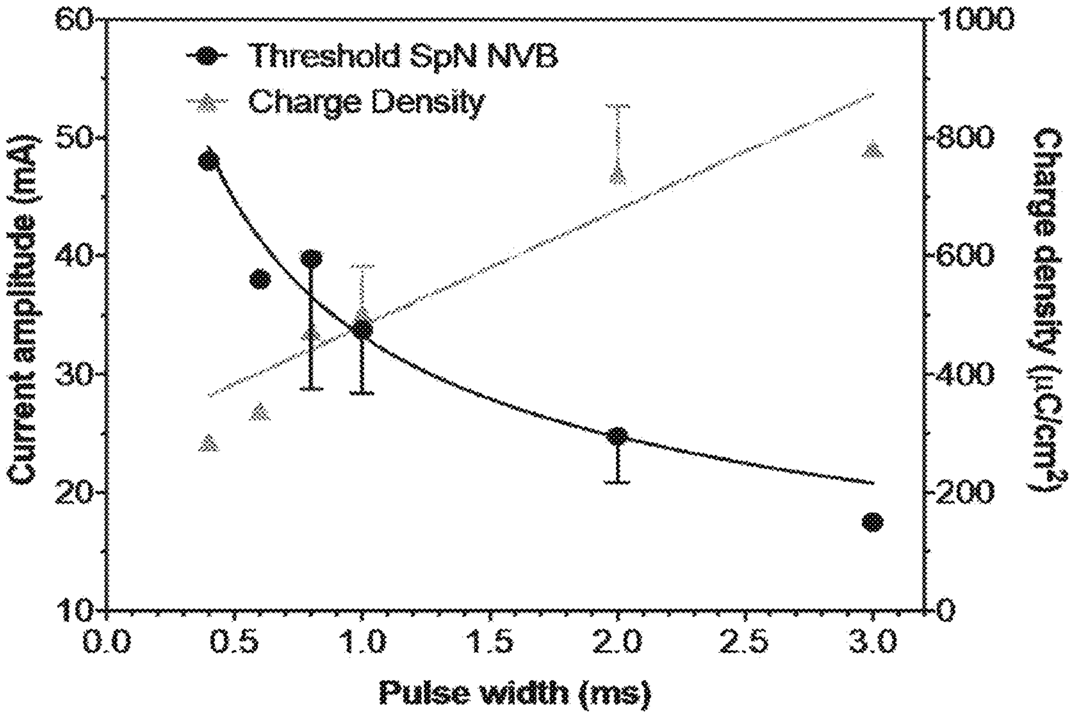
FIG. 33 shows a graph showing strength-duration curves from two samples. The black dots and the grey triangles shows the average of threshold of current amplitude and charge density.

Strength-duration curves from two samples are illustrated in FIG. 33. Threshold values for four different pulse widths of 400 μs, 1 ms, 2 ms and 3 ms were found to be 48 mA, 33.75 mA, 24.75 mA and 17.5 mA. Charge densities with surface area of 0.067 cm2 are estimated to be at 286.56, 503.73, 738.8 and 783.58 μC/cm$^2$.

| Charge Density (μC/cm2) | 286.56 | 503.73 | 738.8 | 783.58 |
|---|---|---|---|---|
| Pulse width (ms) | 0.4 | 1 | 2 | 3 |
| Current Amplitude (mA) | 48 | 33.75 | 24.75 | 17.5 |

Discussion

The presented values are indicative of threshold, or 10% recruitment of the nerves. Full recruitment curves for these samples were not recorded due to the limitation on the external pulse generator used for stimulation of the nerves. With respect to the extravascular data presented in the Study 5, there was approximately 7× fold increase in charge densities.

REFERENCES

[1] "https://itis.swiss/virtual-population/tissue-properties/database/tissue-frequency-chart/.".

[2] A. Q. Choi, J. K. Cavanaugh, and D. M. Durand, "Selectivity of multiple-contact nerve cuff electrodes: A simulation analysis," *IEEE Trans. Biomed. Eng.*, vol. 48, no. 2, pp. 165-172, 2001.

[3] J. Tigerholm et al., "Modeling activity-dependent changes of axonal spike conduction in primary afferent C-nociceptors," *J. Neurophysiol.*, vol. 111, no. 9, pp. 1721-1735,2013.

The invention claimed is:

1. A neurostimulation device for non-destructively stimulating neural activity in a nerve in proximity to a blood vessel for treating an acute medical condition or inflammatory disorder, the neurostimulation device comprising:

an indwelling device capable of insertion into a blood vessel and configured to be placed inside the blood vessel for stimulating the nerve; and a proximal electrode offset from a distal electrode along a length of the indwelling device, wherein the proximal electrode is an anode electrode and has a larger surface area than the distal electrode, an insulator positioned between the proximal electrode and the distal electrode on the indwelling device, wherein the insulator is positioned closer to the proximal electrode than the distal electrode, such that the insulator keeps the proximal electrode in a central location approximately equal around the inside circumference of the blood vessel, and wherein the electrodes are configured to apply a non-destructive electrical signal to the nerve and connectable to a stimulator, wherein the non-destructive electrical signal for stimulating the nerve comprises a pulse train having a pulse width ≥0.1 ms and ≤5 ms and wherein the non-destructive electrical signal propagates an action potential distally towards an organ and produces an improvement in a physiological parameter in a subject, and wherein the improvement in the physiological parameter is one or more of a group consisting of: stabilization of blood pressure, prevention of an inflammatory response, suppression of an inflammatory response, or reduction in an inflammatory response.

2. The neurostimulation device of claim 1, wherein the pulse train has an interphase delay of delay of ≤0.3 ms and ≥0.1 ms.

3. The neurostimulation device of claim 1, wherein the charge density per phase applied to the nerve by the non-destructive electrical signal is ≥20 μC per $cm^2$ per phase and ≤850 μC per $cm^2$ per phase.

4. The neurostimulation device of claim 1, wherein the charge density per phase applied to the nerve by the non-destructive electrical signal is ≥20 μC per $cm^2$ per phase and ≤4000 μC per $cm^2$ per phase.

5. The neurostimulation device of claim 1, wherein the proximal electrode is offset from the distal electrode by a minimum spacing of 1.5 cm along the length of the indwelling device.

6. The neurostimulation device of claim 1, wherein the proximal electrode is offset from the distal electrode by a maximum spacing of 4 cm along the length of the indwelling device.

7. The neurostimulation device of claim 1, wherein the proximal electrode is offset from the distal electrode by a spacing of 2 cm along the length of the indwelling device.

8. The neurostimulation device of claim 1, wherein the proximal electrode is an anode electrode during the stimulation phase of a bipolar pulse and wherein the anode is at least 1 cm in length.

9. The neurostimulation device of claim 1, wherein the proximal electrode and/or the distal electrode is coated in Titanium Nitride, Iridium Oxide, PEDOT or Platinum Grey.

10. The neurostimulation device of claim 1, wherein the distal electrode has a surface area of between 0.01 $cm^2$ and 0.1 $cm^2$.

11. The neurostimulation device of claim 1, further comprising a second insulator positioned between the distal electrode and the distal end of the indwelling device.

12. The neurostimulation device of claim 1, wherein the neurostimulation device is configured to be placed inside the splenic artery for stimulating a splenic nerve.

13. The neurostimulation device of claim 1, wherein the insulator has a contracted configuration in which the size of the insulator allows the indwelling device to travel inside the blood vessel;

the insulator has an expanded configuration in which the insulator blocks blood flowing through the blood vessel between the proximal electrode and the distal electrode;

the stimulator is configured to apply an electrical signal between the proximal electrode and the distal electrode when the insulator is in the expanded configuration, thus inducing electrical activity in a wall portion of the blood vessel between the proximal and distal electrodes; and an insulation portion between the distal electrode and a distal end of the indwelling device for offsetting the distal electrode from the wall of the blood vessel.

14. The neurostimulation device of claim 1, wherein the non-destructive electrical signal for stimulating the nerve comprises a pulse train having a pulse width >1 ms and ≤5 ms.

* * * * *